US005856188A

United States Patent [19]
Hampel et al.

[11] Patent Number: 5,856,188
[45] Date of Patent: *Jan. 5, 1999

[54] HAIRPIN RIBOZYMES

[75] Inventors: Arnold E. Hampel; Richard H. Tritz, both of DeKalb, Ill.; Margaret F. Hicks, Antioch, Tenn.

[73] Assignees: The Board of Regents for Northern Illinois University of DeKalb, DeKalb; Biotechnology Research and Development Corporation, Peoria, both of Ill.

[*] Notice: The term of this patent shall not extend beyond the expiration date of Pat. No. 5,527,895.

[21] Appl. No.: 485,689

[22] Filed: Jun. 7, 1995

Related U.S. Application Data

[62] Division of Ser. No. 78,774, Jun. 17, 1993, which is a continuation of Ser. No. 703,427, May 14, 1991, abandoned, which is a continuation-in-part of Ser. No. 577,658, Sep. 4, 1990, abandoned, which is a continuation-in-part of Ser. No. 409,666, Sep. 20, 1989, abandoned, which is a continuation-in-part of Ser. No. 247,100, Sep. 20, 1988, abandoned.

[51] Int. Cl.$^6$ .................. C12N 5/00; C12Q 1/68; C07H 21/04
[52] U.S. Cl. .................. 435/375; 435/6; 435/91.31; 435/172.3; 435/320.1; 435/325; 435/366; 435/410; 536/23.1; 536/23.2; 536/24.5; 514/44
[58] Field of Search .................. 435/6, 91.31, 320.1, 435/172.3, 172.1, 240.1, 240.2, 252.3, 252.33, 410, 366, 325, 375; 536/23.1, 23.2, 24.5; 514/44; 800/205

[56] References Cited

FOREIGN PATENT DOCUMENTS

| 3-21201AP | 4/1989 | European Pat. Off. |
| 88/04300 | 7/1988 | WIPO |

OTHER PUBLICATIONS

Barinaga, Science 262:1512–1514 (1993).
Stull et al. Phesm. Res. 12: 465–483 (1995).
Alton and Vapnak. Nature, 282:864 (1979).
Beaucage and Caruthers, Tetrahedron Letters, 22:1859 (1981).
Brueing et al., Structure and Expression vol. I: From Proteins to Ribosomes, Adenine Press, New York (Mar. 1988), pp. 239–248.
Bruening, et al., RNA Genetics: Retroviruses, Viroids, and RNA Recombination vol. II, CRC Press (1988), pp. 127–145.
Bruening, et al., Plant Molecular Biology, Plenum Press, New York (1987), pp. 495–502.
Buzayan, et al., Proc. Natl. Acad. Sci., 83:8859 (1986).
Buzayan, et al., Virology, 151:186 (1986).
Buzayan, et al., Nature, 323:349 (1986).
Buzayan, et al., Nucleic Acids Research, 14:9729 (1986).
Buzayan, et al., Biochem. Biophys. Res. Comm, 156:340 (1988).
Buzayan, et al., Nucleic Acids Research, 16:4009 (1988).
Cech, Science, 236:1532 (1987).
Cech and Bass, Ann. Rev. Biochem., 55:599 (1986).
Devereux, et al., Nucleic Acids Research, 12:387 (1984).
Diener et al., Proc. Nat'l Acad. Sci., 83:58–62 (1986).
Donis–Keller, et al., Nucleic Acids Reaearcgh, 4:2527 (1977).
Epstein and Gall, Cell, 48:535 (1987).
Feldstein, et al., Gene, 82:53 (1989).
Forster and Symons, Cell 50:9 (1987).
Forster and Symons, Cell 49:211 (1987).
Fox and Woese, Nature, 256:505 (1975).
Freier, et al., Biochemistry, 22:6198 (1983).
Freier, et al., Proc. Natl. Acad. Sci., 83:9373 (1986).
Biotechnology Newswatch, Aug. 29, 1989, pp. 2–3.
Gerlach, et al., Virology, 151:172 (1986).
Hampel and Tritz, Journal of Cellular Biochemistry, 12D:31 (1988).
Hampel and Tritz, Biochemistry, 28:4929 (1989).
Hampel and Tritz, Self–Cleavage RNA as an Anit–HIV Agent: Design and Delivery to Cells, Jun. 21–23, 1989, Rockville, Maryland.
Haseloff and Gerlach, Nature, 334:585 (1988).
Haseloff and Gerlach, Gene, 82:43 (1989).
Hutchins, et al., Nucleic Acids Research, 14:3627 (1986).
Ito, et al., Nucleic Acids Research, 10:1755 (1982).
Koizumi, et al., FEBS Letters, 228:228 (1988).
Matteucci and Caruthers, Tetrahedron Letters, 21:719 (1980).
Matteucci and Caruthers, J. Am. Chem. Soc., 103:3185 (1981).
McSwiggen and Cech, Science, 244:679 (1989).
Milligan, et al., Nucleic Acids Research, 15:8783 (1987).
Muesing, et al., Nature, 313:450 (1985).
Pace et al., Gene, 82:65–75 (1989).
Prody, et al., Science, 231:1577 (1986).
Ruffner, et al., Gene, 82:31 (1989).
Sanchez–Pescador, et al., Science, 227:484 (1985).
Sarin, et al., Proc. Natl. Acad. Sci., 85:7448 (1988).
Sharmeen, et al., Journal of Virology, 62:2674 (1988).
Sugimoto, et al., Biochemistry, 26:4554 (1987).
Tritz et al., The FASEB Journal, vol. 2, No. 4, 15 Mar. 1988, abstract 1418.

(List continued on next page.)

*Primary Examiner*—John L. LeGuyader
*Attorney, Agent, or Firm*—John P. White; Cooper & Dunham LLP

[57] ABSTRACT

A synthetic RNA catalyst capable of cleaving an RNA substrate, the catalyst comprising a substrate binding portion and a "hairpin" portion. The invention also provides an engineered DNA molecule and a vector, each comprising a DNA sequence coding for an RNA catalyst according to the invention. The invention further comprises host cells transformed with the vectors of the invention which are capable of expressing the RNA catalyst. Finally, the invention provides a method of cleaving an RNA substrate which comprises contacting the substrate with a synthetic RNA catalyst according to the invention.

12 Claims, 62 Drawing Sheets

OTHER PUBLICATIONS

Tritz and Hampel, Journal of Cell Biology, 107:321a (1988).
Tritz and Hampel, The FASEB Journal, 2:A539 (1988).
Turner, et al., Ann. Rev. Biophys. Chem., 17:167 (1988).
Uhlenbeck, Nature, 328:596 (1987).
Walbot and Bruening, Nature, 334:196 (1988).
Wu and Lai, Science, 243:652 (1989).
Wu, et al., Proc. Natl. Acad. Sci., 86:1831 (1989).
Zuker and Stiegler, Nucleic Acid Research, 9:133 (1981).

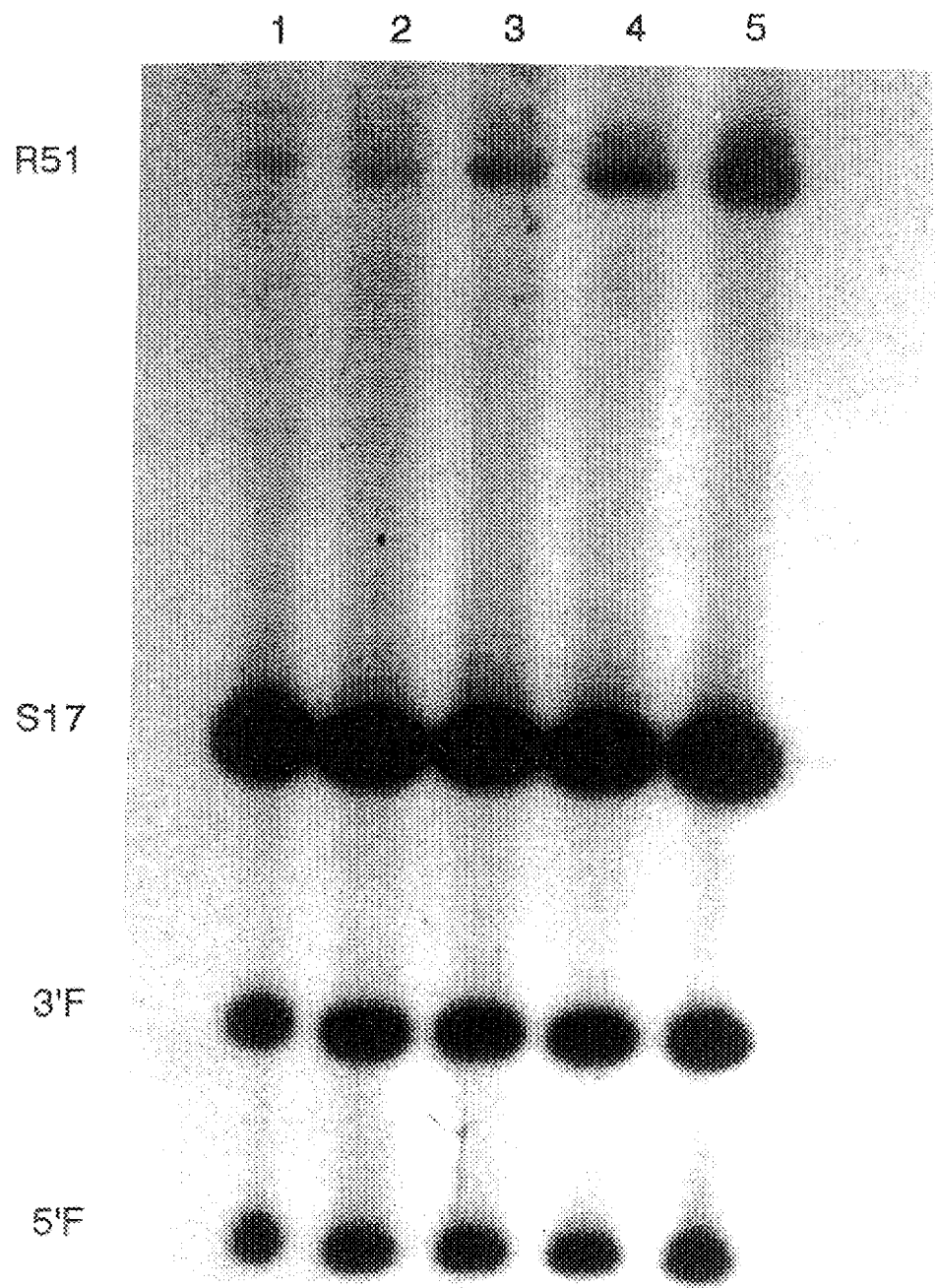

Substrate RNA

Substrate RNA

S

3' F

5' F

S

3' F

5' F

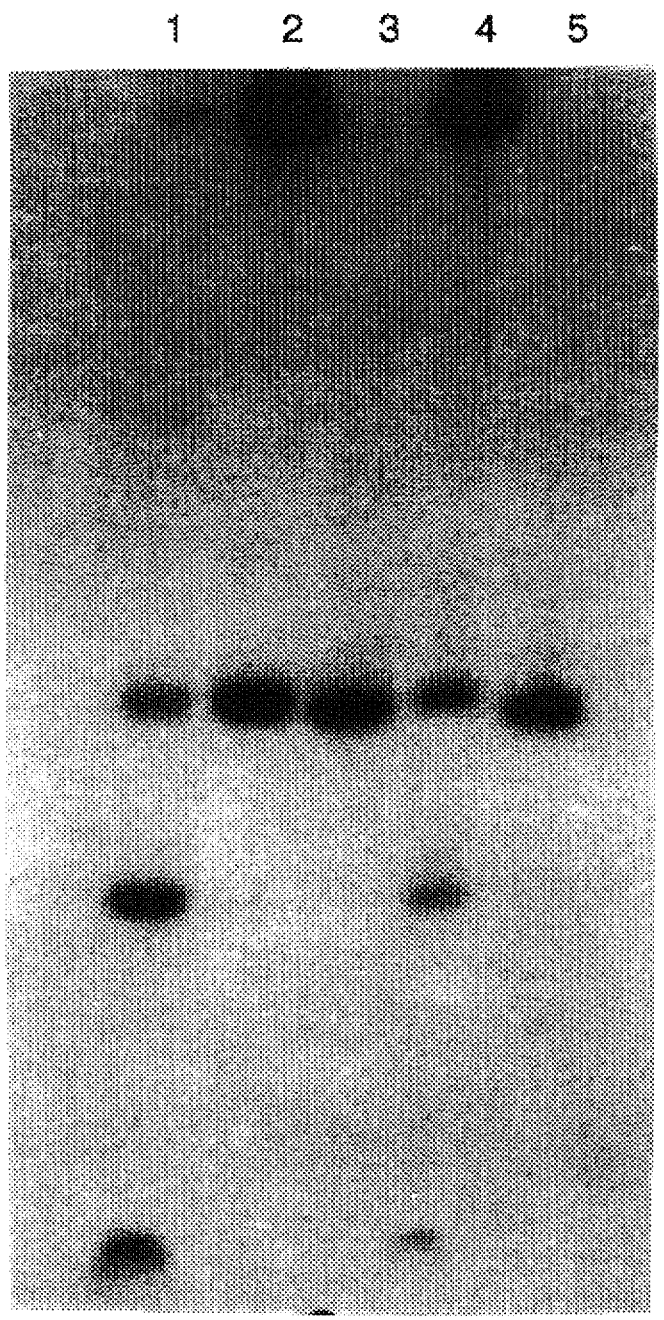

Substrate RNA

Substrate RNA

Substrate RNA

37° 30° 25° 20°

HIV 804

Substrate RNA

HIV 5366
Substrate RNA

Substrate RNA $K_m = 0.03 \mu M$ $k_{cat} = 7/min$

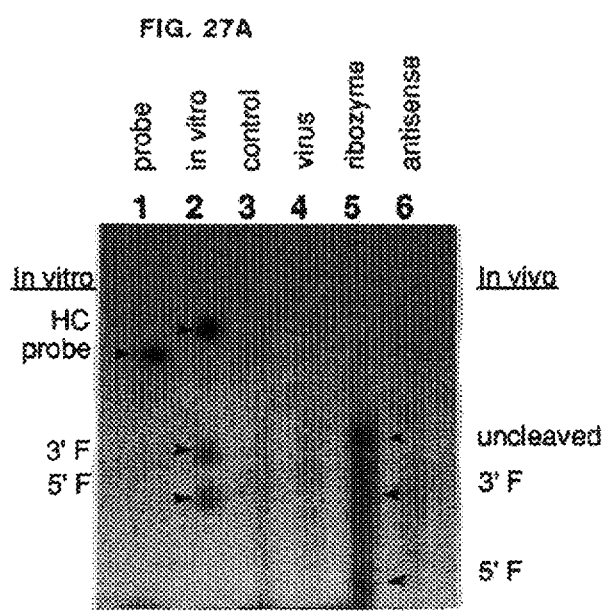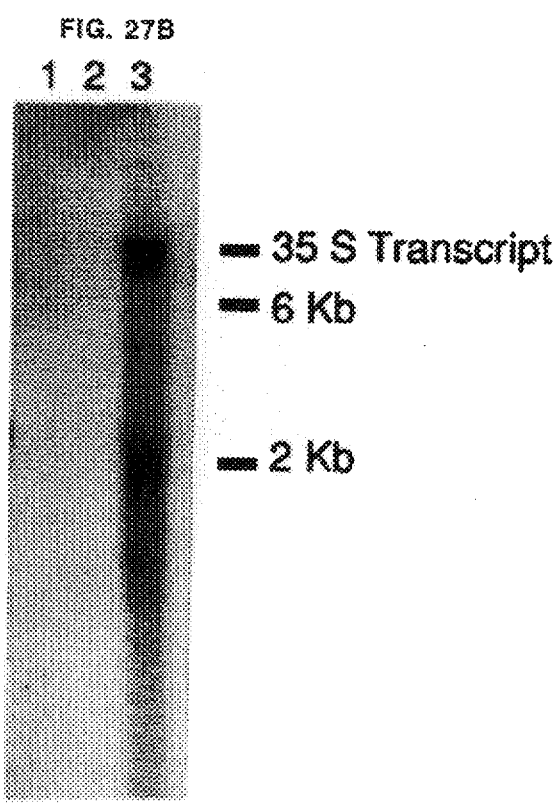

FIG. 29

|  |  |  |  |  |  |  |  |  | capsite: |  | LENGTH: |
|---|---|---|---|---|---|---|---|---|---|---|---|
| HIV-1 |  |  |  |  |  |  |  |  |  |  |  |
| HXB2 | cg | 561 | TG CCC GTC TGT TGT GT | 9645 | TG CCC GTC TGT TGT GT | 455, | 9539 | 9718 |
| HXB3 |  |  |  |  |  |  | ---- | 3156 |
| PV22 | cg | 570 | TG CCC GTC TGT TGT GT | 9688 | TG CCC GTC TGT TGT GT | 464, | 9582 | 9770 |
| SF2 | cg | 561 | TG CCC GTC TGT TGT GT | 9662 | TG CCC GTC TGT TGT GT | 455, | 9556 | 9737 |
| RF | cg | 75 | TG CCC GTC TGT TGT | | | ----, | 9091 | 9128 |
| MN | cg | 560 | TG CCC GTC TGT TaT GT | 9665 | TG CCC GTC TGT TaT GT | 454, | 9559 | 9738 |
| MAL | cg | 105 | TG CCC GTC aTC TGT TGT | | | 1, | 9134 | 9229 |
| ELI | cg | 107 | TG CCC GTC TGT TGT | | | 1, | 9079 | 9176 |
| NL43 | cg | 561 | TG CCC GTC TGT TGT GT | 9636 | TG CCC GTC TGT TGT GT | 455, | 9530 | 9709 |
| Z2 | cg | 561 | TG CCC GTC TGT TGT | | | 455, | ---- | 9081 |
| Z6 |  |  |  | 5012 | TG CCC GTC TGT TGT GT | ----, | 4906 | 5159 |
| CDC451-1 | cg | 559 | TG CCC GTC TGT TGT GT | | | 453, | ---- | 2438 |
| CDC451-2 |  |  |  |  |  |  | ---- | 3373 |
| ERVA |  |  |  |  |  |  | ---- | 3600 |
| BH5 |  |  |  |  |  |  | ---- | 5362 |
| BH8 |  |  |  |  |  |  | ---- | 3526 | 3563 |
| BH10 | cg |  |  |  |  |  | ---- | 8895 | 8932 |
| JH3-1 |  | 75 | TG CCC GTC TGT TGT GT | | | ----, | ---- | 1897 |
| JH3-2 |  |  |  |  |  |  | ---- | 2903 |
| NY5 |  |  |  |  |  |  | ---- | 2125 |
| PCV12 |  |  |  |  |  |  | 2207 | 2304 |
| POLMA |  |  |  |  |  |  | ---- | 861 |
| SC |  |  |  |  |  |  | 4250 | 4273 |
| WMJ2-1 |  |  |  |  |  |  | ---- | 1278 |
| WMJ2-2 |  |  |  |  |  |  | ---- | 2568 |
| Z-84 |  |  |  |  |  |  | ---- | 2653 |
| Z3 |  |  |  |  |  |  | ---- | 2709 |
| Z321 |  |  |  |  |  |  | 3420 | 3457 |

HIV-2 capsite sequence is (A/G)GT CGC TCT

| ROD | cg | ---- | ---- | 1, 9498 | 9671 |
| ISY | cg | ---- | ---- | 1, 9458 | 9636 |
| HIV2FG | cg | ---- | ---- | 1, 9255 | 9431 |

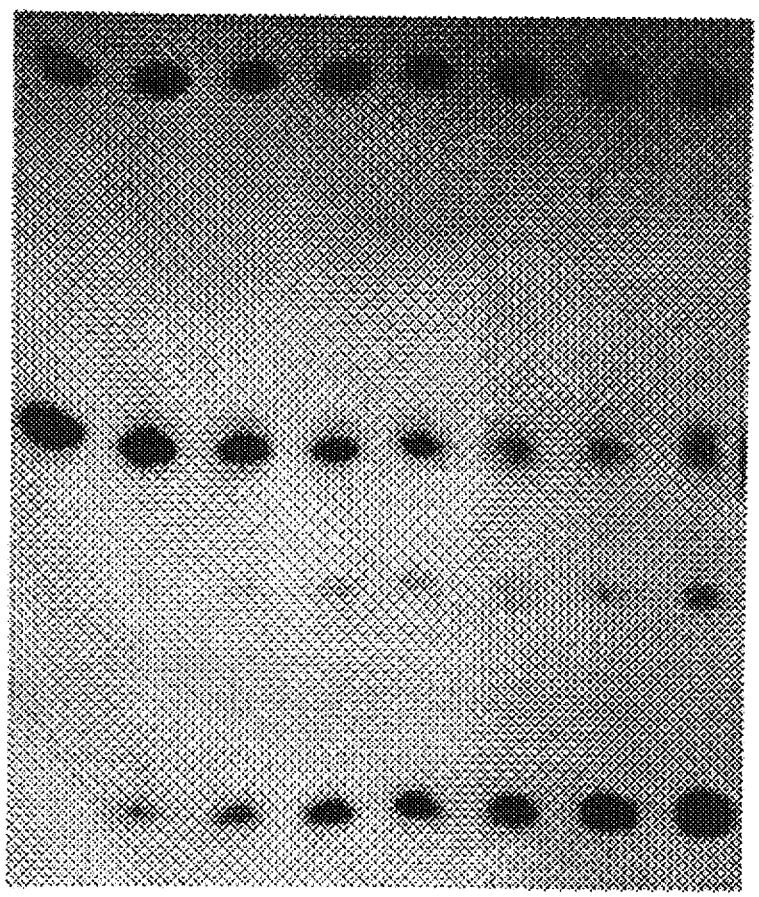

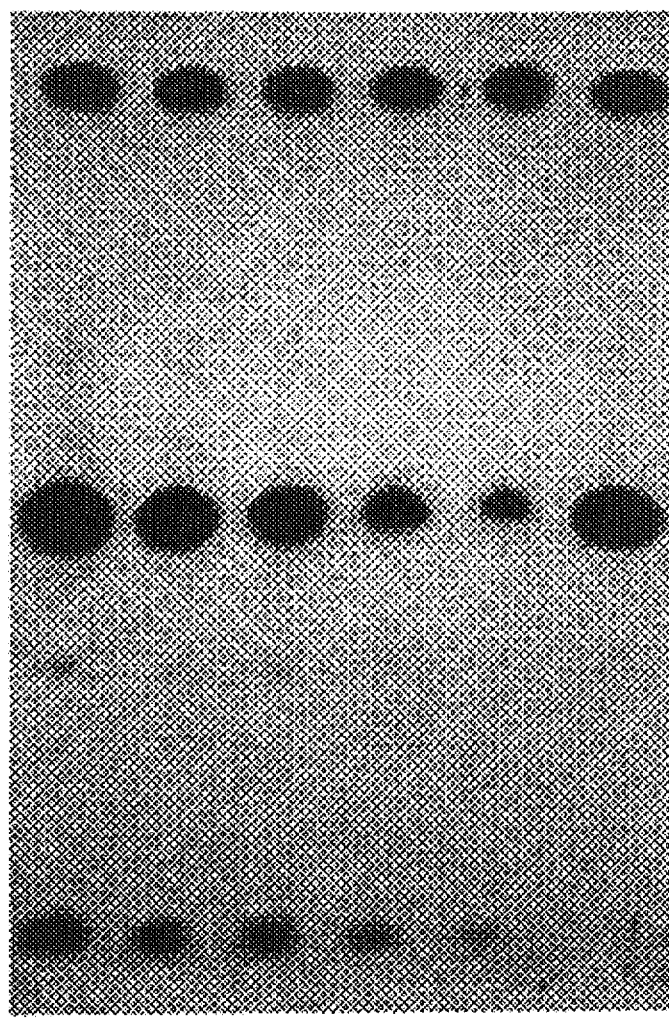

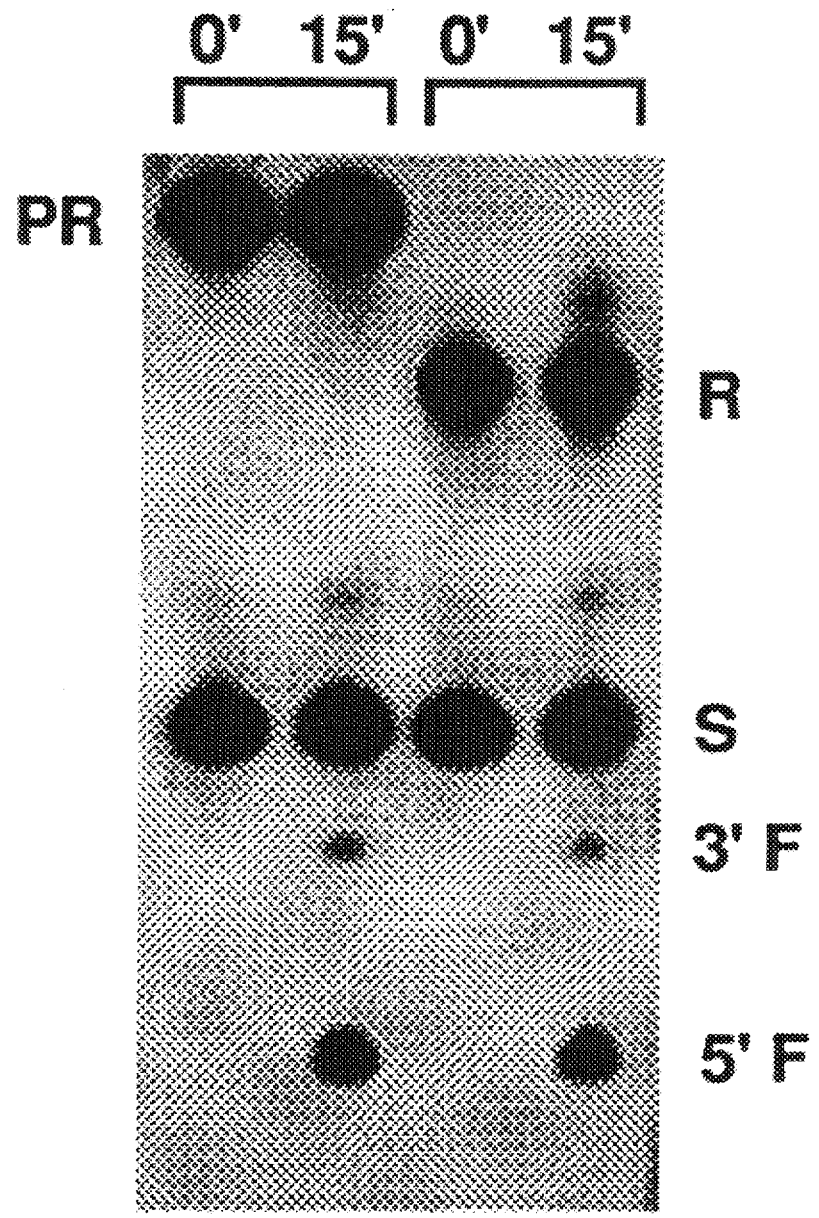

Selection of Cells With HGPRT Ribozyme

SEQUENCE LISTING ( 1 ) GENERAL INFORMATION:

( i i i ) NUMBER OF SEQUENCES: 90

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:1:

GGACUUCGGU CC                                                          1 2

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:2:

GACAGUCCUG                                                            1 0

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (ii) MOLECULE TYPE: RNA (genomic)

(xi) SEQUENCE DESCRIPTION: SEQ ID NO:3:

GUGACAGUCC UGUUU 15

(2) INFORMATION FOR SEQ ID NO:4:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:4:

AGAAACACAC GUU 13

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:5:

ACCAGAGAAA CACACGUUGU GGUAUAUUAC CUGGUA 36

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:6:

CACGGACUUC GGUCCGUG 18

(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:7:

ACCAGAGAAA CACACGGACU UCGGUCCGUG GUAUAUUACC UGGUA 45

(2) INFORMATION FOR SEQ ID NO:8:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:8:

TACCAGGTAA TATACCACAA CGTGTGTTTC TCTGGTTGAC TTCTCTGTTT CTATAGTGAG    60

TCGTATTA    68

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:9:

AAACAGGACT GTCACGCTAT AGTGAGTCGT ATTA    34

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:10:

GCGUGACAGU CCUGUUU    17

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:11:

GAAACAGUCC CCAAC    15

(2) INFORMATION FOR SEQ ID NO:12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:12:

GUUGGGAGAA GUUUACCAGA GAAACACACG UUGUGGUAUA UUACCUGGUA    50

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:13:

GUUUCAGUCA GUUGC    15

( 2 ) INFORMATION FOR SEQ ID NO:14:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:14:

GUUUCAGUCA GUUGCUC                                                            17

( 2 ) INFORMATION FOR SEQ ID NO:15:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:15:

GGGUUUCAGU CAGUUGCUCA A                                           21

( 2 ) INFORMATION FOR SEQ ID NO:16:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:16:

GGAATTCACC CGTCAGTTTT TAATACTGC                               29

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:17:

TGGATCCATT CTAGTATTTT GAGCTTCT                               28

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:18:

AUUCCGUCAU GGCGA                                                            15

( 2 ) INFORMATION FOR SEQ ID NO:19:

( i ) SEQUENCE CHARACTERISTICS:
        ( A ) LENGTH: 18 base pairs (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:19:

UUUCAGUCAG UUGCUCAA                                                              18

(2) INFORMATION FOR SEQ ID NO:20:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:20:

GCGUGACAGU CCUGUUUUUU U                                                          21

(2) INFORMATION FOR SEQ ID NO:21:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:21:

GCGUGACAGU CCUGUUUUUU UCGC                                                       24

(2) INFORMATION FOR SEQ ID NO:22:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:22:

GCGUGUCAGU CCUGUUU                                                               17

(2) INFORMATION FOR SEQ ID NO:23:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: RNA (genomic)

(xi) SEQUENCE DESCRIPTION: SEQ ID NO:23:

GCGUGAGAGU CCUGUUU                                                               17

(2) INFORMATION FOR SEQ ID NO:24:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: RNA (genomic)

( x i ) SEQUENCE DESCRIPTION: SEQ ID NO:24:

GAAACAGUCC CCAAC                                                                                   15

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:25:

GUUUCAGUCA GUUGC                                                                                   15

( 2 ) INFORMATION FOR SEQ ID NO:26:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:26:

GCGUUUCAGU CAGUUGCUCA A                                                                            21

( 2 ) INFORMATION FOR SEQ ID NO:27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:27:

GCGCCCCUGU CCCCGAG                                                                                 17

( 2 ) INFORMATION FOR SEQ ID NO:28:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:28:

GCGUGGGUGU CGACAUAGC                                                                               19

( 2 ) INFORMATION FOR SEQ ID NO:29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:29:

GCGUGACAGU CGUGUUU                                                                                 17

( 2 ) INFORMATION FOR SEQ ID NO:30:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:30:

GCGUGACAGU CAUGUUU    17

( 2 ) INFORMATION FOR SEQ ID NO:31:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:31:

GCGAGAGCGU CGGUAUUAA    19

( 2 ) INFORMATION FOR SEQ ID NO:32:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:32:

GCGAGAGCGU CGGUAUUAAG CGG    23

( 2 ) INFORMATION FOR SEQ ID NO:33:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:33:

GCGAGAGCGU CGGUAUUAAG C    21

( 2 ) INFORMATION FOR SEQ ID NO:34:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:34:

GCGUUUCUGU CGUUUAACU    19

( 2 ) INFORMATION FOR SEQ ID NO:35:

( i ) SEQUENCE CHARACTERISTICS:
    ( A ) LENGTH: 17 base pairs ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:35:

GCGUGACUGU CCUGUUU 17

( 2 ) INFORMATION FOR SEQ ID NO:36:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:36:

GCGUGACCGU CCUGUUU 17

( 2 ) INFORMATION FOR SEQ ID NO:37:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:37:

GCGUGACGGU CCUGUUU 17

( 2 ) INFORMATION FOR SEQ ID NO:38:

( i ) SEQUENCE CHARACTERISTICS:
                    ( A ) LENGTH: 21 base pairs
                    ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:38:

GCGUGCCCGU CUGUUGUGUG A 21

( 2 ) INFORMATION FOR SEQ ID NO:39:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:39:

GCGUGCCCGU CUGUUGUGU 19

( 2 ) INFORMATION FOR SEQ ID NO:40:

( i ) SEQUENCE CHARACTERISTICS:
                    ( A ) LENGTH: 17 base pairs
                    ( B ) TYPE: nucleic acid
                    ( C ) STRANDEDNESS: single
                    ( D ) TOPOLOGY: linear ( i i ) MOLECULE TYPE: RNA (genomic)

( x i ) SEQUENCE DESCRIPTION: SEQ ID NO:40:

GCGCCACUGU CGAUCGA                                                                                              17

( 2 ) INFORMATION FOR SEQ ID NO:41:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:41:

GCGCCACUGU CGAUCGAG                                                                                             18

( 2 ) INFORMATION FOR SEQ ID NO:42:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:42:

GCGAUUCCGU CAUGGCGA                                                                                             18

( 2 ) INFORMATION FOR SEQ ID NO:43:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:43:

GCGAUUCCGU CAUGGC                                                                                               16

( 2 ) INFORMATION FOR SEQ ID NO:44:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:44:

GCGAUGCGGU CACUCAUUA                                                                                            19

( 2 ) INFORMATION FOR SEQ ID NO:45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:45:

GCGAUGCGGU CACUCAU                                                                                              17

( 2 ) INFORMATION FOR SEQ ID NO:46:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:46:

GCGAUCCUGU CCAUUCAA        18

( 2 ) INFORMATION FOR SEQ ID NO:47:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:47:

GCGAUCCUGU CCAUUCAAG        19

( 2 ) INFORMATION FOR SEQ ID NO:48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:48:

GCGUUGGUGU CGACCUGAA        19

( 2 ) INFORMATION FOR SEQ ID NO:49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:49:

GCGACAGCGU CUGCUCC        17

( 2 ) INFORMATION FOR SEQ ID NO:50:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:50:

GCGUUGCGGU CGCUACG        17

( 2 ) INFORMATION FOR SEQ ID NO:51:

( i ) SEQUENCE CHARACTERISTICS:
        ( A ) LENGTH: 19 base pairs (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:51:

GCGUUGCGGU CGCUACGUC                                                                19

(2) INFORMATION FOR SEQ ID NO:52:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:52:

GCGUCUCAGU CACUAUG                                                                  17

(2) INFORMATION FOR SEQ ID NO:53:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:53:

GCGCACCUGU CACAUAA                                                                  17

(2) INFORMATION FOR SEQ ID NO:54:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:54:

GCGCACCUGU CACAUAAUU                                                                19

(2) INFORMATION FOR SEQ ID NO:55:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:55:

GCGUGGUGUC UGUGGA                                                                   16

(2) INFORMATION FOR SEQ ID NO:56:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: RNA (genomic)

( x i ) SEQUENCE DESCRIPTION: SEQ ID NO:56:

UGCCCGUCUG UUGUGU                                                                                          16

( 2 ) INFORMATION FOR SEQ ID NO:57:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:57:

AAACAGAGAA GUCAACCAGA GAAACACACG UUGUGGUAUA UUACCUGGUA                                                      50

( 2 ) INFORMATION FOR SEQ ID NO:58:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:58:

UGACAGUCCU GUUU                                                                                            14

( 2 ) INFORMATION FOR SEQ ID NO:59:

( i ) SEQUENCE CHARACTERISTICS:
    ( A ) LENGTH: 359 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:59:

UGGCCUACAC GAAAGGCCAG ACUACUCAGG CACUCCUGCU UUGUCCUGAC AGUCCACCGG          60
CUUUCGGUGG UGCAUUUGAU CACUUGGCAC GACGCAUCGC AUCCCAGAC GAUGGAGCAA          120
CCUCCACCUC UAACAUCGGA AGCACACCCG CGCCGCCACA UCGAUCAGUU CCGCAUGGUC         180
CAUUAUAUGG UGUUGCACAC AAAGAGACCA ACUGAAGAGA CAAACAACAC AGUAACCAAG        240
GGCCUAGAGC GUAAUCGCCG CUGCCCCAUA AGAGUAAGCU GUACCUUCAA ACUCUCUGGC        300
GCGGAGAUGU GAUACGCGCC GGCCCCGCUU AGGUUUAACA AGAUCGGGCU AUGGGACAG         359

( 2 ) INFORMATION FOR SEQ ID NO:60:

( i ) SEQUENCE CHARACTERISTICS:
    ( A ) LENGTH: 50 base pairs
    ( B ) TYPE: nucleic acid
    ( C ) STRANDEDNESS: single
    ( D ) TOPOLOGY: linear ( i i ) MOLECULE TYPE: RNA (genomic)

( x i ) SEQUENCE DESCRIPTION: SEQ ID NO:60:

AAACAGAGAA GUCAACCAGA GAAACACACG UUGUGGUAUA UUACCUGGUA                                                     50

( 2 ) INFORMATION FOR SEQ ID NO:61:

( i ) SEQUENCE CHARACTERISTICS:
    ( A ) LENGTH: 14 base pairs (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:61:

UGACUGUCCU GUUU                                                                                                      14

(2) INFORMATION FOR SEQ ID NO:62:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:62:

UGACCGUCCU GUUU                                                                                                      14

(2) INFORMATION FOR SEQ ID NO:63:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:63:

AAACAGAGAA CUCAACCAGA GAAACACACG UUGUGGUAUA UUACCUGGUA                                                                50

(2) INFORMATION FOR SEQ ID NO:64:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:64:

UGAGAGUCCU GUUU                                                                                                      14

(2) INFORMATION FOR SEQ ID NO:65:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: RNA (genomic)

(xi) SEQUENCE DESCRIPTION: SEQ ID NO:65:

GUUGGGAGAA GUUUACCAGA GAAACACACG UUGUGGUAUA UUACCUGGUA                                                                50

(2) INFORMATION FOR SEQ ID NO:66:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: RNA (genomic)

( x i ) SEQUENCE DESCRIPTION: SEQ ID NO:66:

AAACAGUCCC CAAC 14

( 2 ) INFORMATION FOR SEQ ID NO:67:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:67:

UUUCAGUCAG UUGCUC 16

( 2 ) INFORMATION FOR SEQ ID NO:68:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:68:

UUUCAGUCAG UUGC 14

( 2 ) INFORMATION FOR SEQ ID NO:69:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:69:

UUUCAGUCAG UUGCUCAA 18

( 2 ) INFORMATION FOR SEQ ID NO:70:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:70:

AGAGCGUCGG UAUUAA 16

( 2 ) INFORMATION FOR SEQ ID NO:71:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:71:

UGGGUGUCGA CAUA 14

( 2 ) INFORMATION FOR SEQ ID NO:72:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:72:

UGACAGUCCU GUUUUUUU         18

( 2 ) INFORMATION FOR SEQ ID NO:73:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:73:

NNNNNNAGAA NNNNACCAGA GAAACACACG UUGUGGUAUA UUACCUGGUA     50

( 2 ) INFORMATION FOR SEQ ID NO:74:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:74:

NNNNNGUCNN NNNN         14

( 2 ) INFORMATION FOR SEQ ID NO:75:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:75:

NNNNNNNUGA CAGUCCUGUU UCCUCCAAAC AGAGAAGUCA ACCAGAGAAA CACACGUUGU     60

GGUAUAUUAC CUGGUANNNN NNNNN     85

( 2 ) INFORMATION FOR SEQ ID NO:76:

( i ) SEQUENCE CHARACTERISTICS:
        ( A ) LENGTH: 133 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:76:

CTCGAGGGCC CGCGGCCGGC AGGCCTGGTA CCACGCGTGA CAGTCCTGTT TCCTCCAAAC     60

AGAGAAGTCA ACCAGAGAAA CACACGTTGT GGTATATTAC CTGGTAGTCG AGGGATCTTT     120

GTGAAGGAAC CTT     133

( 2 ) INFORMATION FOR SEQ ID NO:77:

( i ) SEQUENCE CHARACTERISTICS:
        ( A ) LENGTH: 161 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:77:

```
GGGAAAGCTT GCATGCCTGC AGGTCGACTA CCAGGTAATA TACCACAACG TGTGTTTCTC      60
TGGTTGACTT CTCTGTTTGG AGGAAACAGG ACTGTCACGC GTGGTACCAG GCCTGCCGGC     120
CGCGGGCCCT CGAGGGATCC CCGGGTACCG AGCTCGAATT C                         161
```

( 2 ) INFORMATION FOR SEQ ID NO:78:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:78:

```
TGCCCGTCTG TTGTGT                                                      16
```

( 2 ) INFORMATION FOR SEQ ID NO:79:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:79:

```
TGCCCGTCTG TTGT                                                        14
```

( 2 ) INFORMATION FOR SEQ ID NO:80:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:80:

```
TGCCCGTCTG TTATGT                                                      16
```

( 2 ) INFORMATION FOR SEQ ID NO:81:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:81:

```
TGCCCATCTG TTGT                                                        14
```

( 2 ) INFORMATION FOR SEQ ID NO:82:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:82:

```
GGGAGUCACA  CAACAAGAAG  GCAACCAGAG  AAACACACGU  UGUGGUAUAU  UACCUGGUA         59
```

( 2 ) INFORMATION FOR SEQ ID NO:83:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:83:

```
GCGUGCCCGU  CUGUUGUGU                                                         19
```

( 2 ) INFORMATION FOR SEQ ID NO:84:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:84:

```
GGGAATTCGA  GCTCGGTACC  CGGGGATCCC  TCGAGGATCC  ACACAACAAG  AAGGCAACCA         60
GAGAAACACA  CGTTGTGGTA  TATTACCTGG  TACGCGTGAC  AGTCCTGTTT  CCTCCAAACA        120
GAGAAGTCAA  CCAGAGAAAC  ACACGTTGTG  GTATATTACC  TGGTAGTCGA  CCTGCAGGCA        180
TGCAAGCTT                                                                    189
```

( 2 ) INFORMATION FOR SEQ ID NO:85:

( i ) SEQUENCE CHARACTERISTICS:
        ( A ) LENGTH: 159 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:85:

```
CCCGGGGATC  CCTCGAGGAT  CCACACAACA  AGAAGGCAAC  CAGAGAAACA  CACGTTGTGG         60
TATATTACCT  GGTACGCGTG  ACAGTCCTGT  TTCCTCCAAA  CAGAGAAGTC  AACCAGAGAA        120
ACACACGTTG  TGGTATATTA  CCTGGTAGTC  GACCTCGAG                                 159
```

( 2 ) INFORMATION FOR SEQ ID NO:86:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:86:

| | | | | | |
|---|---|---|---|---|---|
| GCTAGCCCGG | GGATCCTCGC | CATAGAAGAA | TACCAGAGAA | ACACACGTTG | TGGTATATTA | 60
| CCTGGTACGC | GTGACAGTCC | TGTTTCCTCC | AAACAGAGAA | GTCAACCAGA | GAAACACACG | 120
| TTGTGGTATA | TTACCTGGTA | GTCGACCTCG | AGG | | | 153

( 2 ) INFORMATION FOR SEQ ID NO:87:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:87:

| | | | | | |
|---|---|---|---|---|---|
| CCCGGGGATC | CTTGAGCAAC | TAGAAGAAAA | CCAGAGAAAC | ACACGTTGTG | GTATATTACC | 60
| TGGTAACGCG | TGACAGTCCT | GTTCCTCCA | AACAGAGAAG | TCAACCAGAG | AAACACACGT | 120
| TGTGGTATAT | TACCTGGTAG | TCGACCTCGA | | | | 150

( 2 ) INFORMATION FOR SEQ ID NO:88:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:88:

| | | | | | |
|---|---|---|---|---|---|
| NNNNNNAGA | ASNNNACCAG | AGAAACACAC | GUUGUGGUAU | AUUACCUGGU | A | 51

( 2 ) INFORMATION FOR SEQ ID NO:89:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:89:

| | |
|---|---|
| NNNSNGUCNN | NNNNN | 15

( 2 ) INFORMATION FOR SEQ ID NO:90:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:90:

| | |
|---|---|
| CACGGACUUC | GGUCCGUG | 18

HAIRPIN RIBOZYMES

This application is a divisional of U.S. Ser. No. 08/078, 774, filed Jun. 17, 1993 which was a continuation of U.S. Ser. No. 07/703,427, filed May 14, 1991, now abandoned, which was a continuation-in-part of U.S. Ser. No. 07/577, 658, filed Sep. 4, 1990, now abandoned, which was a continuation-in-part of U.S. Ser. No. 07/409,666, filed Sep. 20, 1989, now abandoned, which was a continuation-in-part of U.S. Ser. No. 07/247,100, filed Sep. 20, 1988, now abandoned. The contents of all of which are hereby incorporated by reference into the subject application.

This invention was made in part with Government support under Grant No. DMB 8817576 awarded by the National Science Foundation and Grant No. RO1 AI 29870 awarded by the National Institutes of Health. The Government has certain rights in the invention.

FIELD OF THE INVENTION

The present invention relates to an RNA catalyst which cleaves specific RNA sequences into a fragment having a 5' hydroxyl and a fragment having a 2',3' cyclic phosphate. The products of the reaction described herein resemble those resulting from the natural hydrolysis of RNA.

BACKGROUND OF THE INVENTION

Certain naturally occurring satellite, virusoid and viroid RNAs possess the property of self-catalyzed cleavage. Self-cleavage has been demonstrated in vitro for avocado sunblotch viroid (ASBV) (Hutchins, C. J., Rathjen, P. D., Forster, A. C. and Symons, R. H. (1986) *Nucleic Acids Res.*, 14: 3627–3640), satellite RNA from tobacco ringspot virus (sTRSV) (Prody, G. A., Bakos, J. T., Buzayan, J. M., Schneider, I. R. and Bruening, G. (1986) *Science*, 231: 1577–1580; Buzayan, J. M., Gerlach, W. L. and Bruening, G. B. (1986) *Proc. Natl. Acad. Sci. U.S.A.* 83: 8859–8862) and lucerne transient streak virus (VLTSV) (Forster, A. C. and Symons, R. H. (1987) *Cell*, 49: 211–220). These self-catalyzed RNA cleavage reactions share a requirement for divalent metal ions and neutral or higher pH and cleave target RNA sequences to give 5' hydroxyl and 2',3'-cyclic phosphate termini (Prody, G. A., Bakos, J. T., Buzayan, J. M., Schneider, I. R. and Bruening, G. (1986) *Science*, 231: 1577–1580; Forster, A. C. and Symons, R. H. (1987) *Cell*, 49: 211–220; Epstein, L. M. and Gall, J. G. (1987) *Cell*, 48: 535–543; Buzayan, J. M. Gerlach, W. L., Bruening, G. B., Keese, P. and Gould, A. R. (1986) Virology, 151: 186–199).

A "hammerhead" model has been proposed and accurately describes the catalytic center of (+) sTRSV RNA, the (+) and (−) strands of ASBV and the (+) and (−) strands of vLTSV (Forster, A. C. and Symons, R. H. (1987) *Cell*, 49: 211–220). The single exception is (−) sTRSV RNA which does not fit the "hammerhead" model (Forster, A. C. and Symons, R. H. (1987) *Cell*, 49: 211–220; Buzayan, J. M., Gerlach, W. L. and Bruening, G. (1986) *Nature*, 323: 349–352; Buzayan, J. M., Hampel, A. and Bruening, G. B. (1986) *Nucleic Acids Res.*, 14: 9729–9743), and the structure of whose catalytic center was unknown prior to the present invention. It is therefore understandable that the primary scientific focus has been on studying the "hammerhead" consensus structure and, as regards sTRSV, on studying the (+) strand.

Intermolecular cleavage of an RNA substrate by an RNA catalyst that fits the "hammerhead" model was first shown in 1987 (Uhlenbeck, O. C. (1987) *Nature*, 328: 596–600). The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences (Haseloff and Gerlach, *Nature*, 334, 585 (1988); Walbot and Bruening, *Nature*, 334, 196 (1988); Uhlenbeck, O. C. (1987) *Nature*, 328: 596–600; Koizumi, M., Iwai, S. and Ohtsuka, E. (1988) *FEBS Lett.*, 228: 228–230). This has allowed use of the catalytic RNA to cleave specific target sequences and indicates that catalytic RNAs designed according to the "hammerhead" model may possibly cleave specific substrate RNAs in vivo. (see Haseloff and Gerlach, *Nature*, 334, 585 (1988); Walbot and Bruening, *Nature*, 334, 196 (1988); Uhlenbeck, O. C. (1987) *Nature*, 328: 596–600).

However, catalytic RNAs such as those that were designed based on the "hammerhead" model have several limitations which restrict their use in vitro and may forestall their use in vivo. For example, the temperature optimum for the reaction is 50°–55° C., which is well above physiological, and the kcat (turnover number) is only 0.5/min even at 55° C. (Uhlenbeck, O. C. (1987) *Nature*, 328:596–600; Haseloff and Gerlach, *Nature*, 334, 585 (1988)). In addition, the Km is 0.6 uM (Uhlenbeck, O. C. (1987) *Nature*, 328:596–600), meaning that the reaction requires high concentrations of substrate which makes it difficult, if not impossible, for the catalytic RNA to cleave low levels of target RNA substrate such as would be encountered in vivo.

Cech et al. published application WO 88/04300 and U.S. Pat. No. 4,987,071 also report the preparation and use of certain synthetic ribozymes that have several activities, including endoribonuclease activity. The design of these ribozymes is based on the properties of the Tetrahymena ribosomal RNA self-splicing reaction. A temperature optimum of 50° C. is reported (page 39 of WO 88/04300; col. 20, lines 4–5, of U.S. Pat. No. 4,987,071) for the endoribonuclease activity, and the Km and kcat reported for this activity are 0.8 uM and 0.13/minute, respectively (Example VI, last paragraph).

In view of the above, there is a need for an RNA catalyst having a lower temperature optimum, preferably near physiological temperatures, a higher turnover number and a smaller Km and which can be engineered to cut specific target RNA substrates. Accordingly, based on the discovery of a totally different structure disclosed hereinafter, it is an object of the present invention to provide such an RNA catalyst. Other objects and features of the invention will be in part apparent and in part pointed out. The invention, accordingly, comprises the products and methods hereinafter described and their equivalents, the scope of the invention being indicated in the appended claims.

SUMMARY OF THE INVENTION

The invention comprises a synthetic RNA catalyst capable of cleaving an RNA substrate which contains the sequence:

5'-$F_1$-CS-$F_2$-3', wherein,

CS is a cleavage sequence; and $F_1$ and $F_2$ each is a sequence of bases flanking the cleavage sequence.

The catalyst comprises a substrate binding portion and a "hairpin" portion. The substrate binding portion of the catalyst has the sequence:

3'-$F_4$-$L_1$-$F_3$-5' wherein, $F_3$ is a sequence of bases selected so that $F_3$ is substantially base paired with $F_2$ when the catalyst is bound to the substrate;

$F_4$ is a sequence of bases selected so that $F_4$ is substantially base paired with $F_1$ when the catalyst is bound to the substrate;

the sequences of $F_3$ and $F_4$ being selected so that each contains an adequate number of bases to achieve sufficient binding of the RNA substrate to the RNA catalyst so that cleavage of the substrate can take place; and $L_1$ is a sequence of bases selected so that $L_1$ does not base pair with CS when the catalyst is bound to the substrate.

The "hairpin" portion is a portion of the catalyst that assumes a hairpin-like configuration when the substrate-catalyst complex is modeled in two dimensions for minimum energy folding. The "hairpin" portion of the catalyst preferably has the sequence:

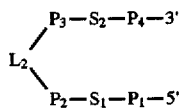

wherein, $P_1$ and $P_4$ each is a sequence of bases, the sequences of $P_1$ and $P_4$ being selected so that $P_1$ and $P_4$ are substantially base paired;

$P_1$ is covalently attached to $F_4$;

$S_1$ and $S_2$ each is a sequence of bases, the sequences of $S_1$ and $S_2$ being selected so that $S_1$ and $S_2$ are substantially unpaired;

$P_2$ and $P_3$ each is a sequence of bases, the sequences of $P_2$ and $P_3$ being selected so that $P_2$ and $P_3$ are substantially base paired; and $L_2$ is a sequence of unpaired bases.

RNA catalysts according to the invention can cleave substrates of any length or type as long as they contain an appropriate cleavage sequence. In particular, the catalysts can be used to cleave a specific sequence in naturally-occurring RNA having a cleavage sequence, as well as RNAs which have been engineered to contain a cleavage sequence.

The invention further comprises an engineered DNA molecule and a vector, each of which comprises a DNA sequence that codes for an RNA catalyst according to the invention. The invention also comprises a host transformed with the vector, the host being capable of expressing the RNA catalyst. In particular, hosts can be transformed with vectors that, when transcribed, will produce RNA catalysts which can cleave any RNA, native or foreign, found in the host. For example, hosts can be transformed with vectors that, when transcribed, produce RNA catalysts which can regulate the expression of genes by cleaving messenger RNA or which act as anti-viral agents by cleaving viral RNA. Thus, the invention has application in vitro and in vivo in prokaryotes and eukaryotes of plant or animal origin in regulating gene expression and for controlling viral infections.

Finally, the invention includes a method of cleaving an RNA substrate comprising contacting the substrate with an RNA catalyst according to the invention. The reaction is unique because it occurs under physiological conditions, having a temperature optimum near 37° C., with very favorable reaction parameters. The method can be practiced in vitro or in vivo. For instance, the method may be practiced in vivo in host cells that have been transformed with a vector that codes for an RNA catalyst according to the invention.

BRIEF DESCRIPTION OF THE DRAWINGS

FIGS. 6A–6B shows the dependence of the rate of reaction on concentration of catalytic RNA.

FIGS. 12A–12B shows that different target RNA sequences can be used as long as the base pairing with the catalytic RNA in the regions flanking the cleavage sequence is maintained (SEQ ID NO 63,64).

FIGS. 14A–C also show the separation patterns on acrylamide gels of the reaction products obtained by reacting these substrates with catalytic RNAs designed to base pair with the substrates in the regions flanking the AGUC cleavage sequence (SEQ ID NO 67);(SEQ ID NO 69).

FIGS. 15A–15C also shows the separation patterns on acrylamide gels of the reaction products obtained by reacting this substrate with a catalytic RNA designed to base pair with the substrate in the regions flanking the CGUC cleavage sequence of the substrate.

FIGS. 16A–16B also shows the separation patterns on an acrylamide gel of the reaction products obtained by reacting this substrate with a catalytic RNA designed to base pair with the substrate in the regions flanking the UGUC cleavage sequence of the substrate (SEQ ID NO 72).

FIGS. 17A–17B also shows the separation patterns on an acrylamide gel of the reaction products obtained by reacting this substrate with different concentrations of a catalytic RNA designed to base pair with the substrate in the regions flanking the cleavage sequence of the substrate, including with the four non-native U's.

FIGS. 19A–19B also shows the separation patterns on acrylamide gels of the reaction products obtained by reacting the various catalytic RNAs with substrate RNA S17.

FIGS. 20A–20B also shows the separation pattern on an acrylamide gel of the reaction products obtained when this catalyst was transcribed and cleaved autocatalytically.

FIGS. 21A–21B also shows the separation patterns on acrylamide gels of the reaction products obtained by reacting these catalysts or catalyst R51 (control gel) with substrate S17.

FIG. 27A: Shows the results of S1 nuclease protection assay of RNA from infected turnip plants and RNA controls.

FIG. 27B: Results of Northern blot analysis of the RNA isolated from control and infected plants.

FIG. 29: Conservation of the HIV-1 target sequence in various HIV isolates (SEQ ID NOS 78–81).

FIGS. 31A–31B and 32A–32B: Results of the cleavage of SHIV substrate RNA by RHIV catalytic RNA.

FIG. 35: Results of cleavage of substrate SHIV by RHIV and by catalytic RNA produced by T7 RNA polymerase transcription of pHR.

DETAILED DESCRIPTION OF THE DRAWINGS

Figure 1:
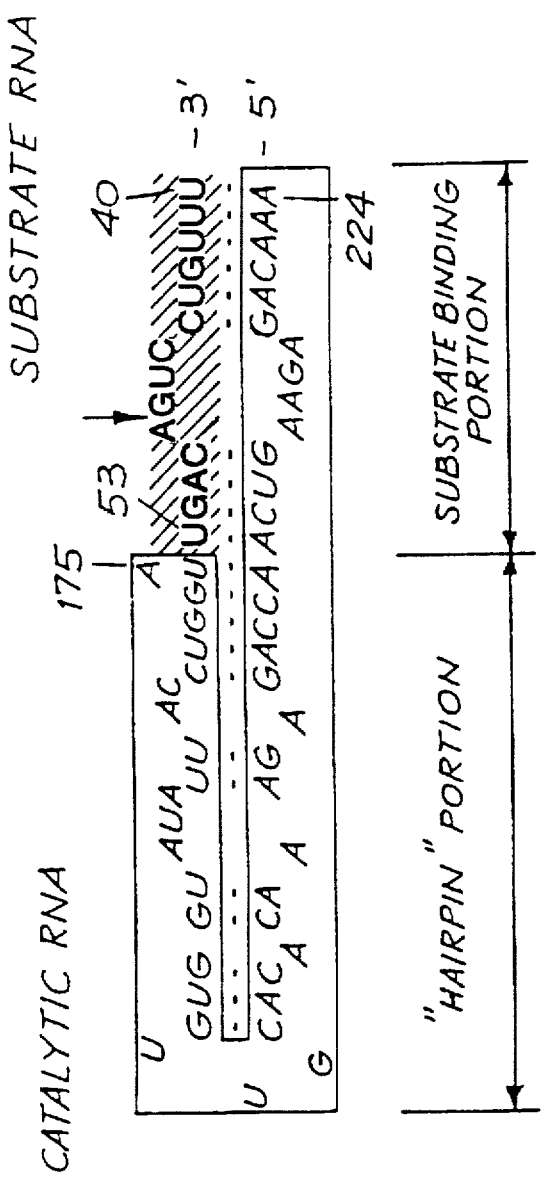
FIG. 1 shows the (−) sTRSV RNA substrate-catlyst complex (SEQ ID NO 57); (SEQ ID NO 58) that fits the "hairpins" model of catalytic RNA in accordance with the present invention.

FIG. 1. The "hairpin" model for RNA catalysis was developed by determining the minimum energy folding predicted by computer modeling of the catalytic complex containing the minimum size catalytic RNA and substrate RNA of (−)sTRSV RNA. It is this minimum energy folding which is shown in FIG. 1. Two molecules are shown folded: (1) catalytic RNA which contains 50 bases of satellite RNA (224–175) and (2) substrate RNA which contains 14 bases of satellite RNA (53–40). The arrow represents the site of cleavage.

The 50-base catalytic RNA and the 14-base substrate RNA are the "minimum size" in the sense that reductions in their length result in a substantial or total loss of catalytic activity as is shown in the Examples below. Thus, this length of (−)sTRSV catalyst sequence is preferred to shorter lengths. Also, substrate RNA having at least the degree of base-pairing with the catalyst exhibited by the 14-base substrate is preferred.

Figure 2:
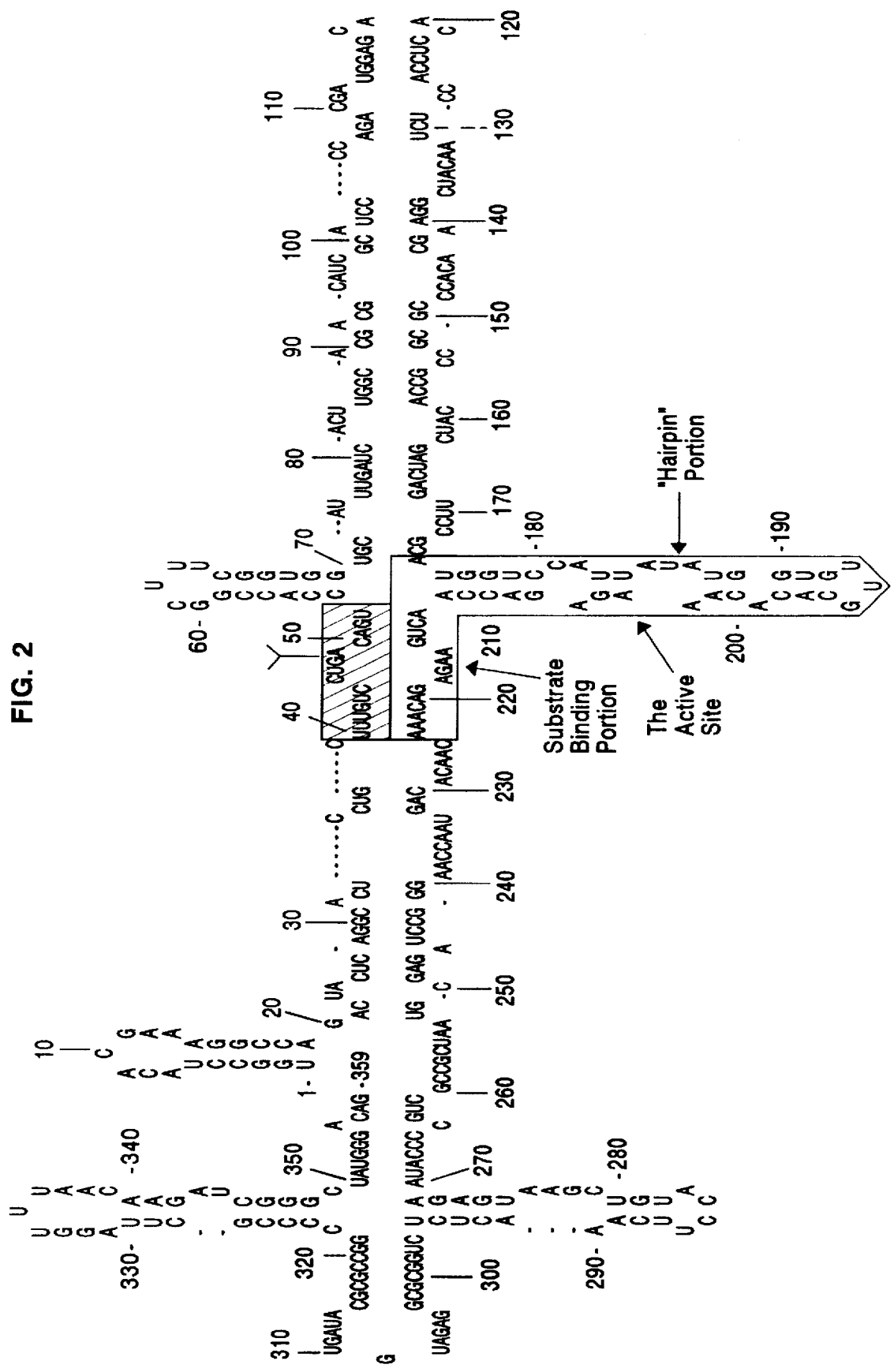
FIG. 2 shows minimum energy folding of (−) sTRSV RNA (SEQ ID NO 59).

FIG. 2. Minimum energy folding of (−)sTRSV RNA. The molecule was folded using the Wisconsin RNA folding program (Zucker, M. and Stiegler, P. (1981) Nucleic Acids Res., 9: 133–148; Devereux, J., Haeberli, P. and Smithies, O. (1984) Nucleic Acids Res., 12: 387–395) with base numbers corresponding to (+)sTRSV (Buzayan, J. M., Gerlach, W. L., Bruening, G. B., Keese, P. and Gould, A. R. (1986) Virology, 151: 186–199). With this numbering scheme the 5'–3' direction of the molecule is with decreasing base number. The minimum catalytic complex is identified. The substrate RNA sequence is between bases 53–40 and the catalytic RNA sequence is between bases 224–175. The arrow is the site of cleavage.

The folding identifies regions of expected base pairing and expected non-base pairing, loops. This model does not preclude higher order interactions occurring between the loops.

Figure 3A:
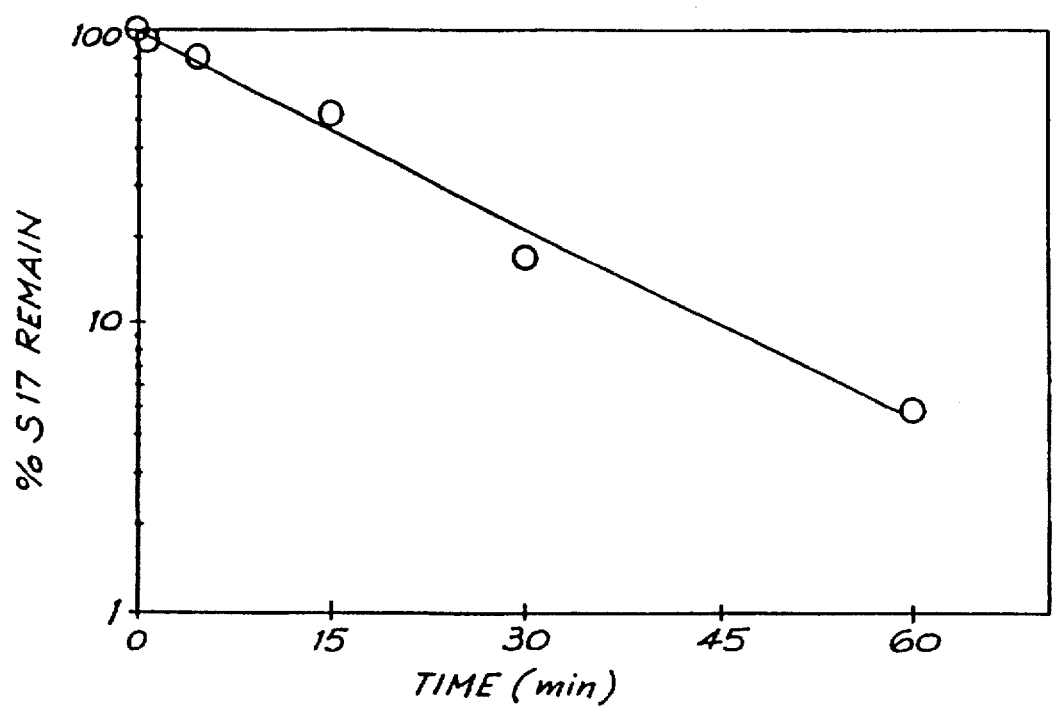
FIGS. 3A–3B shows the time course of catalysis of a substrate RNA by the catalytic RNA.
Figure 3B:
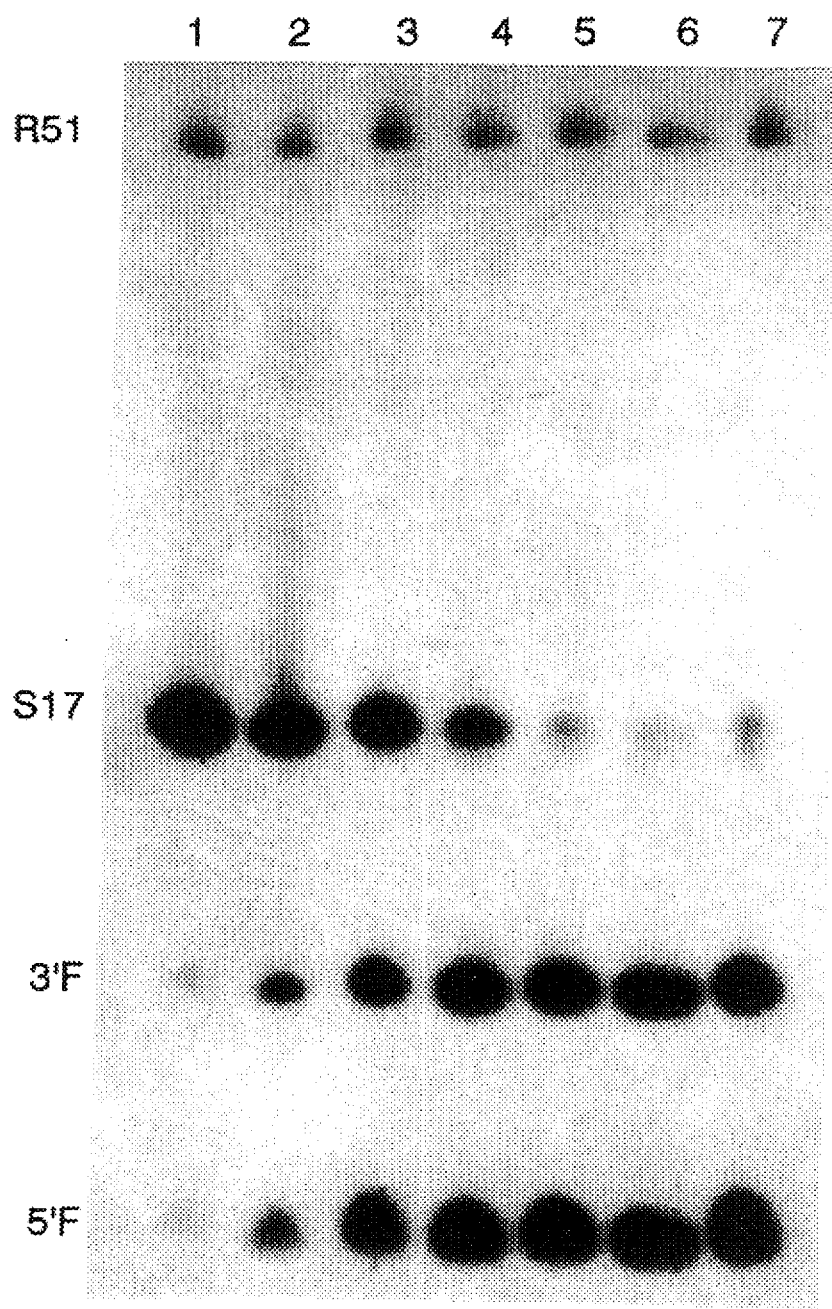

FIGS. 3A–3B. Time course of substrate S17 cleavage by catalytic RNA R51. The reaction was carried out under standard conditions, which were 37° C. in 12 mM MgCl₂, 40 mM Tris pH 7.5 and 2 mM spermidine, for the following times: lane 1, 30 sec; lane 2, 5 min; lane 3, 15 min; lane 4, 30 min; lane 5, 60 min; lane 6, 90 min; lane 7, 150 min. Concentrations were as follows: [R51]=0.0032 uM and [S17]=0.09 uM. RNA was separated on 7M urea, 20% acrylamide gels, bands cut out and counted in the liquid scintillation counter for FIGS. 3A–17B and 19A–21B. Throughout the figures, the designations 5'F and 3'F are the products of cleavage of the substrate and represent the resulting 5' fragments and 3' fragments, respectively.

Figure 4A:
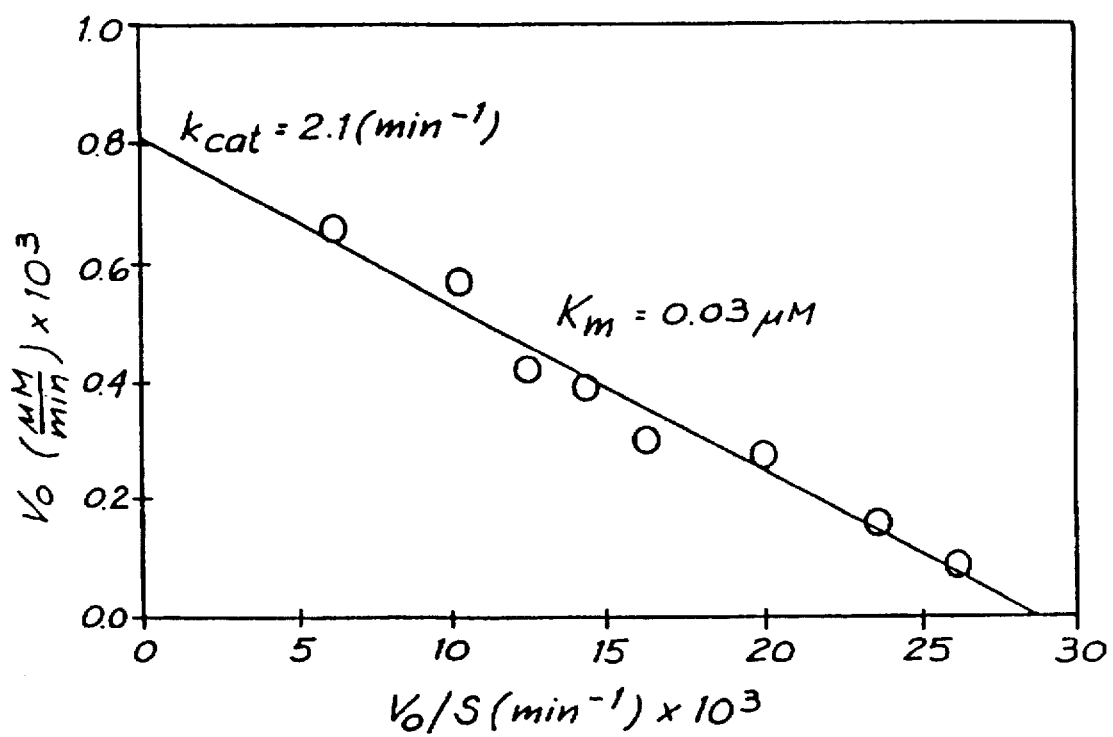
FIGS. 4A–4B shows the Michaelis-Menten kinetics of the RNA catalytic reaction.
Figure 4B:
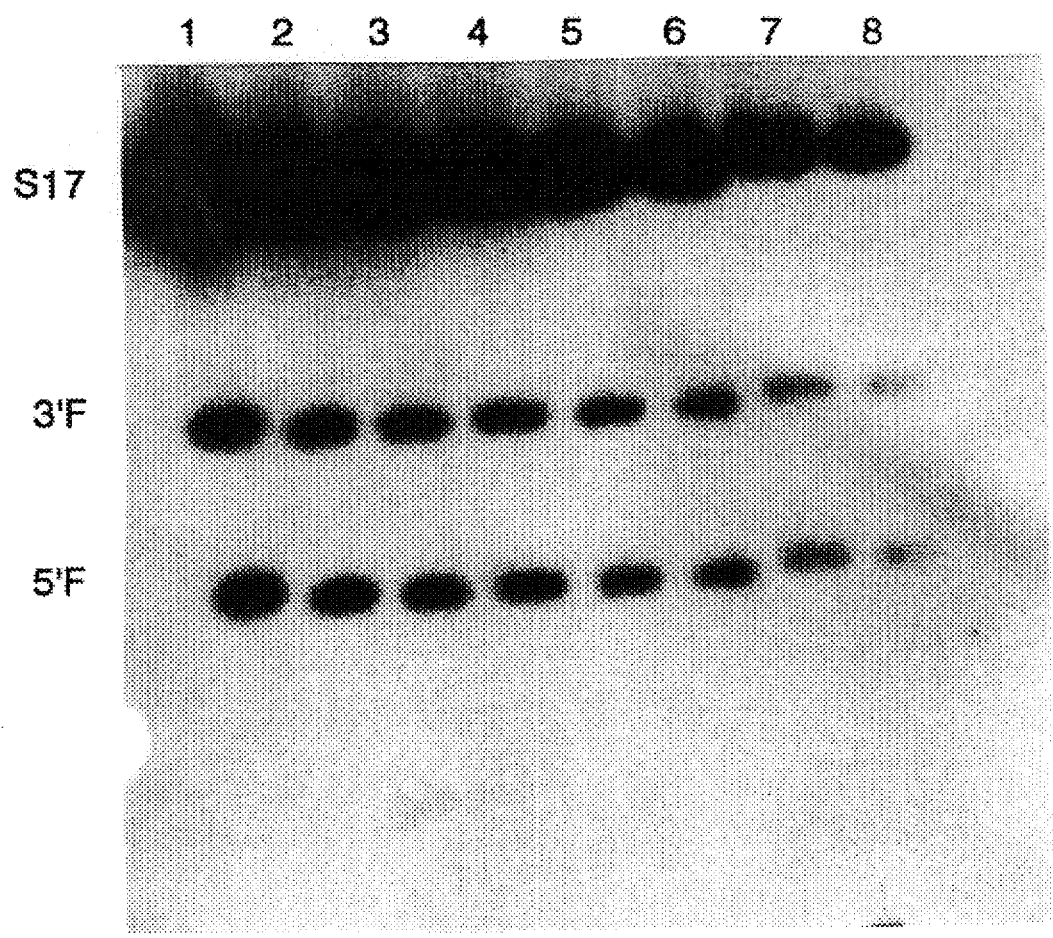

FIGS. 4A–4B. Eadie Hofstee plot of catalytic RNA R51 cleavage of substrate RNA S17. The reaction was carried out at 37° C. in 12 mM MgCl₂, 40 mM Tris pH 7.5 and 2 mM spermidine. Concentrations were as follows: [R51]=0.0004 uM and [S17]=0.125 uM (lane 1), 0.0625 uM (lane 2), 0.0417 uM (lane 3), 0.031 uM (lane 4), 0.021 uM (lane 5), 0.0156 uM (lane 6), 0.0078 uM (lane 7) and 0.0039 uM (lane 8).

Figure 5A:
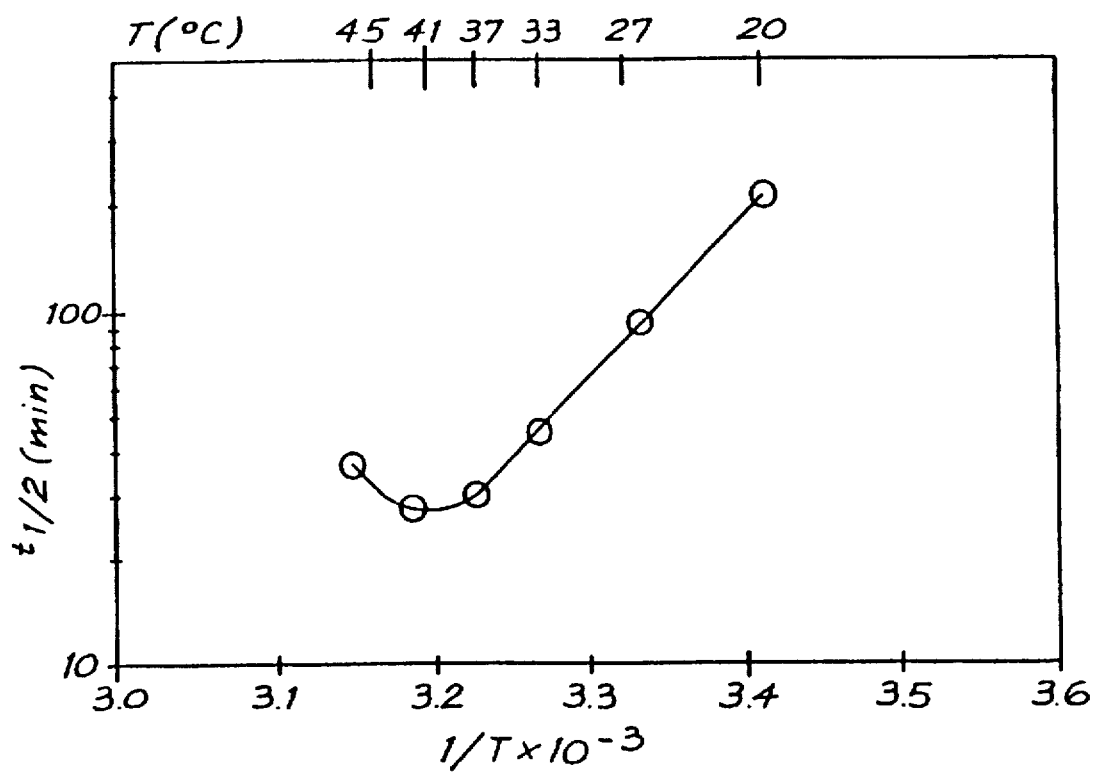
FIGS. 5A–5B shows the temperature dependence of the RNA catalytic reaction.
Figure 5B:
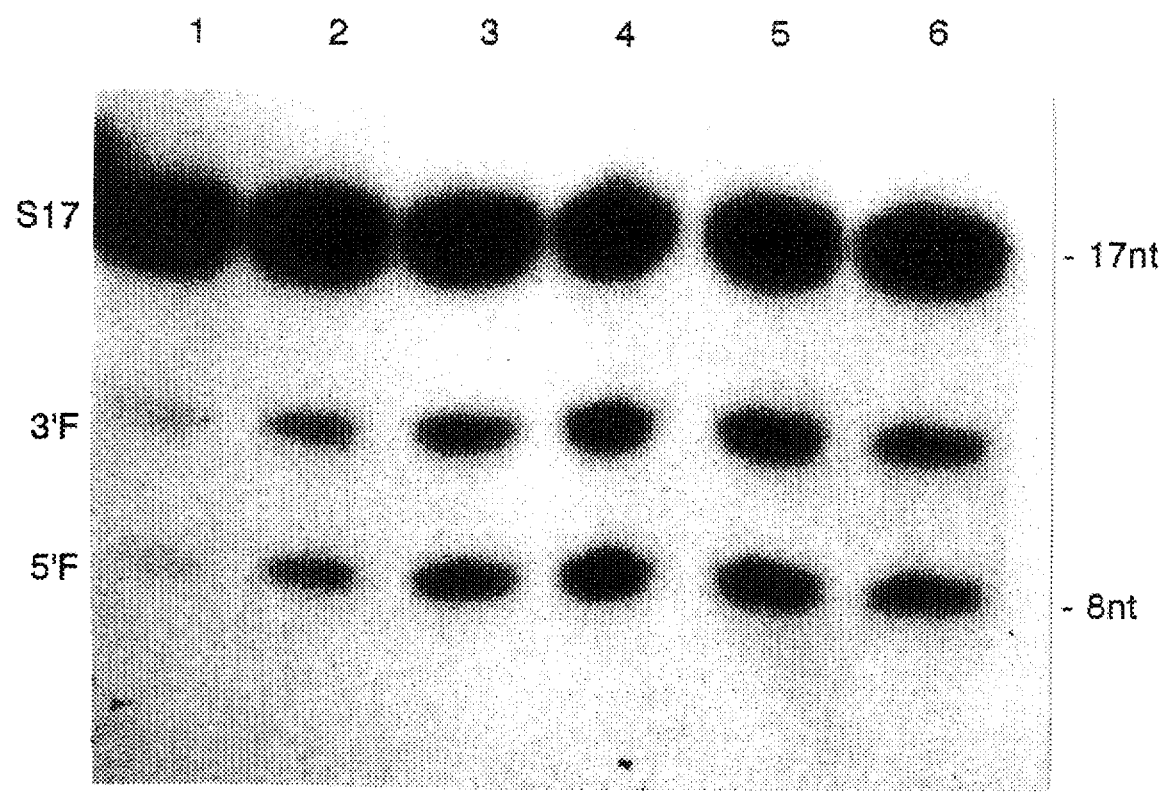

FIGS. 5A–5B. Temperature dependence of the rate of cleavage of substrate RNA S17 by catalytic RNA R51. The reaction was carried out in 12 mM MgCl₂, 40 mM Tris pH 7.5 and 2 mM spermidine at 45° C. (lane 6), 41° C. (lane 5), 37° C. (lane 4), 33° C. (lane 3), 27° C. (lane 2) and 20° C. (lane 1). The concentrations used were: [R51]=0.003 uM and [S17]=0.09 uM. R51 was unlabeled. The velocities shown in the graph in FIGS. 5A–5B were calculated by the use of time points of 8 and 16 minutes. The separation patterns of the reaction products on the acrylamide gel shown in the figure are for the 16-minute time point.

Figure 6A:
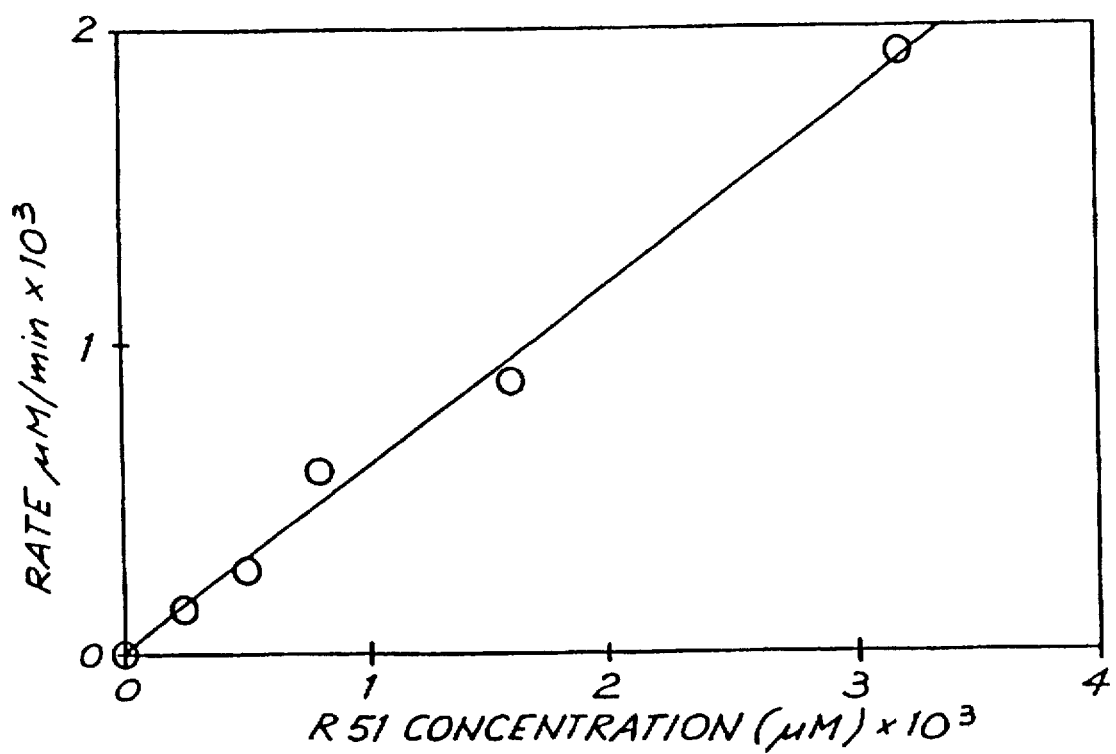

FIGS. 6A–6B. Rate of cleavage of substrate RNA S17 at varying concentrations of catalytic RNA R51. The reaction was carried out at 37° C. in 12 mM MgCl₂, 40 mM Tris pH 7.5 and 2 mM spermidine for 40 min (lane 1 and 2), 20 min (lane 3), 10 min (lane 4) and 5 min (lane 5). The concentration of substrate used was 0.175 uM.

Figure 7:
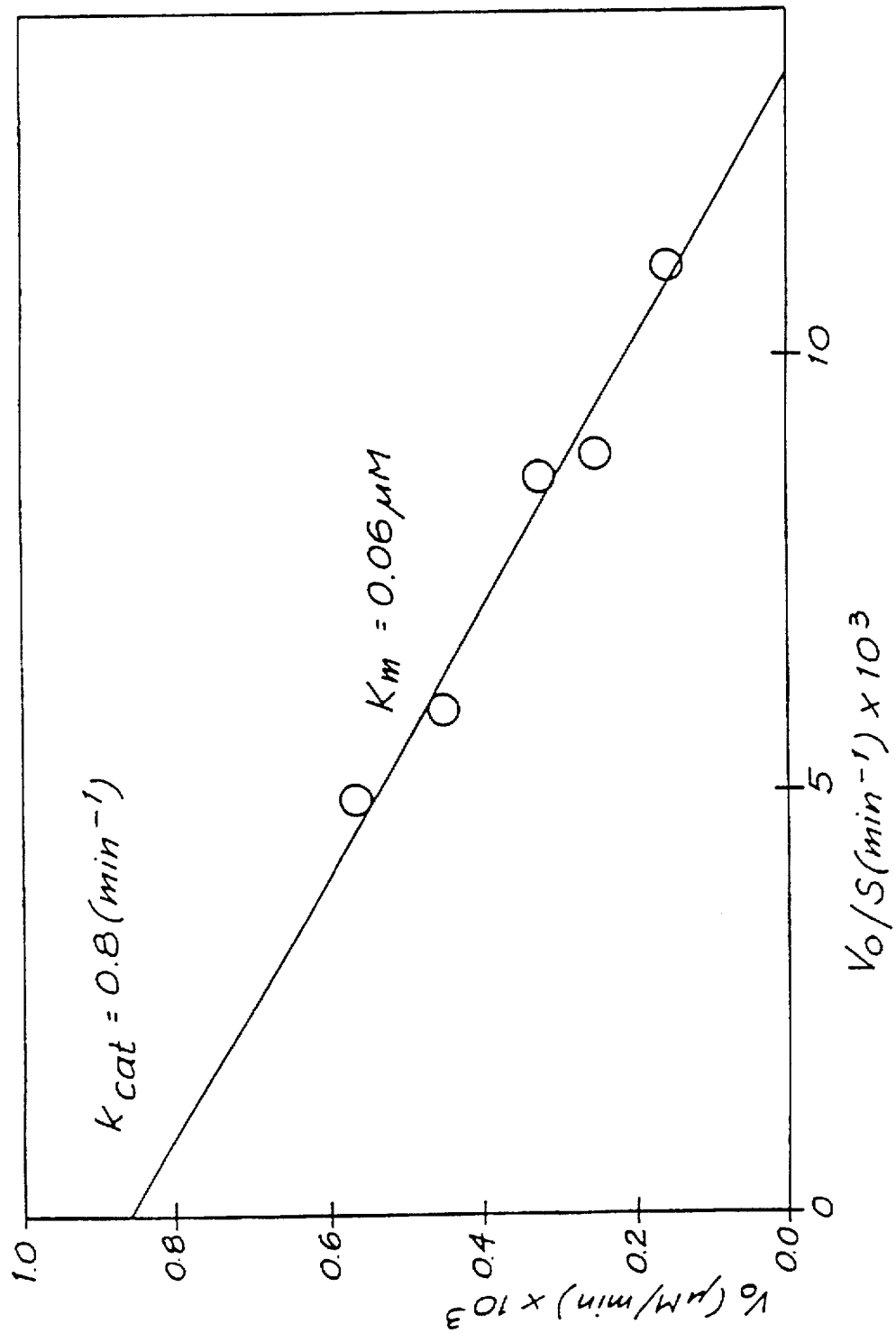
FIG. 7 shows the reaction properties of a smaller RNA substrate.

FIG. 7. Eadie Hofstee plot of catalytic RNA R51 cleavage of substrate RNA S10. The substrate S10 containing the RNA sequence: GACAGUCCUG (SEQ ID NO 2) was prepared from a DNA template containing the T-7 promoter as described in Example 2. This substrate was mixed with the catalytic RNA, R51, from Example 2 under standard conditions: 37° C. in 12 mM MgCl₂, 40 mM Tris pH 7.5 and 2 mM spermidine for 10 min. Concentrations of substrate used were as follows: 0.115 uM, 0.77 uM, 0.038 uM, 0.029 uM, 0.014 uM. The concentration of catalytic RNA, R51, used was 1 nM. The line was fit by linear regression analysis and intercept, kcat, and Michaelis constant, Km, calculated.

Figure 8A:
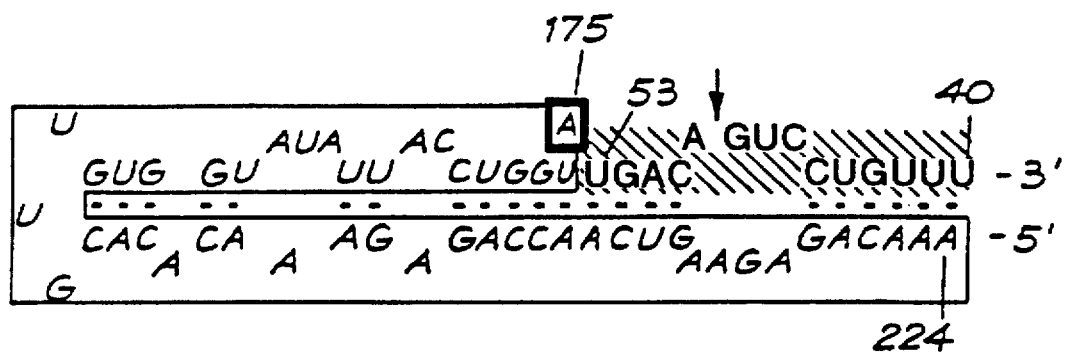
FIGS. 8A–8B shows the loss of catalytic activity when the terminal A at position 175 or the terminal bases AU at positions 175 and 176 are removed from the catalytic RNA.
Figure 8B:
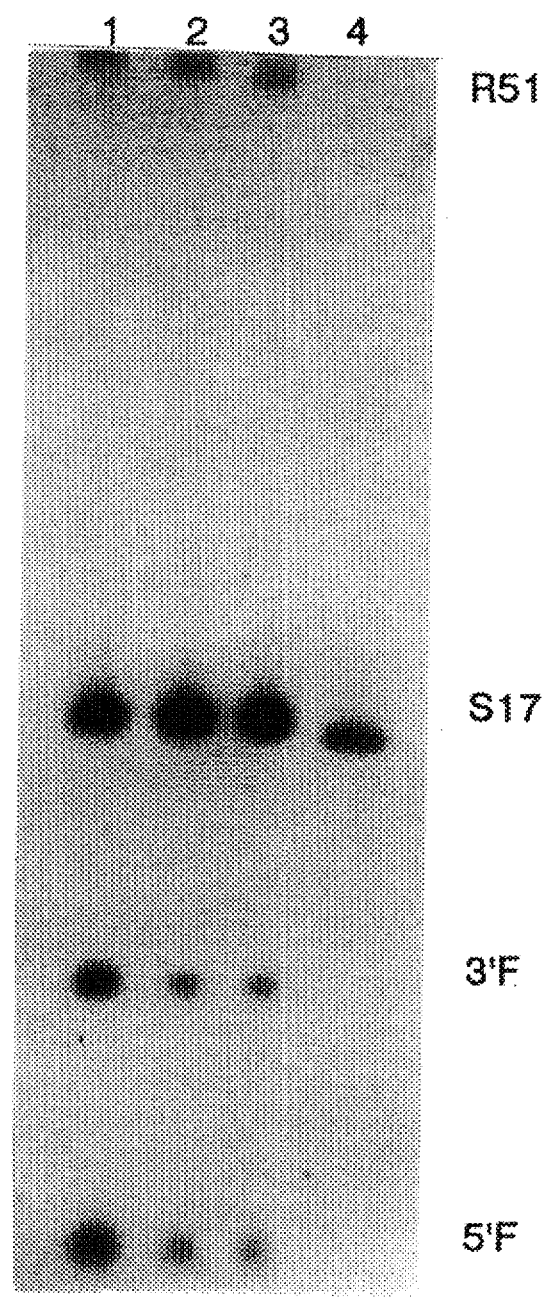

FIGS. 8A–8B. Removal of the terminal "A" at position 175 of the catalytic RNA. The "A" at base position 175 (circled) was removed and the resulting catalytic RNA, R50, reacted with substrate S17. In addition, two bases were removed, to give R49 which had both A175 and U176 removed. Concentration of substrate S17 was 0.3 uM and all catalytic RNA concentrations were 4 nM. The reaction times were 20 min under standard conditions. Lane 1 R51/S17; Lane 2 R50/S17; Lane 3 R49/S17; Lane 4 S17 alone. A 75% loss of activity was seen with R50 and R49.

Figure 9:
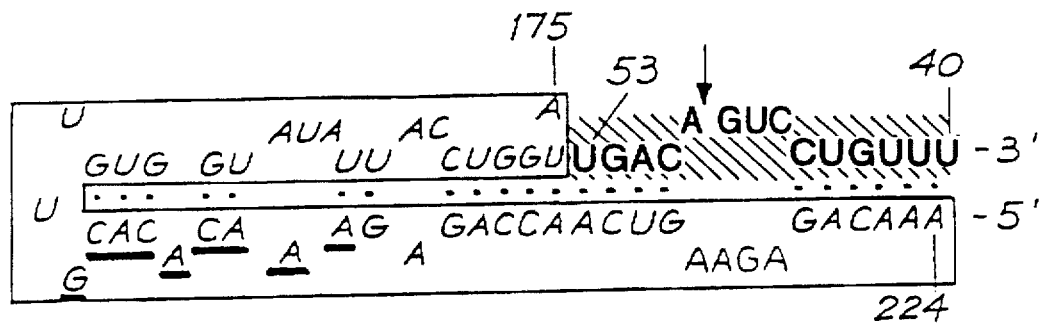
FIG. 9 shows loss of catalytic activity when bases 195–203 in the catalytic RNA sequence are removed.

FIG. 9. Loss of activity when bases 195–203 in the catalytic RNA sequence are removed. When the underlined bases were removed and the adjacent bases ligated together, no catalytic activity was seen.

Figure 10:
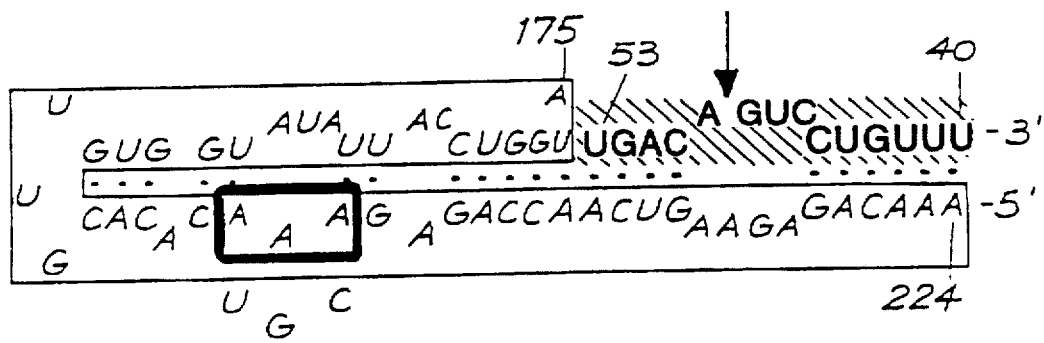
FIG. 10 shows loss of catalytic activity when bases AAA at positions 203, 202 and 201 are changed to CGU respectively.

FIG. 10. Loss of activity when bases AAA at positions 203, 202 and 201 are changed to CGU respectively. When the circled AAA bases were replaced by the underlying 5'-CGU-3' bases, no catalytic activity was seen.

Figure 11A:
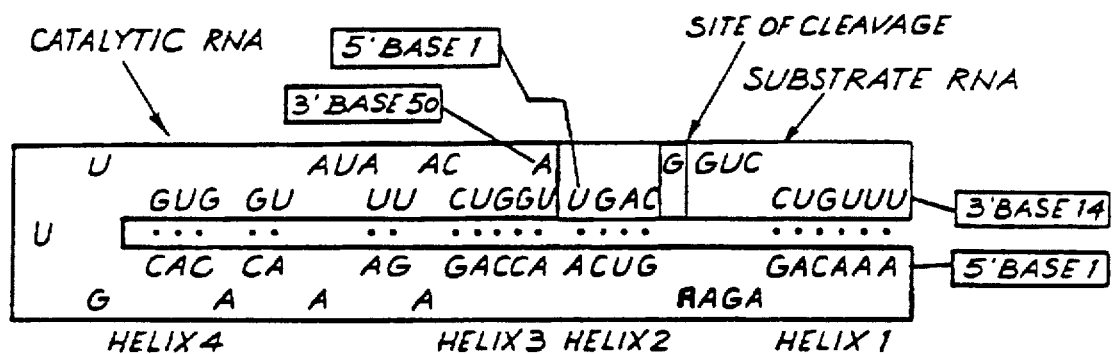
FIGS. 11A–11F show that there is no effect on catalytic activity when base A at position 49 in the substrate is changed to a G, U or C (SEQ ID NOS 60–62).
Figure 11B:
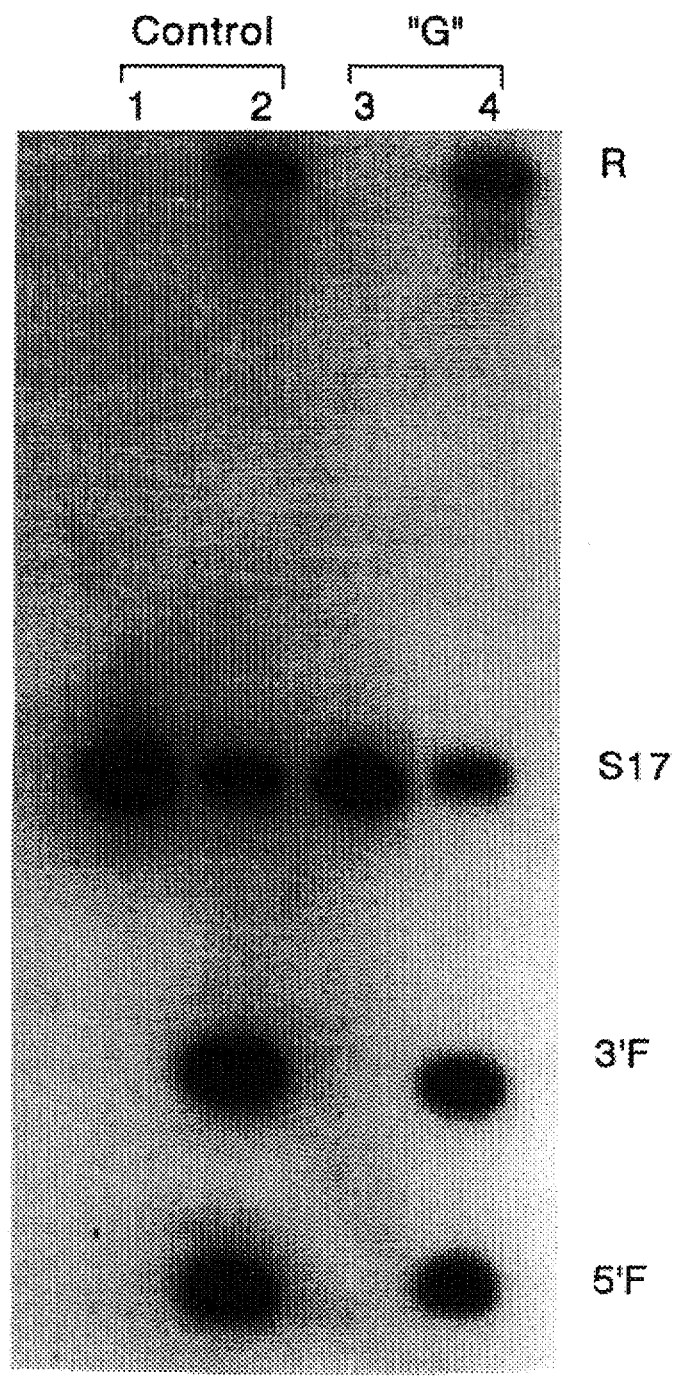

FIGS. 11A–11B. No effect on activity when base A49 in the substrate is changed to a "G". The circled "A" base 49 in the substrate was changed to a "G" and no effect on activity was seen. The concentration of R51 was 0.016 uM, [S17]=0.4 uM, and [S17(A→G)]=0.2 uM. Reaction under standard conditions was for 40 min. Lane 1 S17; Lane 2 S17/R51; Lane 3 S17(A→G); Lane 4 S17 (A→G)/R51.

Figure 11C:
Figure 11E:
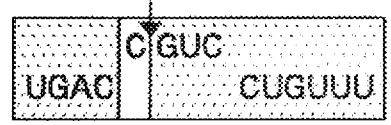
Figure 11D:
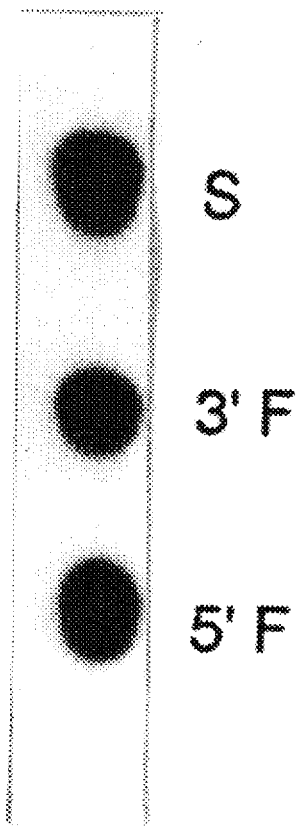

FIGS. 11C–11D. No effect on activity was seen when base A49 in the substrate was changed to a "U" (S17(A→U)). The concentration of substrate RNA S17 (A→U) used was 0.12 uM and the concentration of R51 was 0.0065 uM. Reaction was for 60 minutes under standard conditions. The catalytic RNA was unlabeled.

Figure 11F:
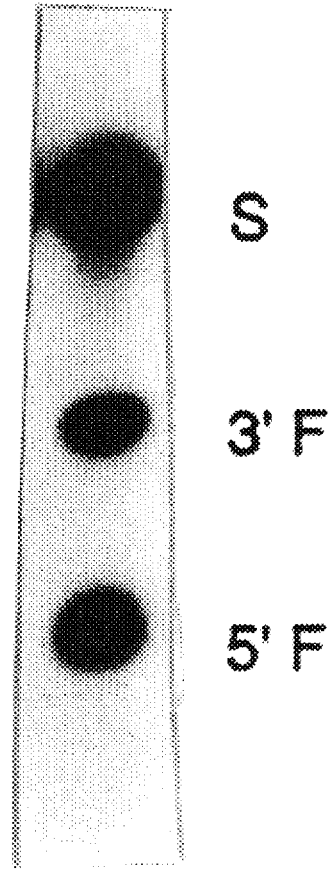

FIGS. 11E–11F. No effect on activity was seen when base A49 in the substrate was changed to a "C" (S17(A→C)). The concentration of substrate RNA S17 (A→C) used was 0.08 uM and the concentration of R51 was 0.0065 uM. Reaction was for 60 minutes under standard conditions. The catalytic RNA was unlabeled.

Figure 12A:
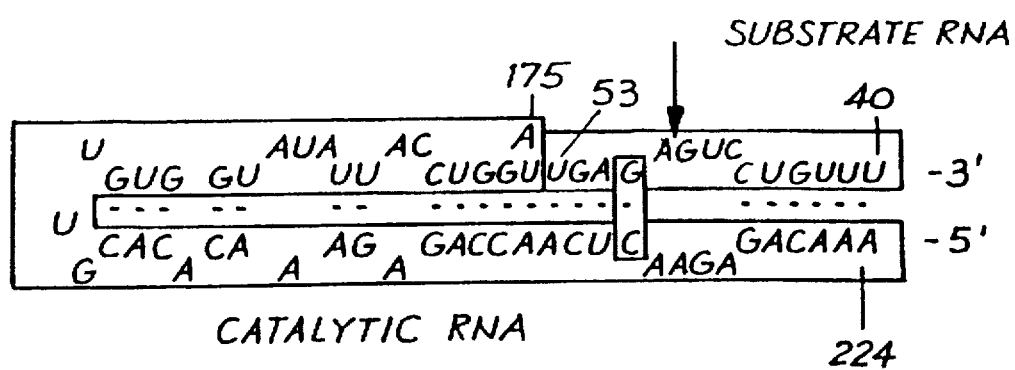

FIGS. 12A–12B. Different target RNA sequences can be used as long as the base pairing is maintained with the catalytic RNA. The C:G base pair predicted by the "hairpin" model of the catalytic complex of (−)sTRSV, FIG. 1, was changed to a G:C base pair (circled) and activity was maintained. In this experiment the usual substrate S17 was not used; instead a new substrate was used with the exact same sequence except the first two vector bases GC were eliminated. The resulting sequence of this new substrate S15 was gUGACAGUCCUGUUU (SEQ ID NO 3). The substrate containing the C50→G50 base change was S15 (C→G) and the catalytic RNA with the G214→C214 base change was R51(G→C). The reactions were run under standard conditions for 60 min at [R51]=0.07 uM, [S15]= 0.12 uM, [S15(C→G)]=0.15 uM, [R51(G→C)]=0.05 uM. Lane 1 R51/S15; Lane 2 R51(G→C)/S15; Lane 3 S15; Lane 4 R51(G→C)/ S15(C→G); Lane 5 S15(C→G).

Figure 13A:
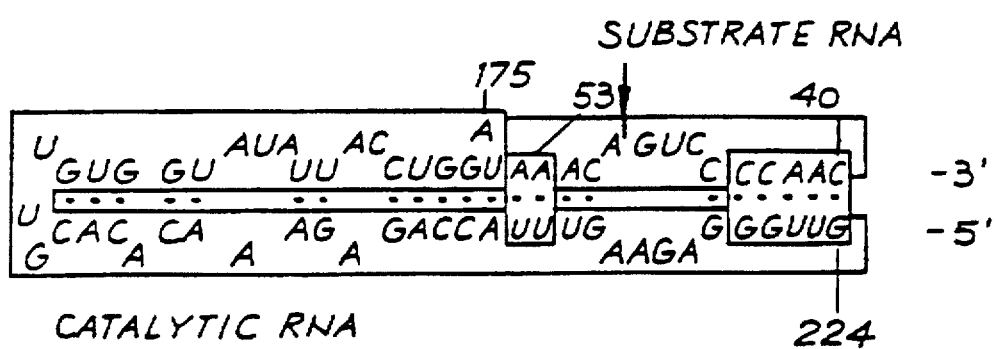
FIGS. 13A–13B shows that an RNA sequence (SEQ ID NO 65);(SEQ ID NO 66) found in tobacco mosaic virus can be cleaved at a specific site with the catalytic RNA of the present invention.
Figure 13B:
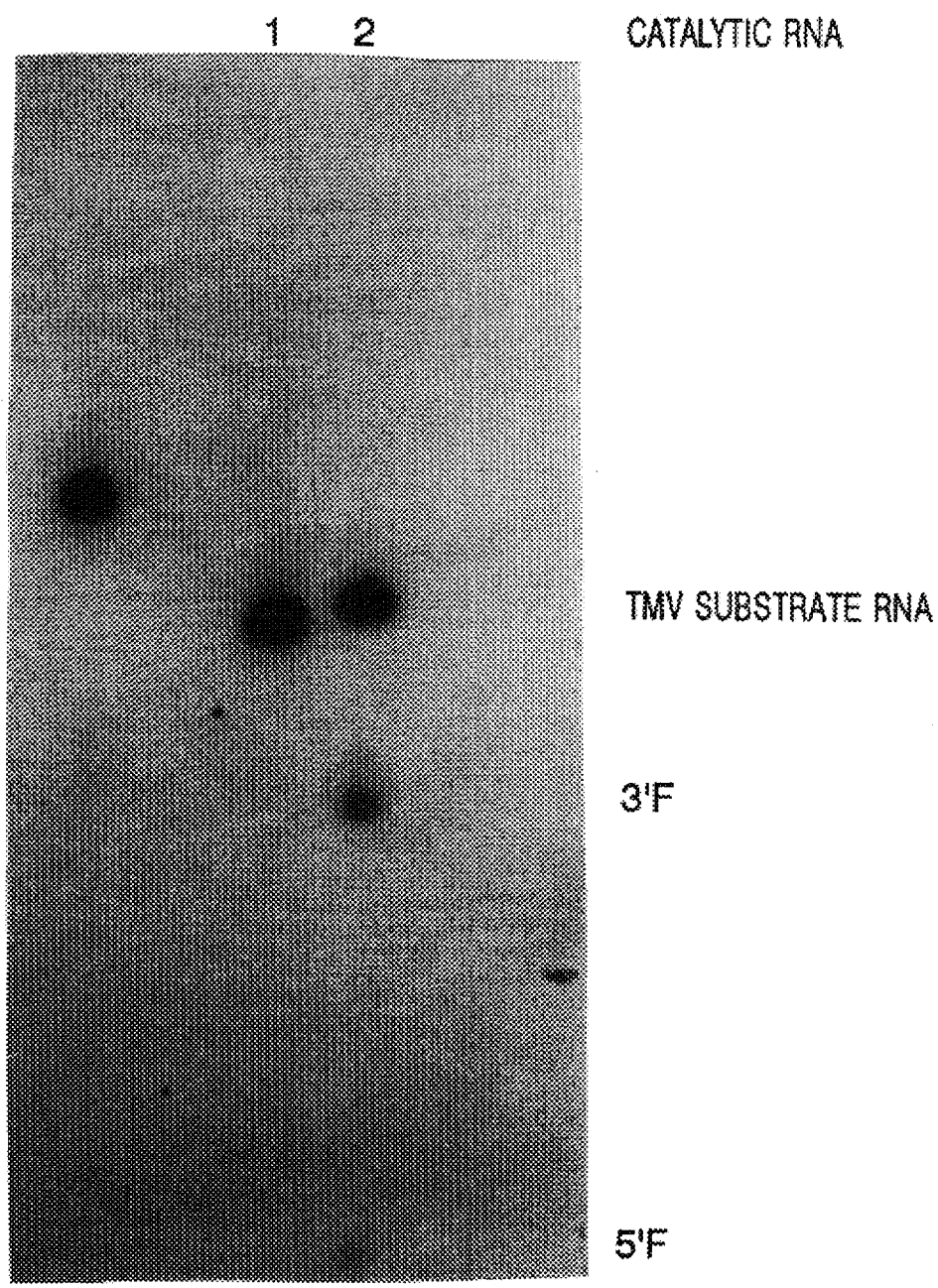
Figure 14A:
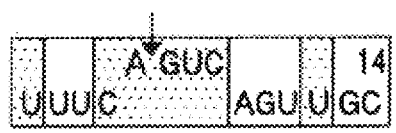
FIGS. 14A–14F show three substrates having sequences found in the sequence of the messenger RNA coding for chloramphenicol acetyl transferase.
Figure 14B:
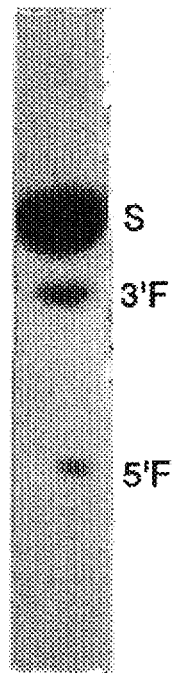
Figure 14C:
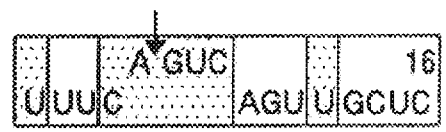
Figure 14D:
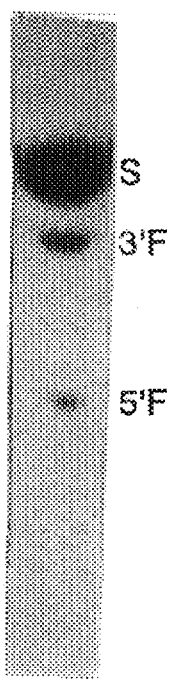
Figure 14E:
Figure 14F:
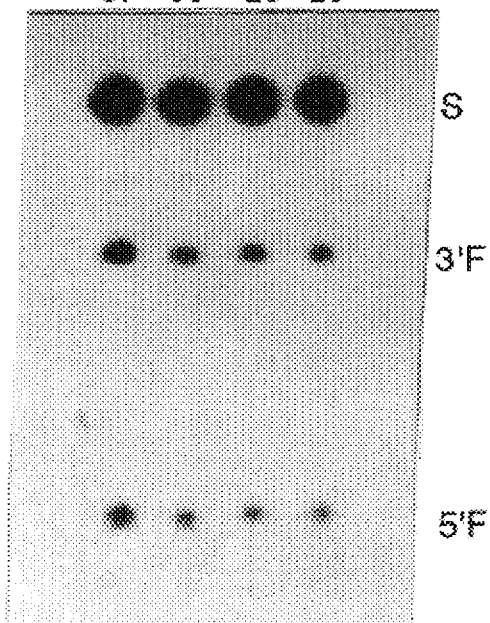

FIGS. 13A–13B. An RNA sequence found in tobacco mosaic virus (TMV) can be cleaved at a specific site. The substrate RNA shown is that beginning with nucleotide #538 in the tobacco mosaic virus sequence. The catalytic RNA was synthesized to base pair with the TMV substrate RNA in the stem regions of the "hairpin" as shown by the circled base pairs. Reaction was for 20 min under standard conditions with a catalytic RNA concentration of 3 nM and a substrate concentration of 0.06 uM. Lane 1 TMV substrate RNA only; Lane 2 TMV catalytic RNA/TMV substrate RNA.

FIGS. 14A–14F. The sequences of three substrate RNAs having sequences found in the messenger RNA for chloramphenicol acetyl transferase (CAT) are shown. They have 14-, 16- and 18-base long target sites, and the length of the 3' regions flanking the AGUC cleavage sequence is extended in substrates (B) and (C) as compared to substrate (A). Catalytic RNAs designed to base pair with the substrate RNAs in both the 3' and 5' regions flanking the cleavage sequence AGUC were synthesized. The open boxed bases are those which are different from those in the native (−)sTRSV substrate RNA sequence shown in FIG. 1.

Figure 15A:
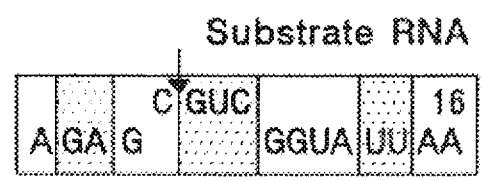
FIGS. 15A–15C shows the sequence of a substrate (SEQ ID NO 70) having a sequence found in the sequence coding for the gag protein of the HIV-1 virus which causes AIDS.
Figure 15B:
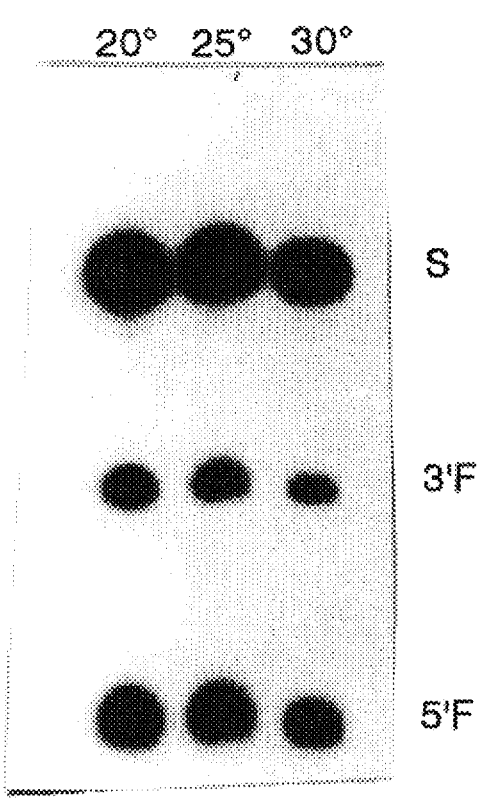
Figure 15C:
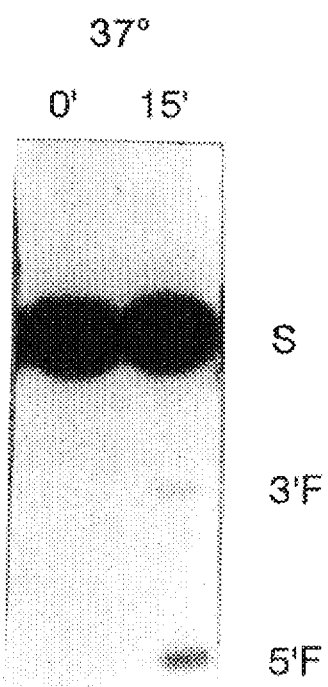

FIGS. 15A–15C. This figure shows the sequence of a substrate RNA having a sequence found in the region of the HIV-1 viral RNA which specifies the gag protein. A catalytic RNA was made whose sequence was designed so that the catalyst would base pair with the substrate RNA in both the 3' and 5' regions flanking the cleavage sequence. The open boxed bases are those which are different than those of the native (−)sTRSV sequence shown in FIG. 1. The catalytic RNA cleaved the substrate RNA at the arrow.

Figure 16A:
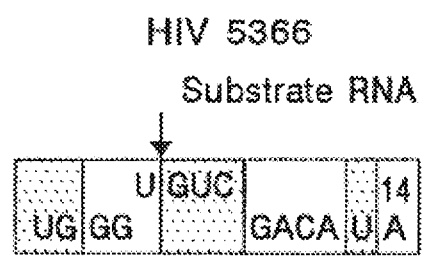
FIGS. 16A–16B shows the sequence of a substrate having a sequence found in the sequence coding for the regulatory tat protein of the HIV-1 virus.
Figure 16B:
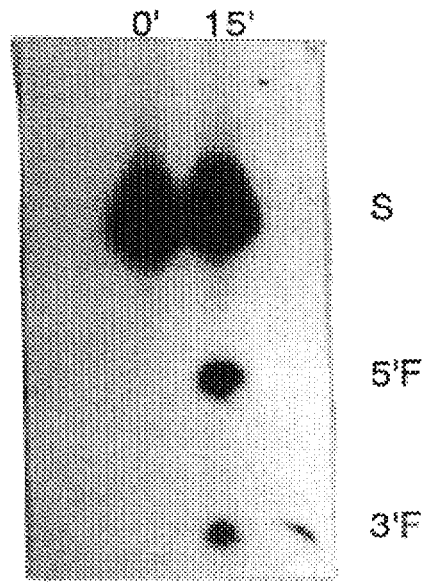

FIGS. 16A–16B. Shown is the sequence of a substrate RNA having the sequence found at the beginning of the coding region for the regulatory protein tat of the HIV-1 virus. A catalytic RNA was made which was designed so that it would base pair with the substrate RNA in both the 3′ and 5′ regions flanking the UGUC catalytic cleavage sequence. The open boxes are bases which are different from those of the native (−)sTRSV substrate sequence shown in FIG. 1. Cleavage occurred at the arrow as shown.

Figure 17A:
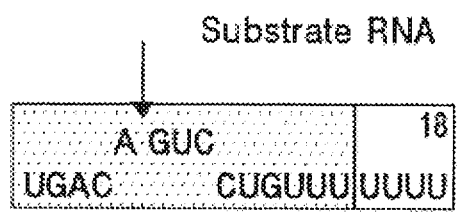
FIGS. 17A–17B shows the sequence of a substrate having four non-native U's (SEQ ID NO 72) added to the 3' end of the sequence of the native (−)sTRSV substrate shown in FIG. 1.
Figure 17B:
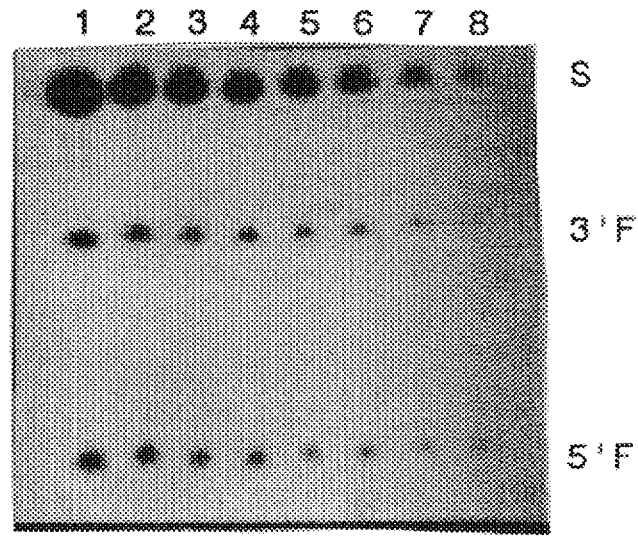

FIGS. 17A–17B. Shown is the sequence of a substrate RNA having four non-native bases (UUUU) added to the 3′ end of the sequence of the native (−)sTRSV substrate RNA shown in FIG. 1. A corresponding catalytic RNA was made whose sequence was designed so it would base pair with the substrate in both the 3′ and 5′ regions flanking the AGUC cleavage sequence. Cleavage rates with a constant catalytic RNA concentration and various concentrations of substrate RNA were determined by cutting out the bands of the acrylamide gels, counting the radioactivity and plotting the data using Michaelis-Menton procedures to calculate Km and kcat.

Figure 18:
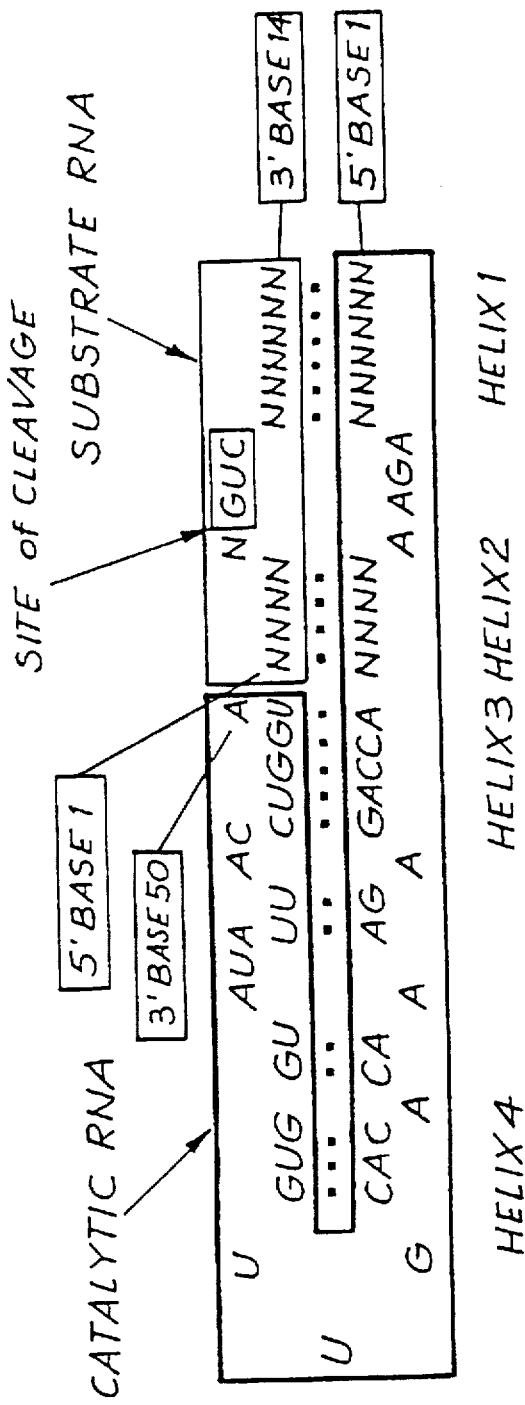
FIG. 18 summarizes the sequence requirements for the target region of the substrate RNA. Only GUC is required for cleavage (SEQ ID NO 73).

FIG. 18. Summary of the sequence requirements for the target region of substrate RNA. Only a GUC sequence is required for cleavage of the substrate as long as the short sequences of bases in the regions of the substrate flanking the cleavage sequence are substantially base paired with corresponding regions of the RNA catalyst. The regions of base pairing are labeled Helix 1 and Helix 2 in the figure. Also, the regions of base pairing predicted by the "hairpin" model for (−)sTRSV to exist in the "hairpin" portion of the catalyst are labeled Helices 3 and 4.

Figure 19A:
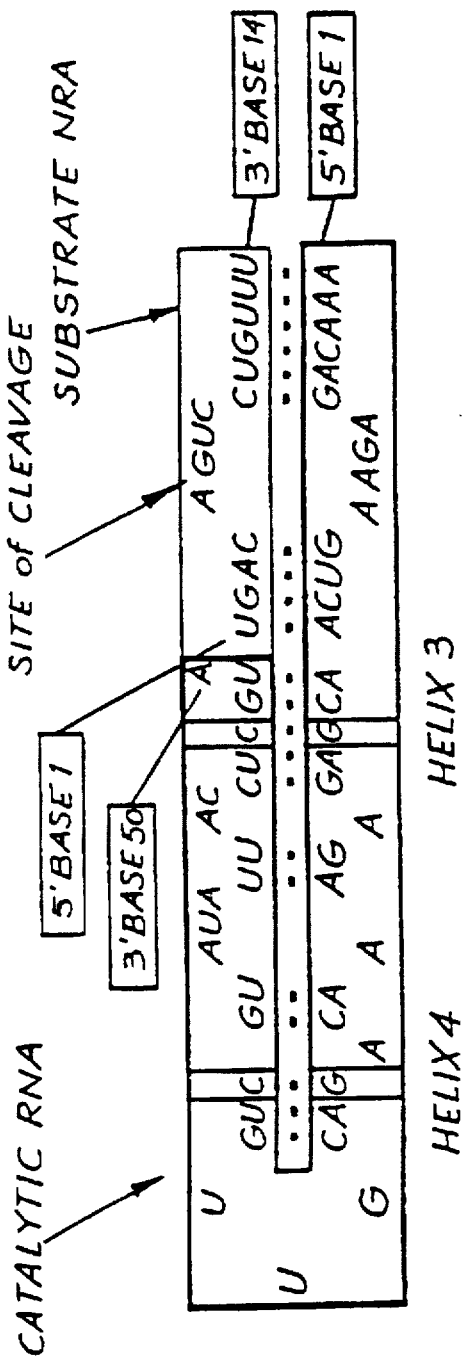
FIGS. 19A–19B shows the positions of base changes (open boxes) made in the sequence of the catalytic RNA shown in FIG. 1 in order to prove the existence of Helices 3 and 4 predicted by the "hairpin" model for (−)sTRSV RNA.
Figure 19B:
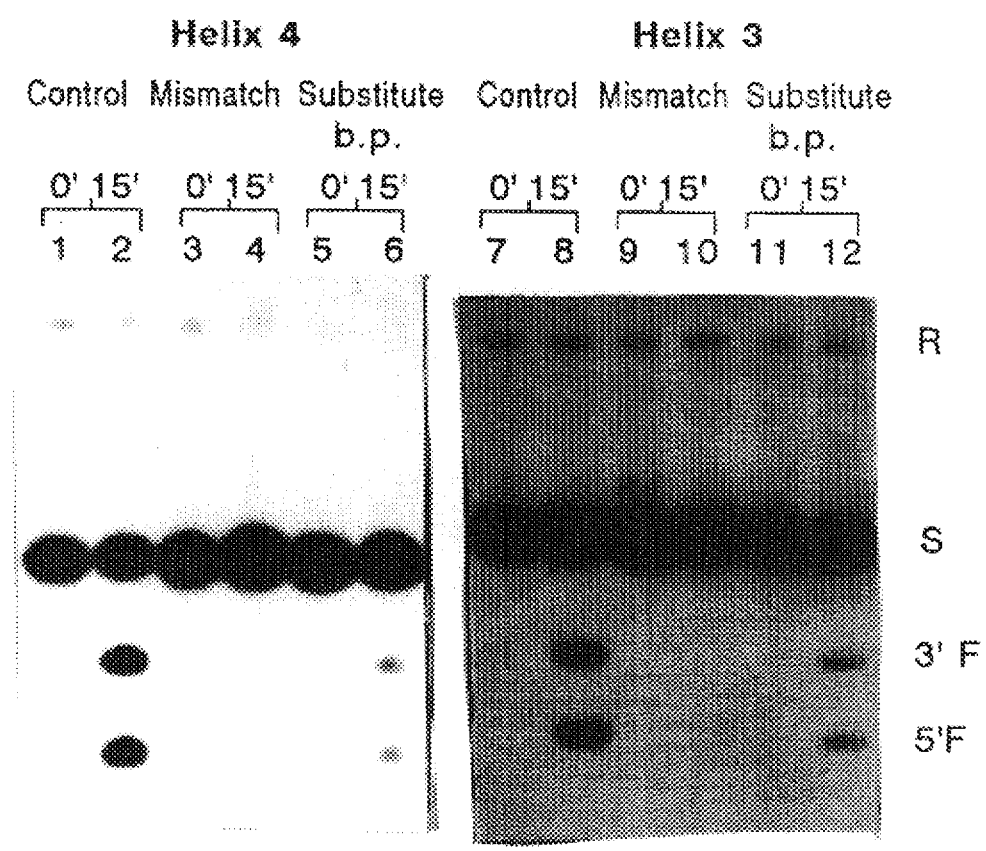

FIGS. 19A–19B. Confirmation of the existence of Helices 3 and 4 predicted by the "hairpin" model for (−)sTRSV RNA. A G→C base mutation in base 35 (count bases from the 5′ end of the catalytic RNA sequence shown) of the (−)sTRSV catalytic RNA sequence shown in FIG. 1 resulted in an RNA with no catalytic activity (Lanes 3 and 4 ("mismatch")). A double mutant, G35→C; C27→G had restored catalytic activity (Lanes 5 and 6 ("substitute b.p.")). These two base changes are in the Helix 4 region whose existence is predicted by the "hairpin" model for (−)sTRSV. Also, a catalytic RNA having a single base change at position 47 (G47→C) was inactive (Lanes 9 and 10), while a double mutant, with a second mutation C17→G, had restored activity (Lanes 11 and 12). These two base changes are in the Helix 3 region whose existence is predicted by the "hairpin" model. The control (Lanes 1, 2, 7 and 8) is cleavage of the substrate RNA S17 having the native (−)sTRSV sequence by catalytic RNA sequence R51 having the native sequence.

Figure 20A:
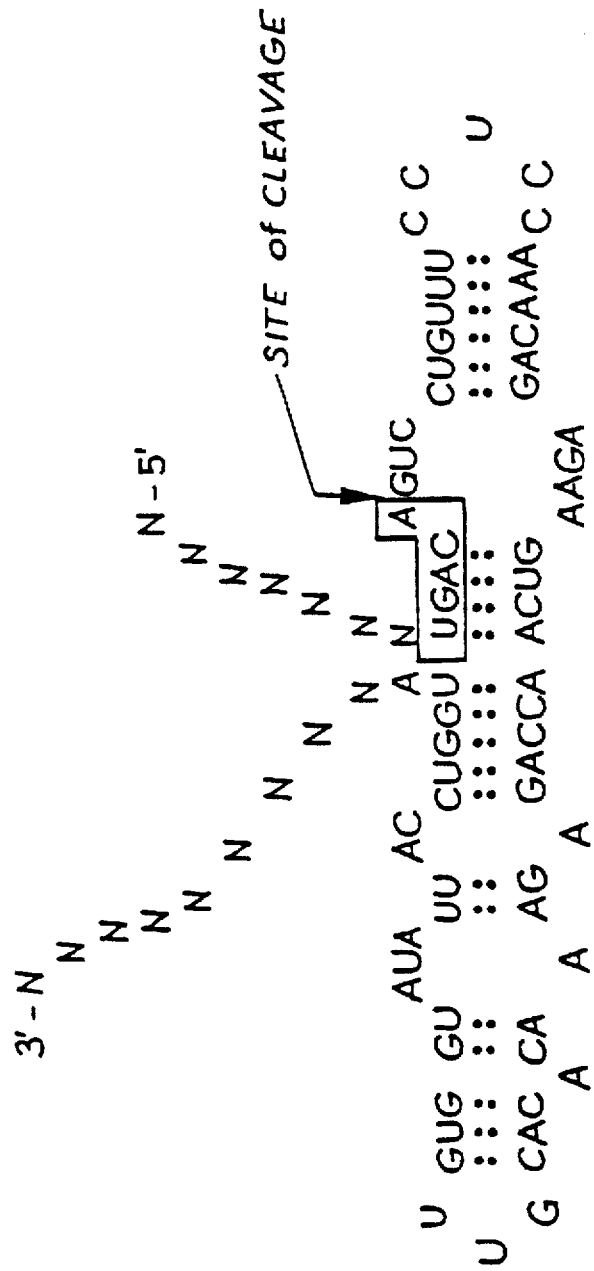
FIGS. 20A–20B shows the RNA sequence of an autocatalytic cassette (SEQ ID NO 75) that has utility in terminating transcription at a very specific site.
Figure 20B:
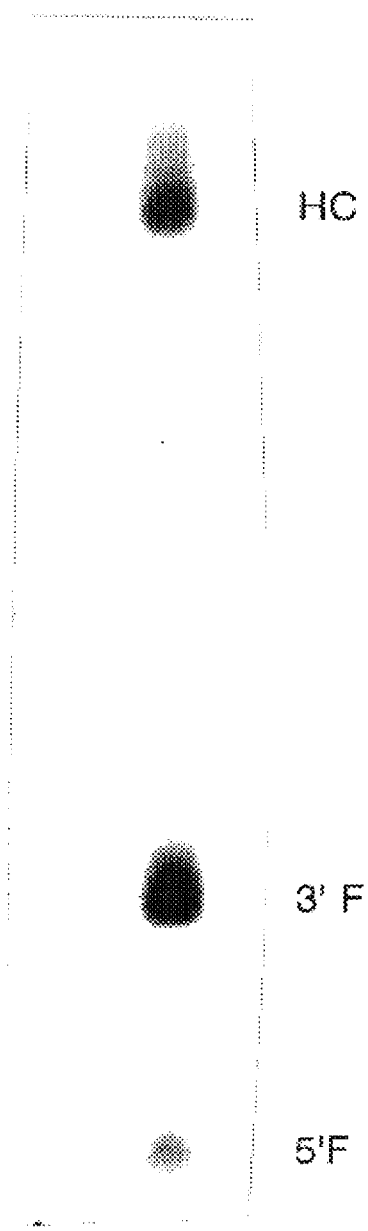

FIGS. 20A–20B. The RNA sequence of a synthetic "hairpin" autocatalytic cassette is shown. The sequence shown in FIGS. 20A–20B is the same as that of the catalyst shown in FIG. 1, but with additional 5′ bases added to form a loop at the 5′ end of the catalyst and to provide a substrate target sequence (i.e., a cleavage sequence and upstream and downstream flanking bases) which can bind to the substrate binding portion of the catalyst sequence. Such an RNA was prepared. When transcription was performed, the cassette autocatalytically cleaved at the expected site to give the appropriate 3′F and 5′F products.

Figure 21A:
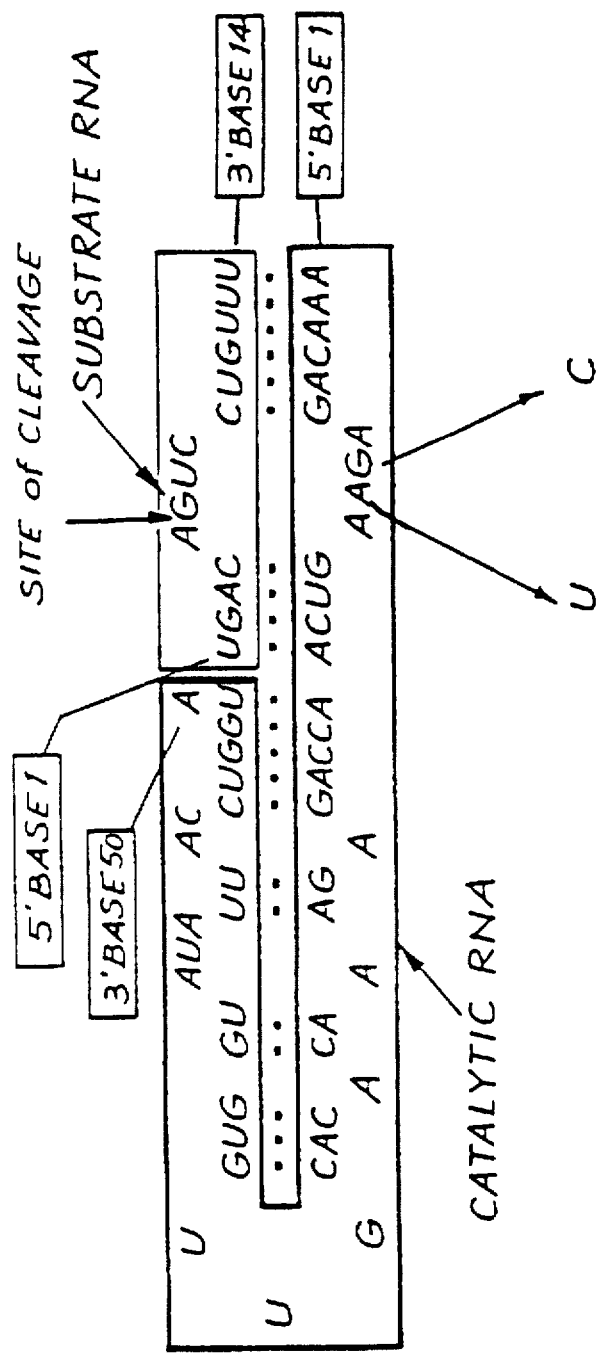
FIGS. 21A–21B shows the positions of two base changes that were made in the native (−)sTRSV catalytic RNA sequence shown in FIG. 1.
Figure 21B:
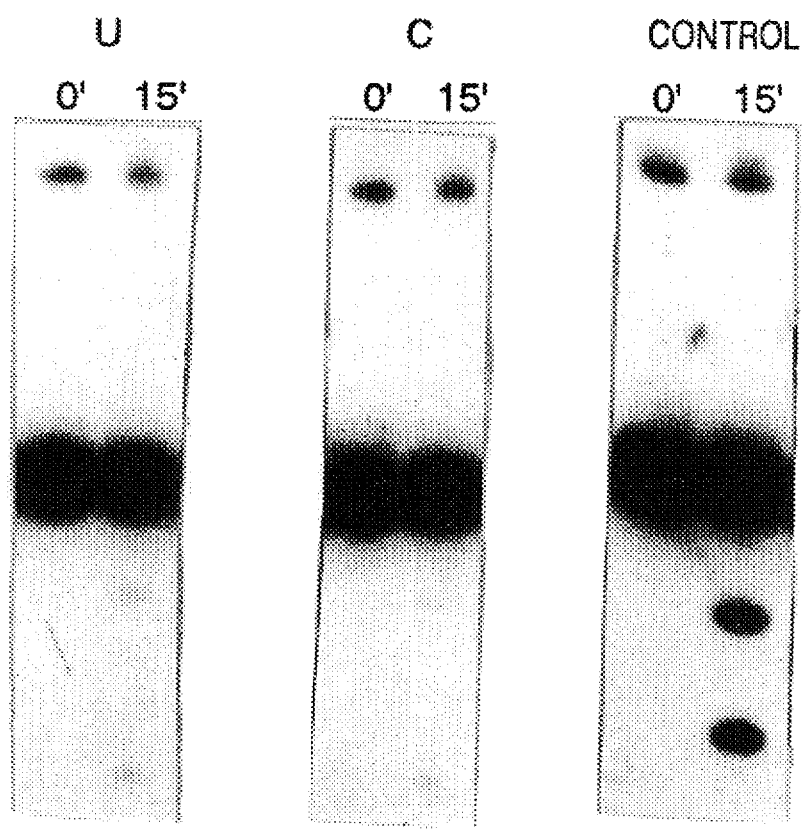

FIGS. 21A–21B. Shown are two base changes that were made in the native (−)sTRSV catalytic sequence shown in FIG. 1. The two bases changes were an "A" to "U" mutation at position 217 and a "G" to "C" mutation at position 216. FIGS. 21A–21B also shows the separation patterns on acrylamide gels of the reaction products obtained by reacting one of these catalysts or R51 (control) with substrate S17. Both base changes produced catalysts that were inactive when the catalysts were reacted with substrate S17 under standard conditions for 15 minutes.

Figure 22A:
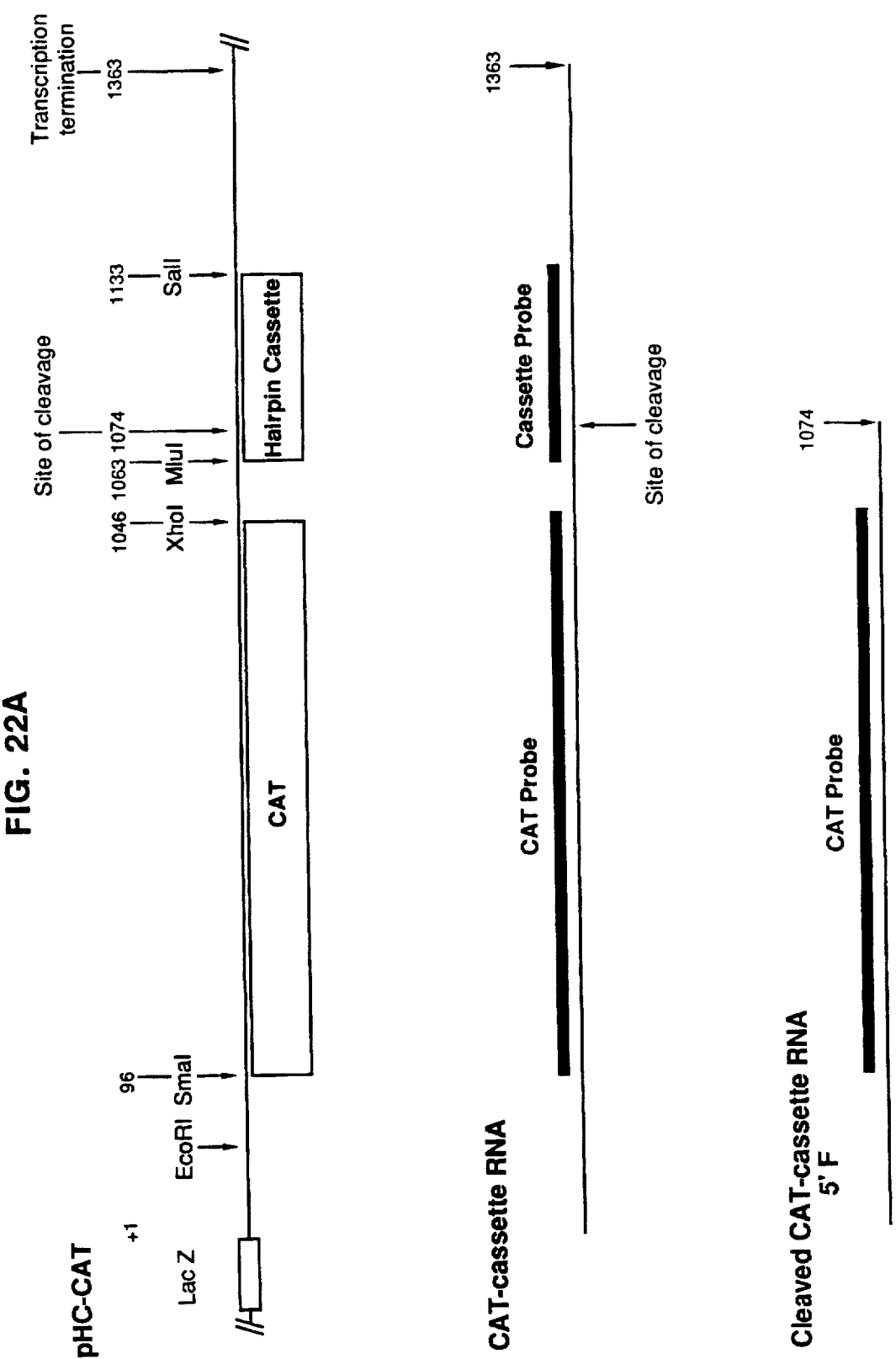
FIG. 22A shows a plasmid map illustrating pertinent features of vector pHC-CAT which contains the CAT gene linked to the "hairpin" autocatalytic cassette of the invention. Also shown is the expected RNA transcript of the illustrated region of PHC-CAT and the expected 5' fragment of the autocatalytic cleavage.

FIG. 22A shows a plasmid map illustrating pertinent portions of vector pHC-CAT containing the CAT gene linked to the "hairpin" autocatalytic cassette of the invention so that the "hairpin" autocatalytic RNA would be expected to serve as a chain terminator for the CAT gene. Also shown is the expected RNA transcript of the illustrated region ("CAT-cassette RNA") and the expected 5′ fragment of the autocatalytic cleavage ("Cleaved CAT-cassette RNA"). Finally, the figure illustrates the location of DNA probes designed to hybridize with different regions of the CAT-cassette RNA transcript and Cleaved CAT-cassette 5′ fragment.

Figure 22B:
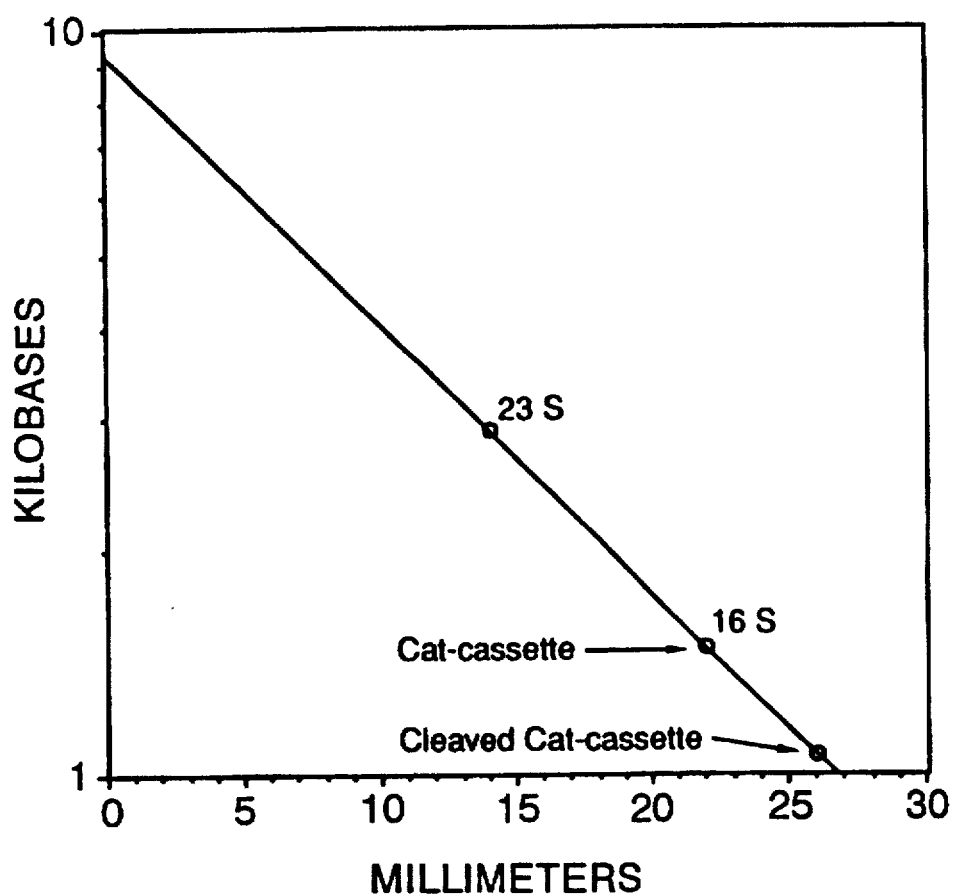
FIGS. 22B–22C shows the results of Northern blot analysis of RNA produced by host cells transformed with pHC-CAT.
Figure 22C:
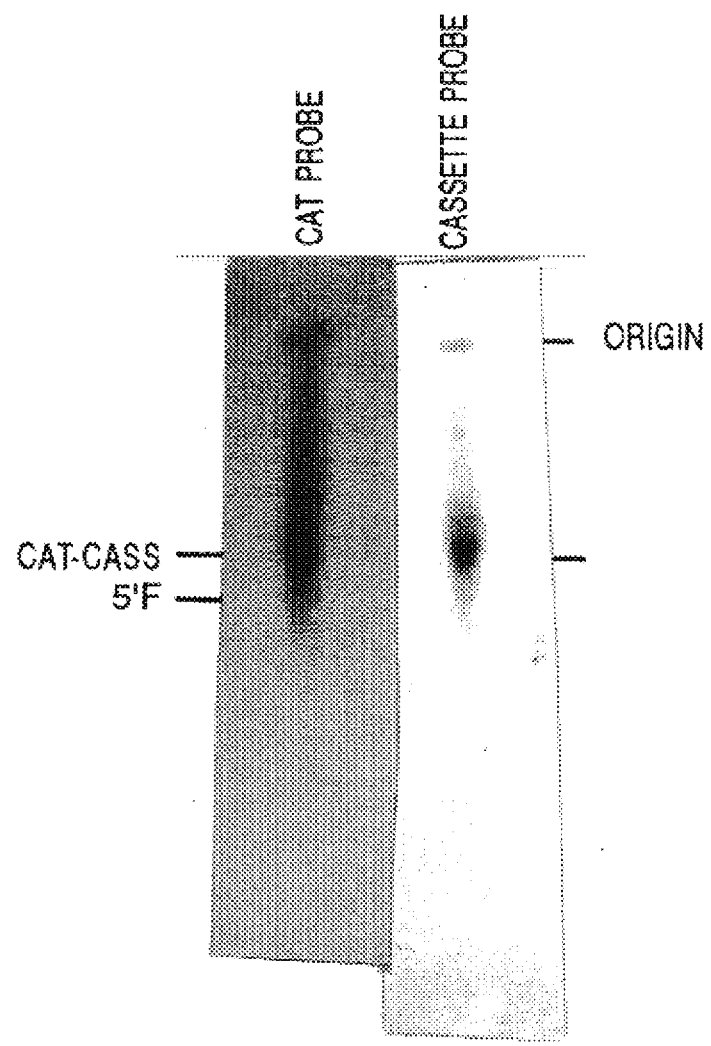

FIGS. 22B–22C show the results of Northern blot analysis of RNA isolated from *Escherichia coli* host cells transformed with pHC-CAT. When the CAT probe was used, both the full length transcript and the expected 5′ cleavage fragment were detected, indicating that cleavage took place in vivo. When the "hairpin" autocatalytic cassette probe was used, only the full length CAT-cassette RNA transcript was detected. The fact that the 5′ fragment did not hybridize with this probe was to be expected, since most of the "hairpin" autocatalytic cassette transcript would be in the 3′ fragment after cleavage. Although, it would be expected that the "hairpin" autocatalytic cassette probe would hybridize to the 3′ fragment, the fact that the 3′ fragment was not detected by Northern blot analysis is not surprising. The 5′ terminus of the 3′ fragment would contain a 5′-OH and not the 5′-ppp which is ordinarily seen in RNA transcripts. Thus, the 3′ fragment would be expected to be very labile in vivo and was likely degraded immediately after the autocatalytic cleavage.

Figure 23:
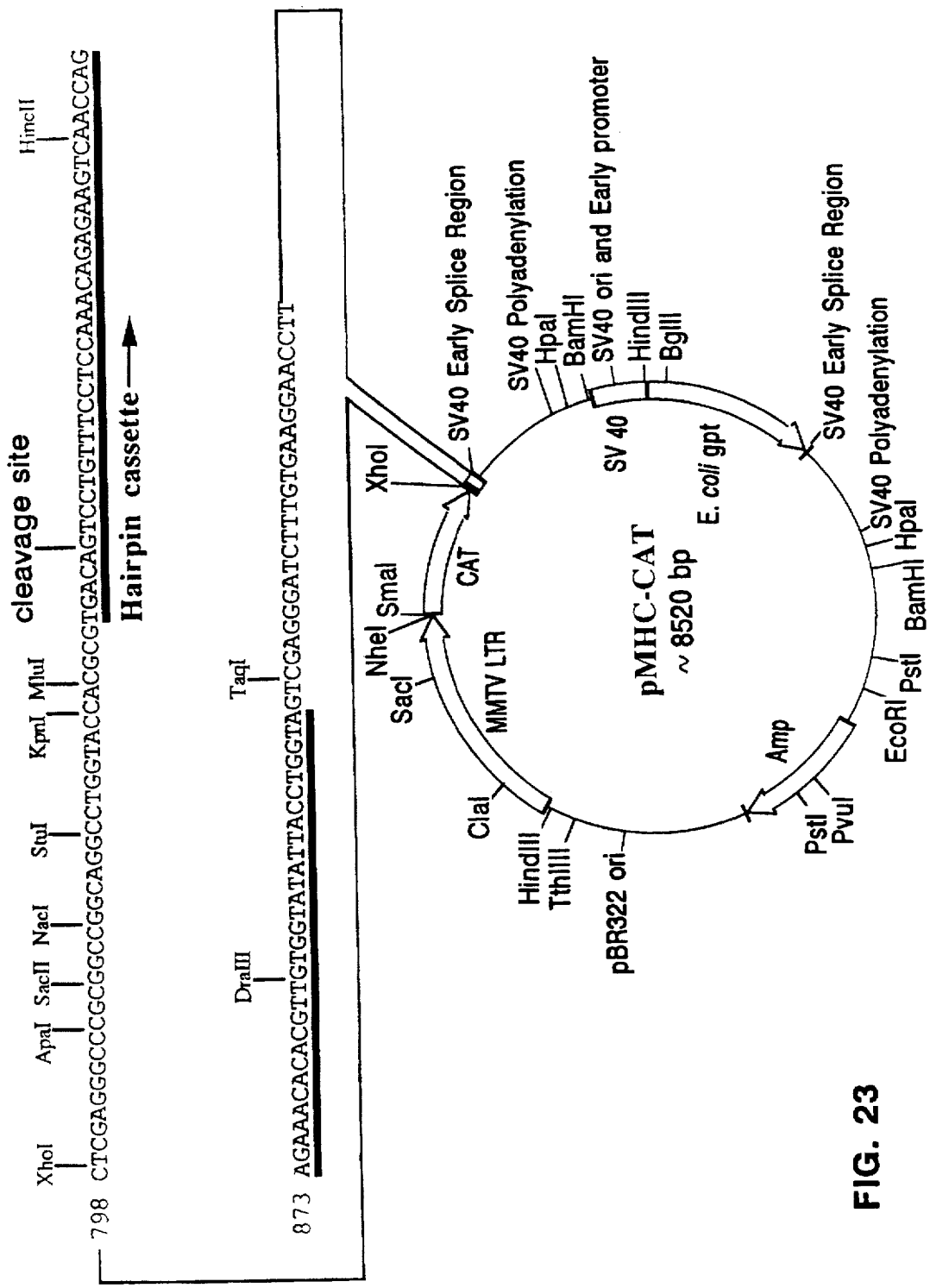
FIG. 23: Map of the pMHC-CAT mammalian expression vector (SEQ ID NO 76).

FIG. 23. Shown is the map of the vector pMHC-CAT which was constructed by excising the "hairpin" autocatalytic cassette from pHC (prepared as described in Example 23) with SmaI/SalI and ligating it to vector pMSG at the SmaI/XhoI sites to give the vector pMHC. Then, the CAT gene was excised from pMAM-NEO-CAT with SmaI/XhoI and was ligated into pMHC at the SmaI/XhoI sites to give pMHC-CAT as shown.

Figure 24:
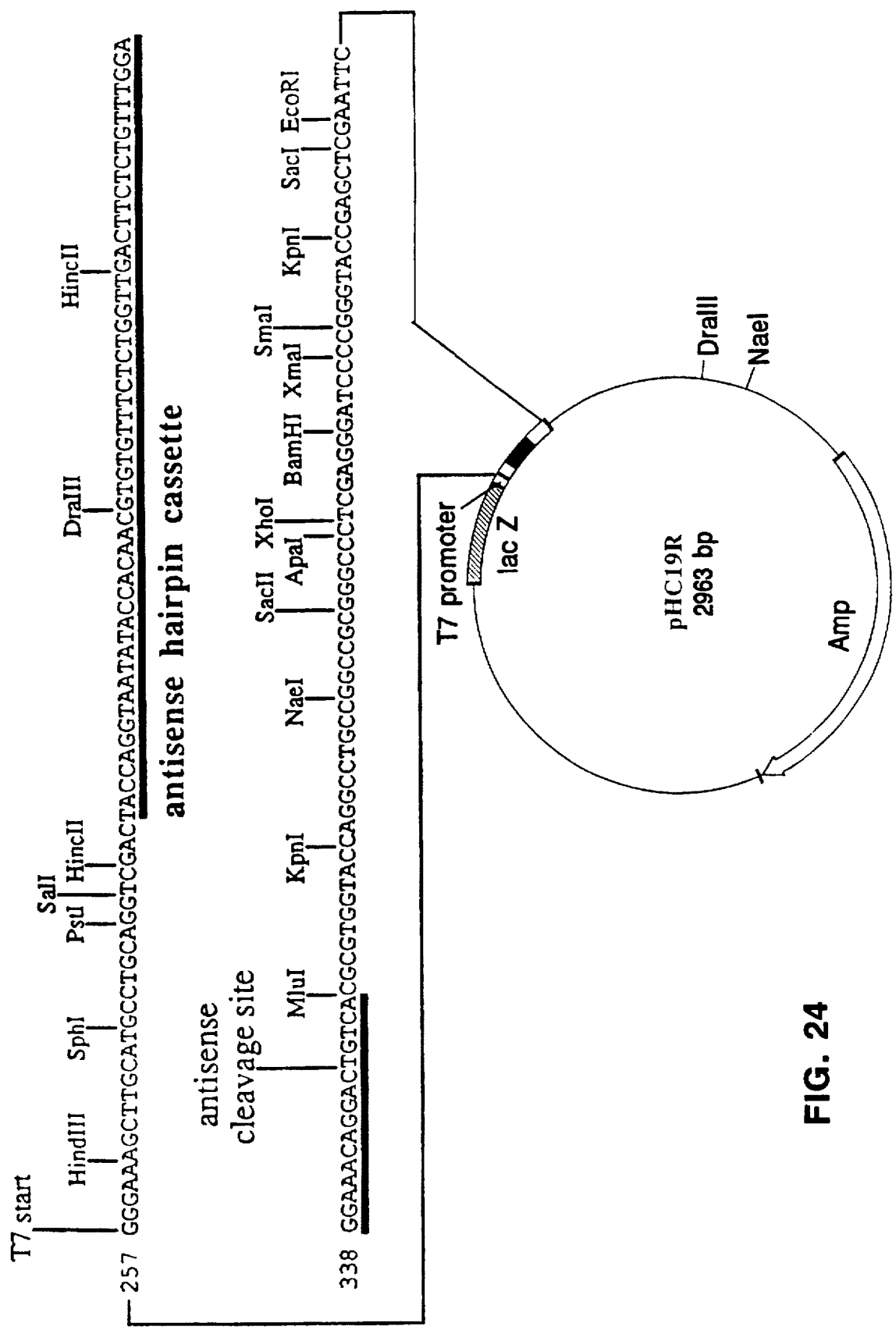
FIG. 24: Map of plasmid pHC19R (SEQ ID NO 77).

FIG. 24. Shown is the map of the vector pHC19R which was prepared by excising the "hairpin" autocatalytic cassette from pHC with BamHI/SalI and ligating it to the SalI/BamHI sites of pTZ19R to give pHC19R as shown.

Figure 25:
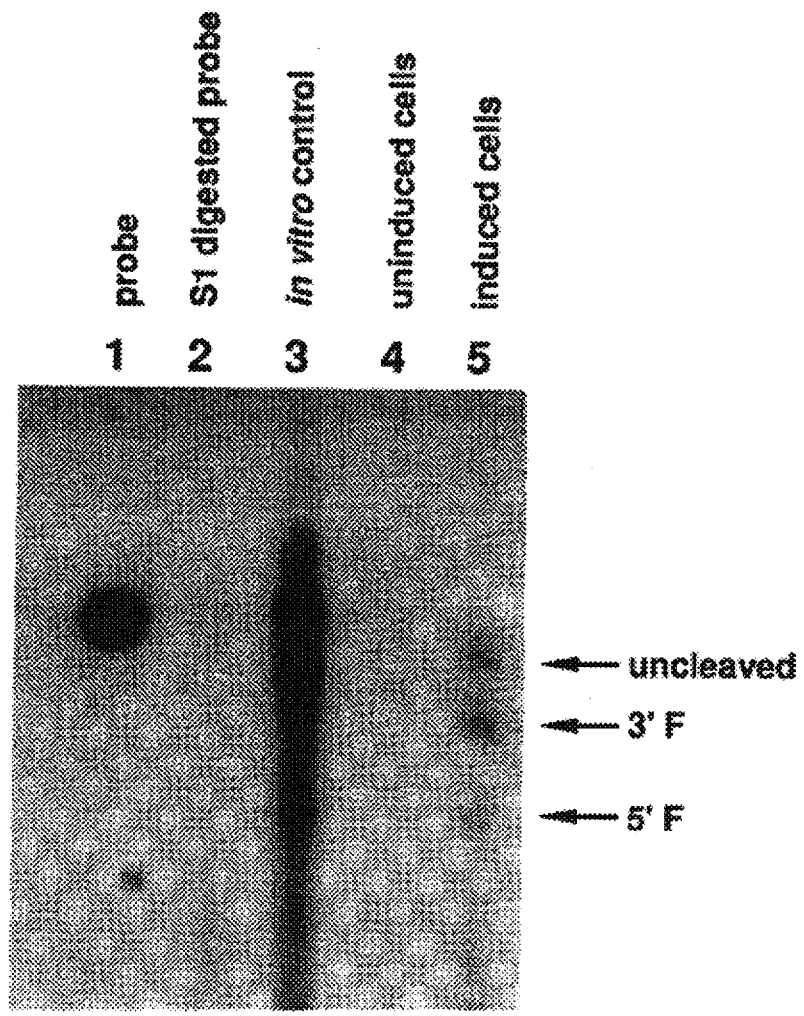
FIG. 25: Shows the results of S1 nuclease protection assay of RNA from transfected CHO cells and RNA controls.

FIG. 25. Shown are the results of an S1 nuclease protection assay performed on RNA isolated from CHO cells that had been transfected with pMHC-CAT. In the gel shown in FIG. 25, the lanes contain: Lane 1---probe (148 nt); Lane 2- - -S1 nuclease digested probe; Lane 3---in vitro transcribed "hairpin" autocatalytic cassette that had been hybridized to probe and S1 nuclease digested (uncleaved 134 nt, 3′F 87 nt, 5′F 47 nt); Lane 4- - -RNA isolated from uninduced, pMHC-CAT-transfected CHO cells, hybridized to probe and S1 nuclease digested; and Lane 5---RNA isolated from dexamethasone induced, PMHCCAT-transfected CHO cells, hybridized to probe and S1 nuclease digested (uncleaved 111 nt, 3′F 69nt, 5′F 42 nt). All mobilities were as expected.

Figure 26:
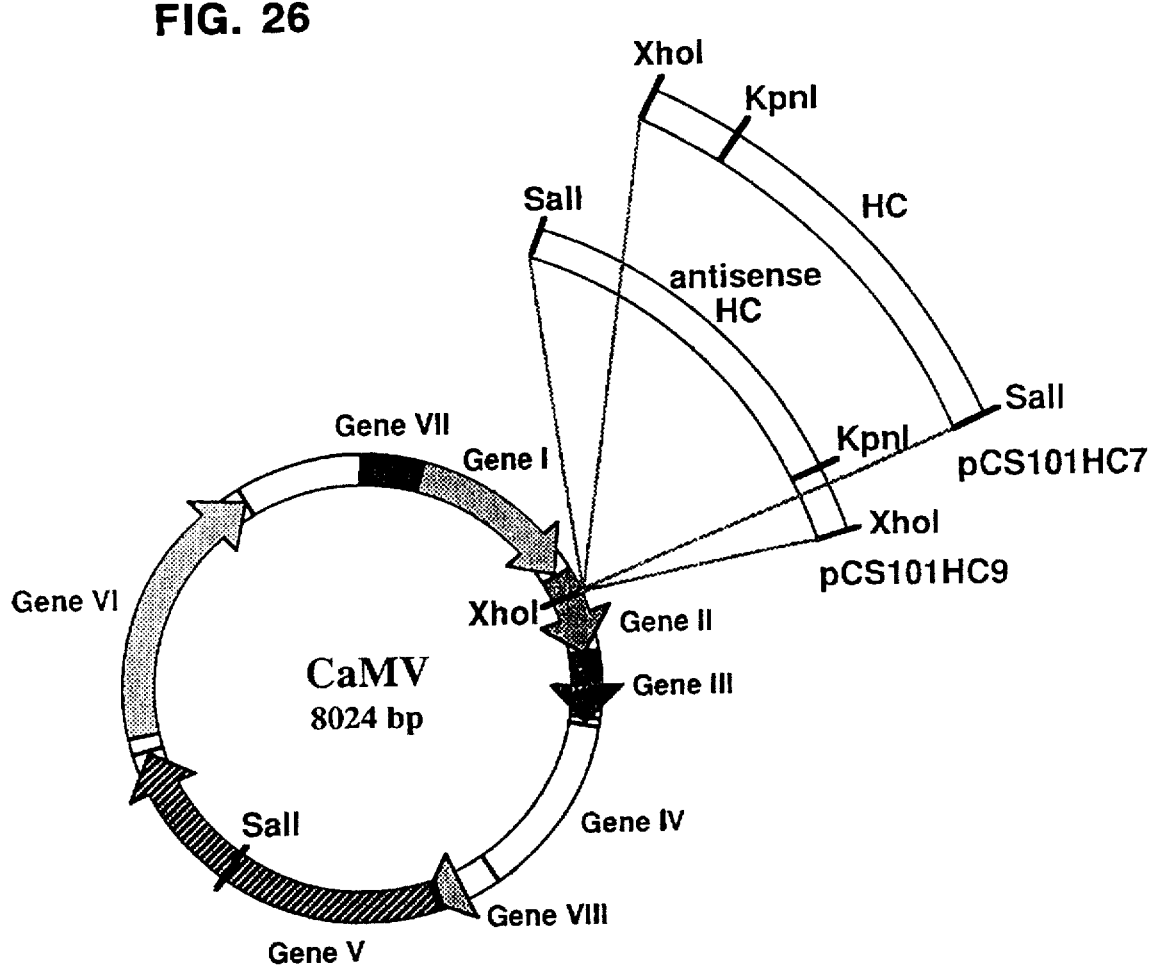
FIG. 26: Map of viral vector constructions (CMV) with the hairpin autocatalytic cassette in the sense orientation (pCS101HC7) and the antisense orientation (pCS101HC9).

FIG. 26. Shown are catalytic RNA/viral vector constructions used to infect plants. In these constructions, the "hairpin" autocatalytic cassette from the vector pHC was ligated to the cauliflower mosaic virus (CMV) in vector pCS101 to give the two engineered CMV viral constructs shown. The "hairpin" autocatalytic cassette is in the sense orientation in pCS101HC7 and in the antisense orientation in pCS101HC9.

FIG. 27A: Shown are the results of an S1 nuclease protection assay performed on RNA isolated from turnip plants that had been infected with pCS101HC7 or pCS101HC9. Lane 1 is undigested "hairpin" autocatalytic RNA probe (148 nt) and Lane 2 is RNA transcribed from HindIII-digested plasmid pHC which gave three RNA products—uncleaved "hairpin" autocatalytic cassette (158 nt), 3'F (87 nt) and 5'F (71 nt). The remaining lanes are all S1 nuclease digests of probe hybridized to the following RNA preparations: Lane 3—RNA from uninfected plants; Lane 4—RNA from plants infected by the virus control (pCS101); Lane 5—RNA from plants infected with pCS101HC7 (uncleaved 112 nt, 3'F 70 nt and 5'F 42 nt); Lane 6—RNA from plants infected with pCS101HC9.

FIG. 27B: Results of Northern blot analysis of the RNA isolated from plants that were mock infected, infected with pCS101 (wild-type CMV) or infected with pCS101HC7. The probe was labelled "hairpin" autocatalytic RNA. Lane 1, RNA from mock-infected plants; Lane 2, RNA from plants infected with pCS101 (wild-type CMV); and Lane 3, RNA from plants infected with pCS101HC7.

Figure 27C:
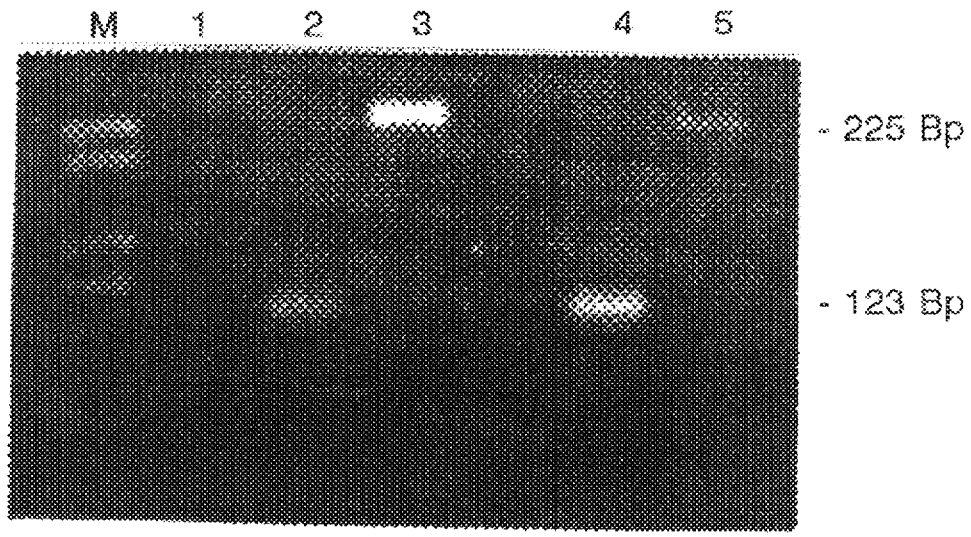
FIG. 27C: Results of PCR amplification of viral sequences from control and infected turnip plants.

FIG. 27C: Total DNA from plants that were mock infected, infected with pCS101 (wild-type CMV) or infected with pCS101HC7 was amplified by the polymerase chain reaction (PCR). Lane M, molecular weight markers; Lane 1, PCR-amplified DNA from mock-infected plants; Lane 2, PCR-amplified DNA from plants infected with pCS101 (wild-type CMV); Lane 3, PCR-amplified DNA from plants infected with pCS101HC7; Lane 4, PCR-amplified DNA from the pCS101 plasmid; and Lane 5 PCR-amplified DNA from pCS101HC7 plasmid.

Figure 27D:
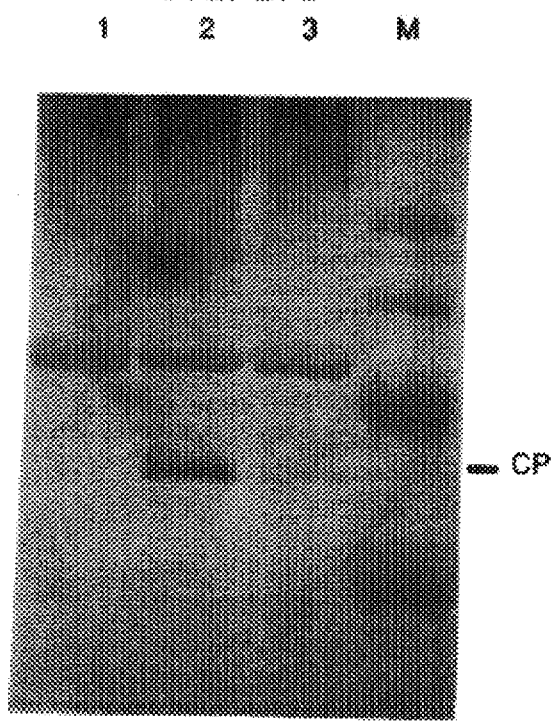
FIGS. 27D and 27E: Results of Western immunoblot analysis of protein extracts of turnips leaves from control and infected plants.
Figure 27E:
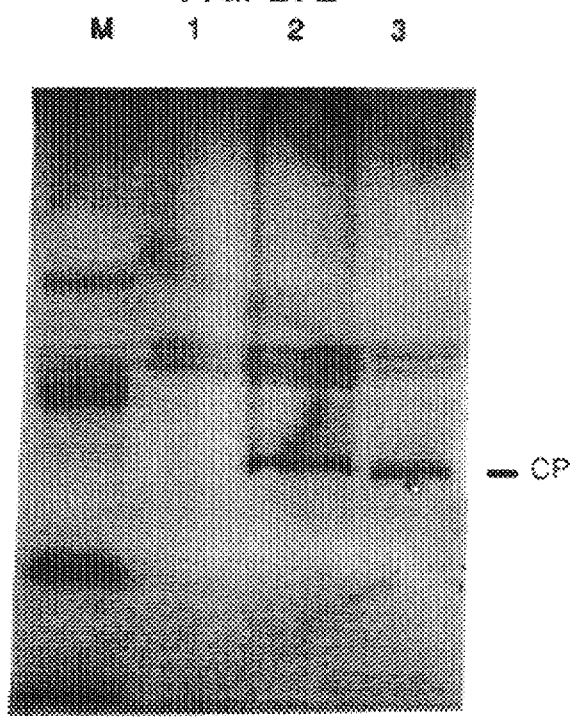

FIGS. 27D and 27E: Results of Western immunoblot analysis of protein extracts of turnips leaves from plants that were mock infected, infected with pCS101 (wild-type CMV) or infected with pCS101HC7. FIG. 27D shows the results for plants one month after inoculation, and FIG. 27E shows the results for plants two months after inoculation. The lanes are the same in both figures. Lane 1, protein from mock-infected plants; Lane 2, protein from plants infected with pCS101 (wild-type CMV); and Lane 3, protein from plants infected with pCS101HC7. CP=coat protein, (M)= molecular weight markers.

Figure 28:
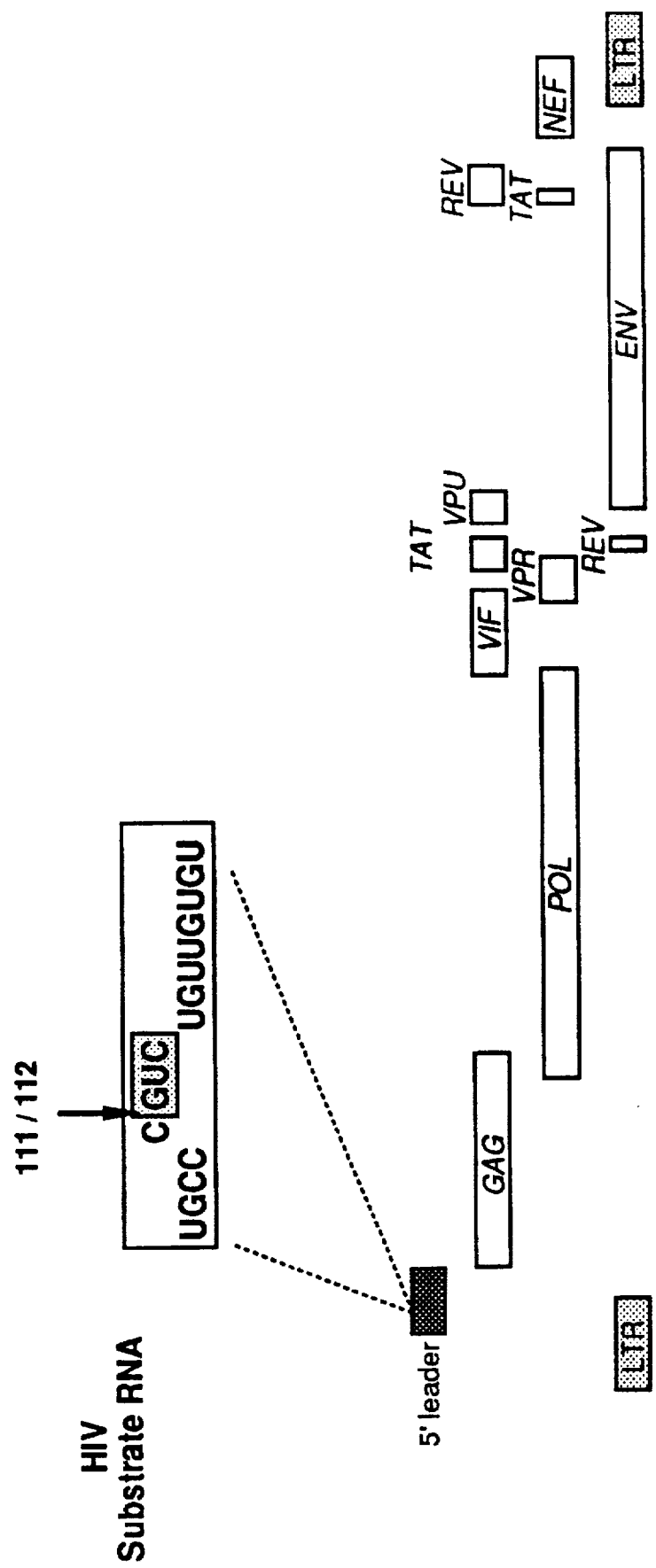
FIG. 28: HIV-1 target sequence.

FIG. 28: HIV-1 target sequence. The 16-base target sequence is found in the 5'-leader region of all 9 HIV-1 mRNAs. The nucleotide numbering starts at the first base transcribed in the HXB2 clone (HIV Sequence Data Base, prepared and distributed by Gerald Myers et al., Los Alamos National Laboratory, Los Alamos, N.Mex., telephone (505) 665-0480).

FIG. 29: Conservation of the HIV-1 target sequence in various HIV isolates. All sequences are from the HIV Sequence Data Base and are listed 5'→3'. All homologies are +107 to capsite (+1), except MAL which is +105. The capsite sequence searched for was GGT CTC TCT. Only two isolates (MAL and MN) had variations in the target sequence, and the variations were, in each case, a single base change (G→A). In the figure, cg indicates that the complete genome was contained in the sequence file, and "----" indicates proviral DNA without any homology which contained sequence information that started too late or ended too soon. It is likely that a homologous sequence does indeed occur in these strains.

Figure 30:
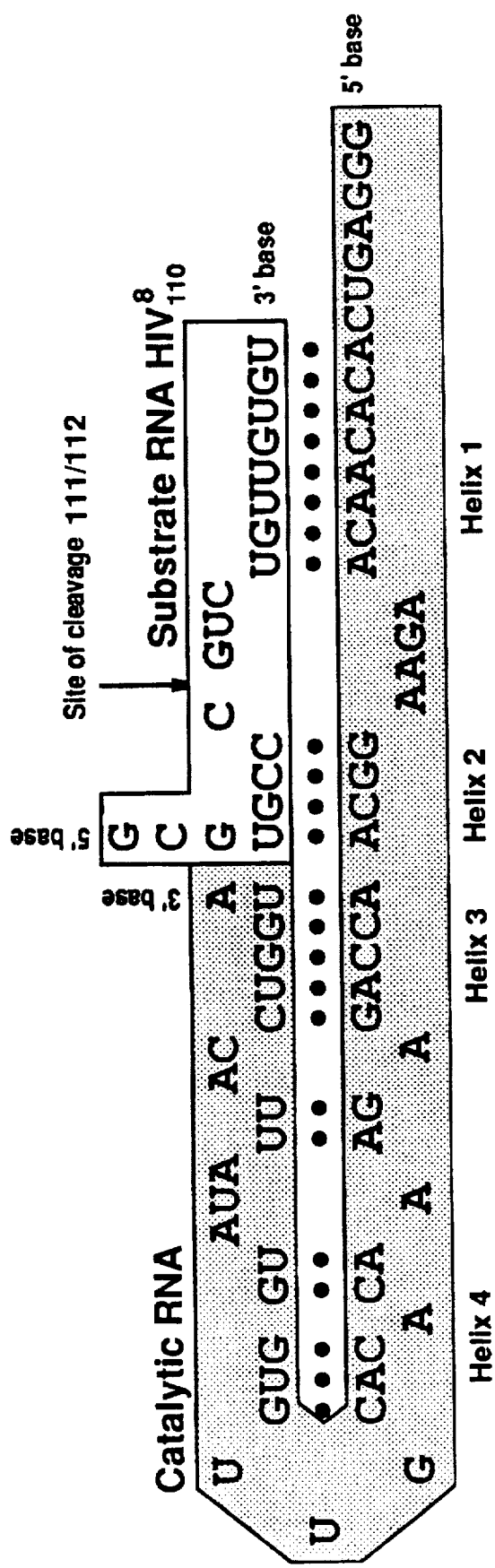
FIG. 30: Sequences of HIV-1 substrate ("SHIV") (SEQ ID NO 83) containing the conserved target sequence and of an engineered "hairpin" catalytic RNA ("RHIV") (SEQ ID NO 82) designed to cleave the substrate.

FIG. 30: Sequence of HIV-1 substrate ("SHIV") having the target sequence of FIG. 28 plus additional GCG vector bases at its 5' end. Also shown is the sequence of engineered "hairpin" catalytic RNA ("RHIV") designed to cleave this substrate. The catalytic RNA also has additional 5' vector bases 3'-CUGAGGG-5' as shown.

Figure 31A:
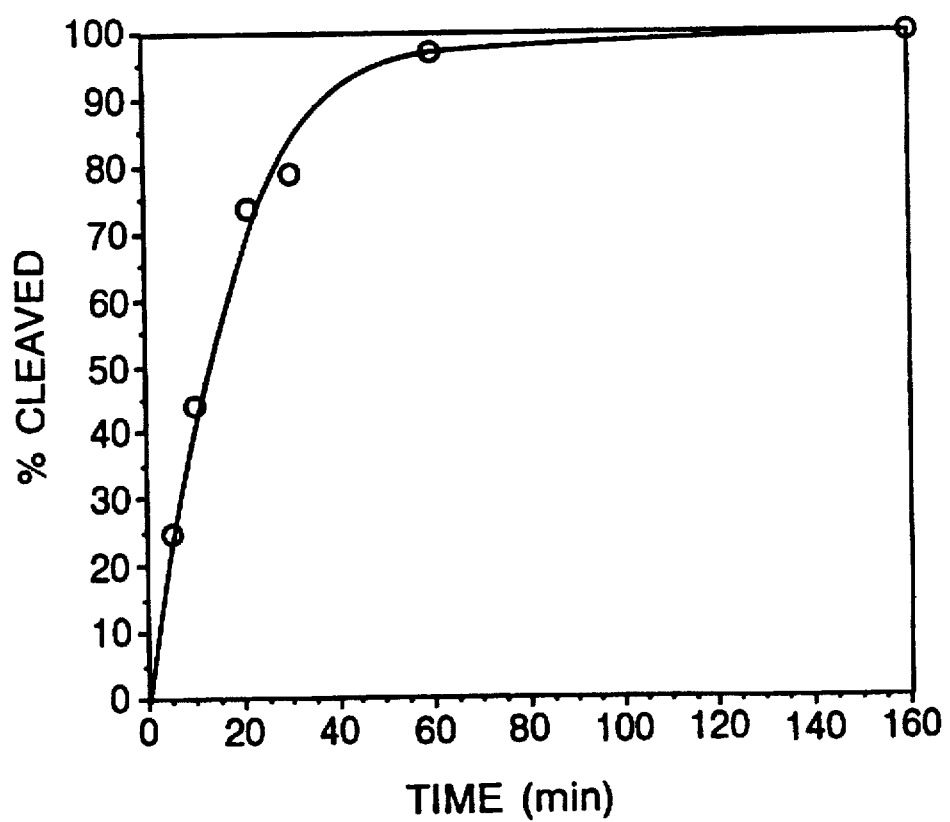

FIGS. 31A–31B: Time course of cleavage of the substrate RNA SHIV by RHIV (both depicted in FIG. 30). Shown are the catalytic RNA RHIV (R), substrate RNA SHIV (S), 3' cleavage fragment (3'F), and 5' cleavage fragment (5'F). Since 35% of the substrate was uncleavable, the remaining 65% was normalized to 100% on the ordinate of the graph.

Figure 32A:
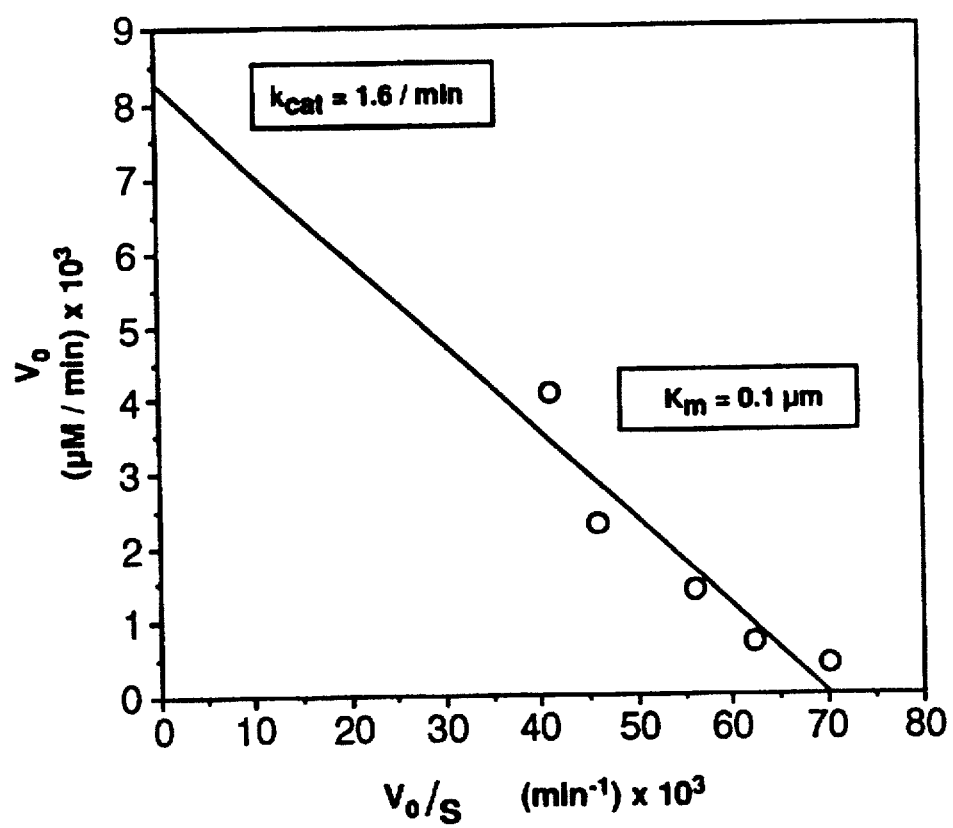

FIGS. 32A–32B: Kinetics of the cleavage of the substrate RNA SHIV by RHIV (both depicted in FIG. 30). Shown are the catalytic RNA RHIV (R), substrate RNA SHIV (S), 3' cleavage fragment (3'F), and 5' cleavage fragment (5'F). The incubation time was 5 minutes, and the concentration of RHIV was 0.005 uM. The concentration of SHIV was: Lane 1—0.10 uM; Lane 2—0.05 uM; Lane 3—0.025 uM; Lane 4—0.012 uM; Lane 5—0.006 uM; and Lane 6—0.025 uM (this is control lane at zero time). From the graph, the Km was found to be 100 nM, and the kcat to be 1.6/min. From the time course shown in FIGS. 31A–31B, it was determined that 35% of the substrate was uncleavable. This was subtracted from these calculations.

Figure 33A:
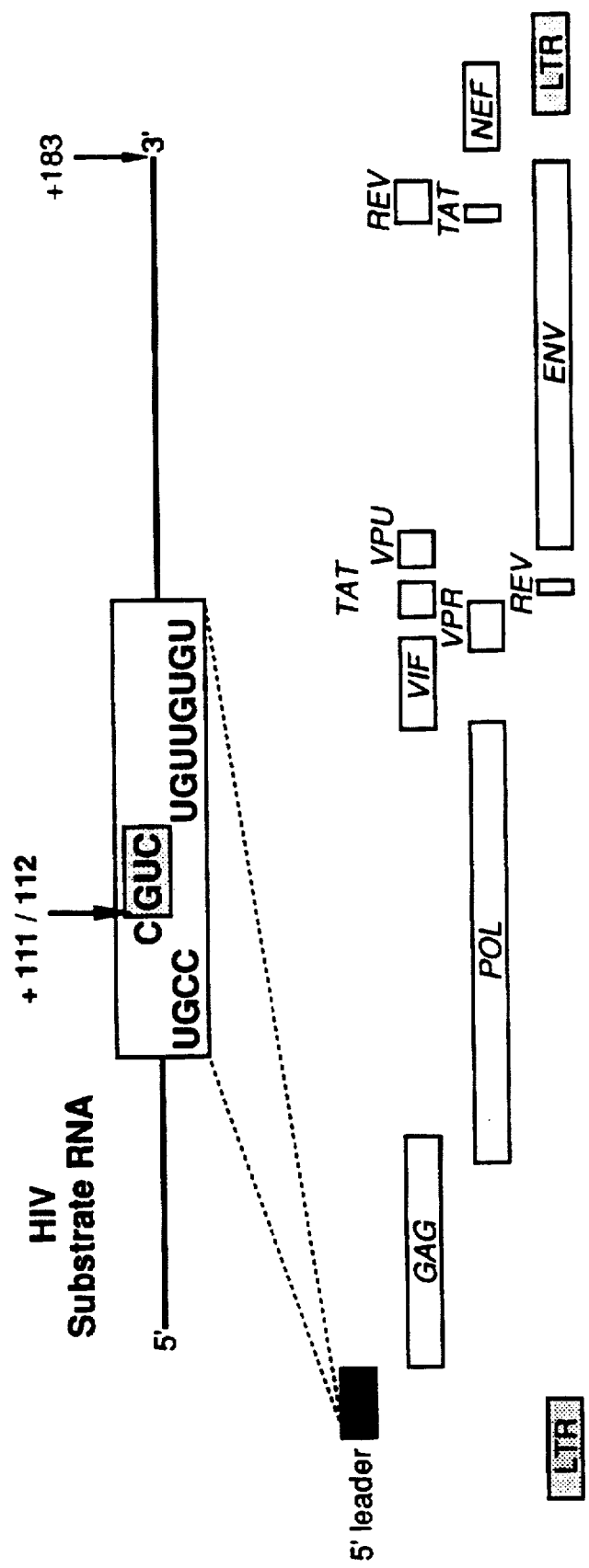
FIGS. 33A–33B: Sequence of longer HIV-1 transcript and results of its cleavage by RHIV.
Figure 33B:
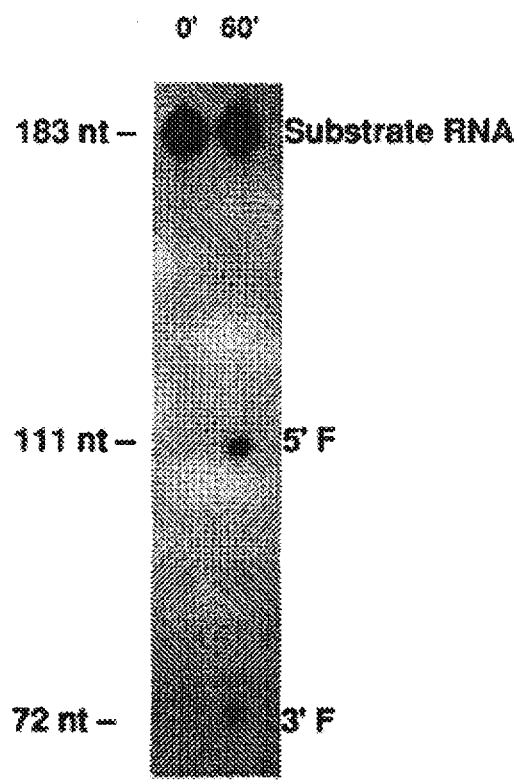

FIGS. 33A–33B: Sequence of longer HIV-1 transcript and results of its cleavage by RHIV. Shown on the gel are the uncleaved transcript of 183 nt and the two cleavage products (5'F of 111 nt and 3'F of 72 nt). The control lane at 0 minutes showed no cleavage. The gel was calibrated with standards, and all mobilities were as expected.

Figure 34A:
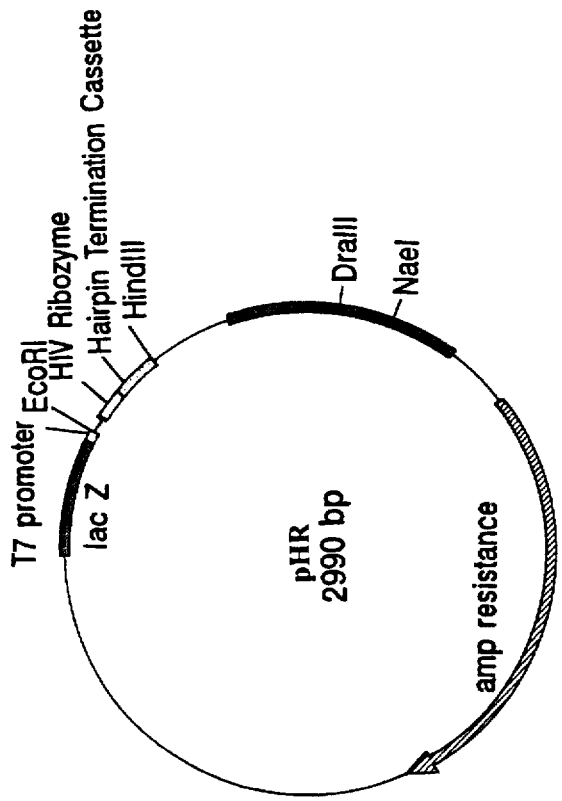
FIGS. 34A–34B: Map of pHR and partial sequence (SEQ ID NO 84).
Figure 34B:
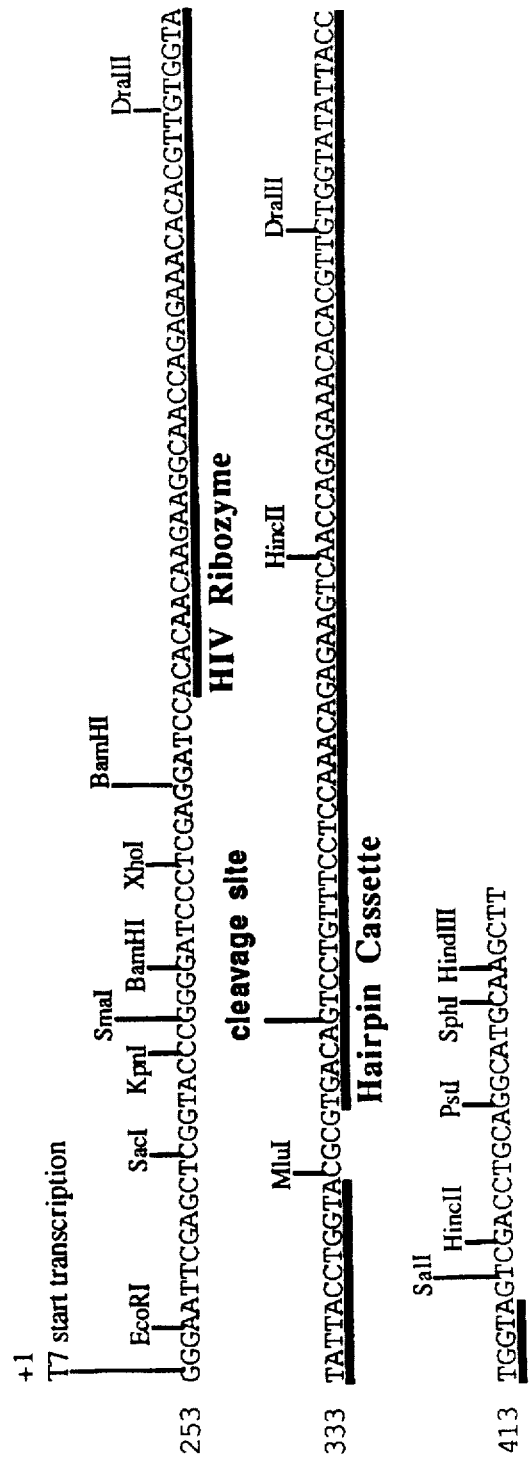

FIGS. 34A–34B: Map of pHR and partial sequence.

FIG. 35: Results of cleavage of the substrate SHIV by the 101 nt catalytic RNA (designated as "PRHIV") produced by T7 RNA polymerase transcription of pHR. Shown on the gel are RHIV (R), PRHIV (PR), SHIV (S), 3' cleavage fragment (3'F), and 5' cleavage fragment (5'F). Times of incubation were 0 and 15 minutes.

Figure 36:
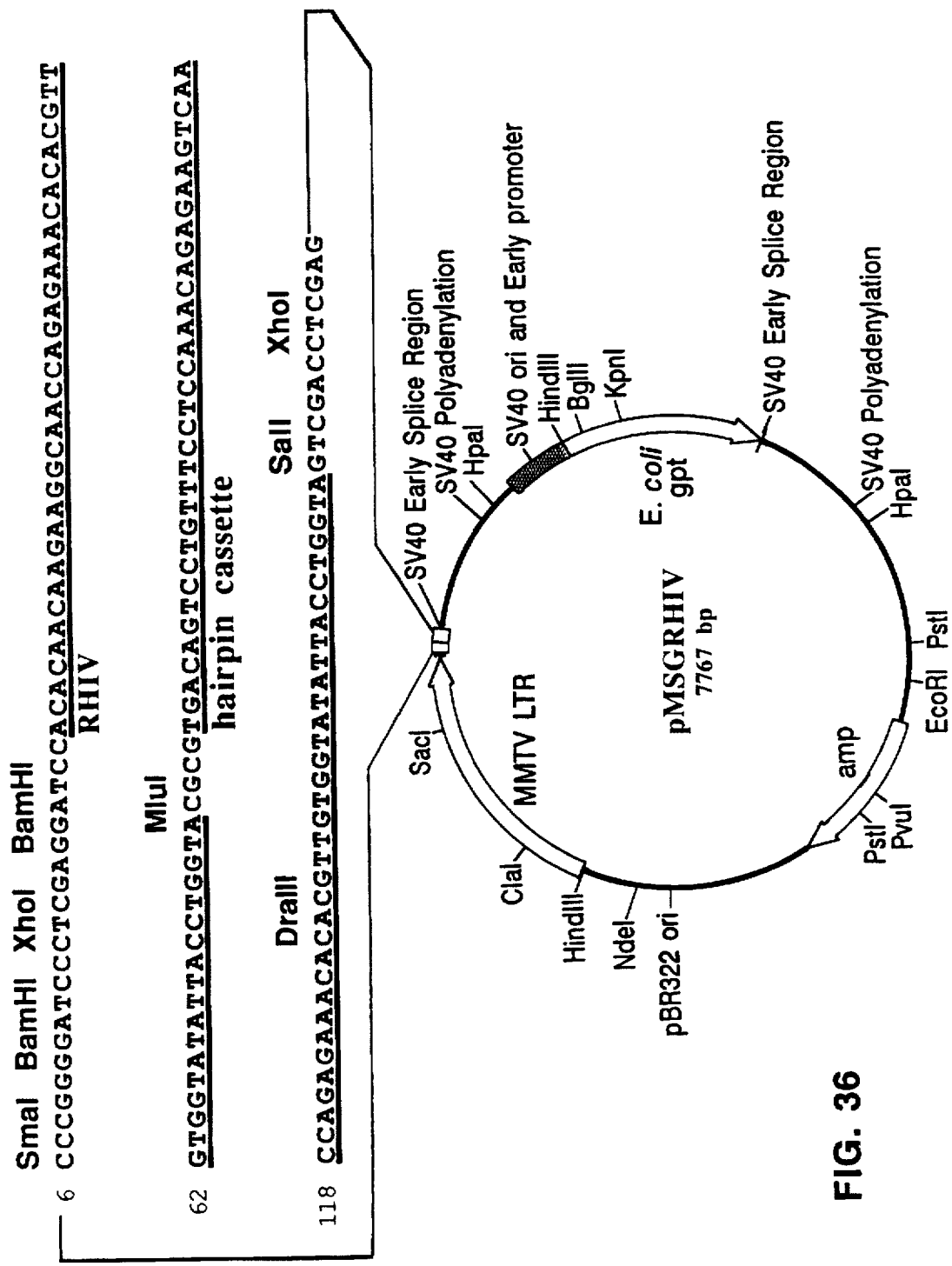
FIG. 36: Map of pMSGRHIV and partial sequence (SEQ ID NO 85).

FIG. 36: Map of pMSGRHIV and partial sequence.

Figure 37:
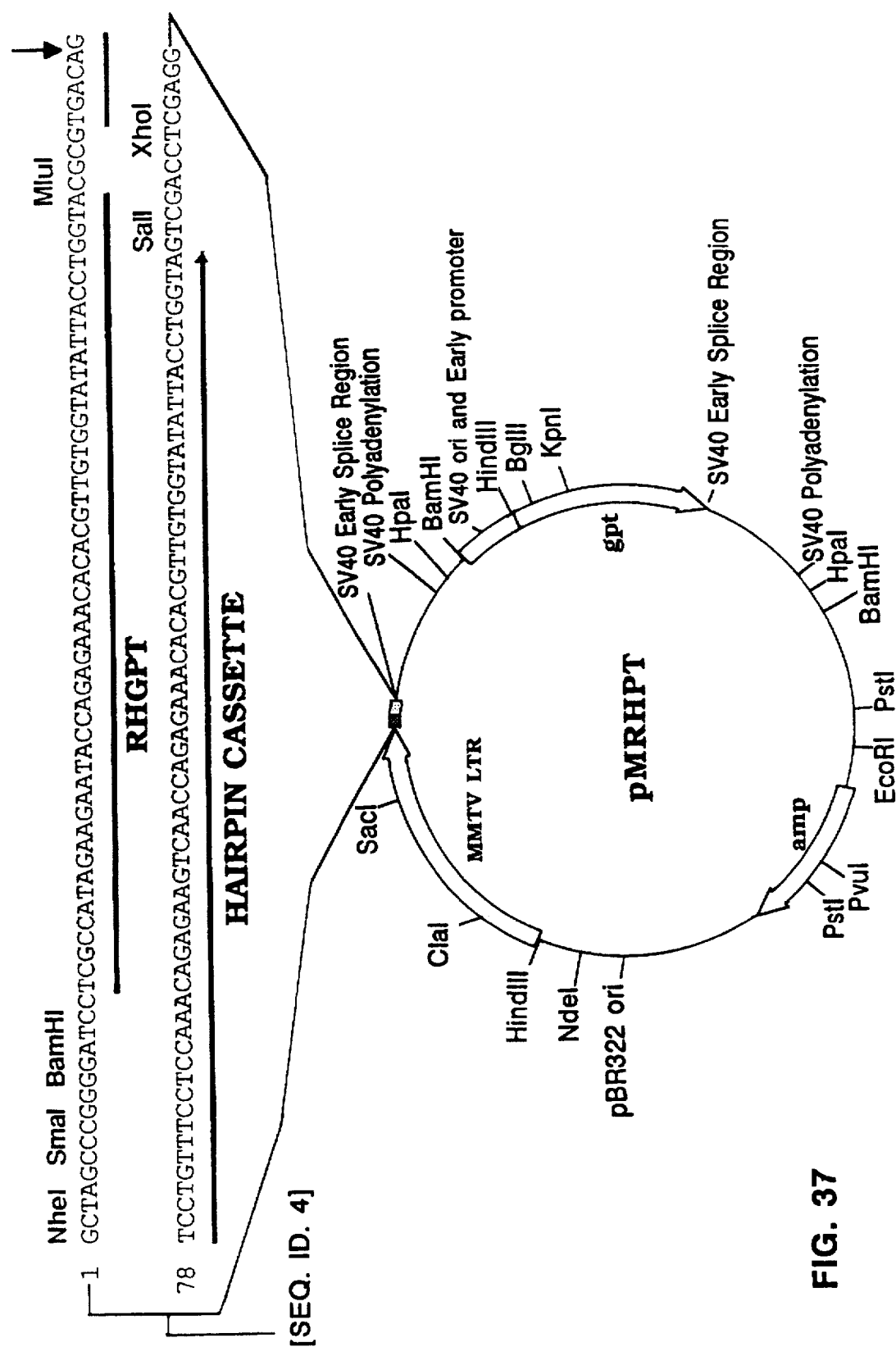
FIG. 37: Map of plasmid pMRHPT and partial sequence (SEQ ID NO 86).

FIG. 37: Map of plasmid pMRHPT. This mammalian expression vector contains DNA encoding an engineered "hairpin" catalytic RNA ("RHGPT") under control of the dexamethasone-inducible MMTV promoter and terminated by the "hairpin" autocatalytic cassette.

Figure 38:
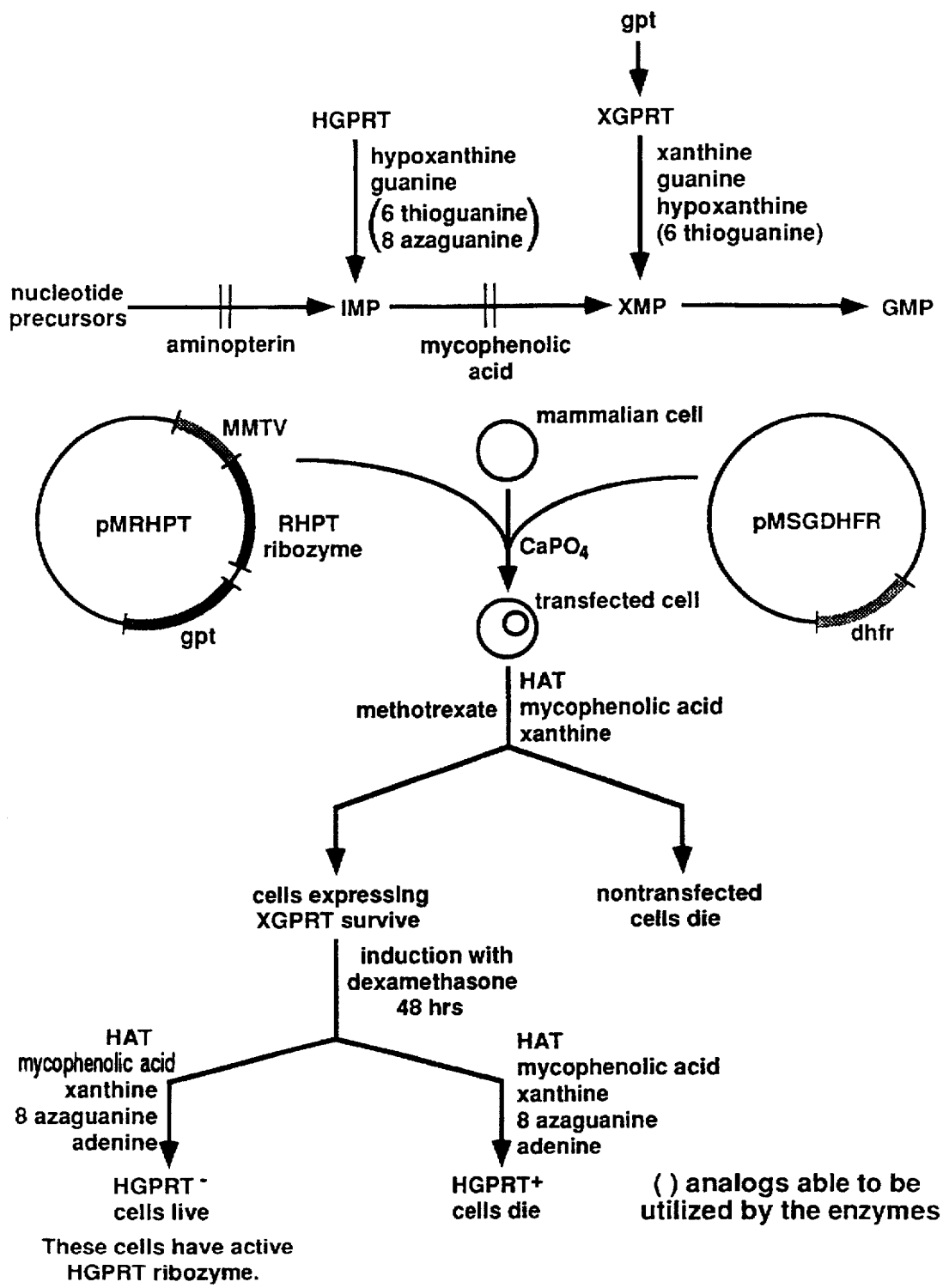
FIG. 38: Selection and testing scheme for RHGPT.

FIG. 38: Selection and testing scheme for RHGPT.

Figure 39:
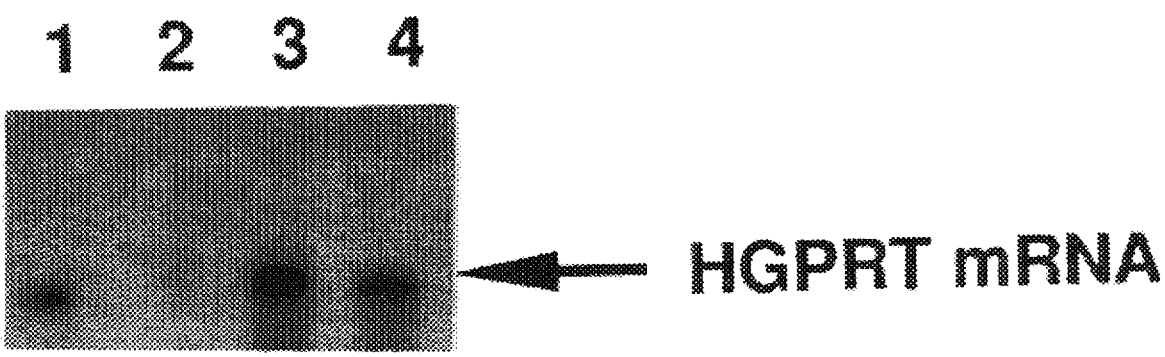
FIG. 39: Results of S1 nuclease assay for reduction of HGPRT mRNA in CHO cells transfected with pMRHPT and pMSG-dhfr.

FIG. 39: Results of S1 nuclease assay for reduction of HGPRT mRNA in CHO cells transfected with pMRHPT and pMSG-dhfr. Lane 1 contains the $P^{32}$-labelled 148 nt probe which hybridizes to HGPRT mRNA; Lane 2 contains $P^{32}$-labelled "hairpin" autocatalytic RNA used as a standard (seen only on longer exposures); Lanes 3 and 4 contain S1-nuclease digested RNA isolated from cells transformed with pMRHPT and pMSG-dhfr and induced (Lane 4) or not induced (Lane 3) with dexamethasone. The arrow shows the location of the probe-protected RNA which corresponds to HGPRT mRNA.

Figure 40:
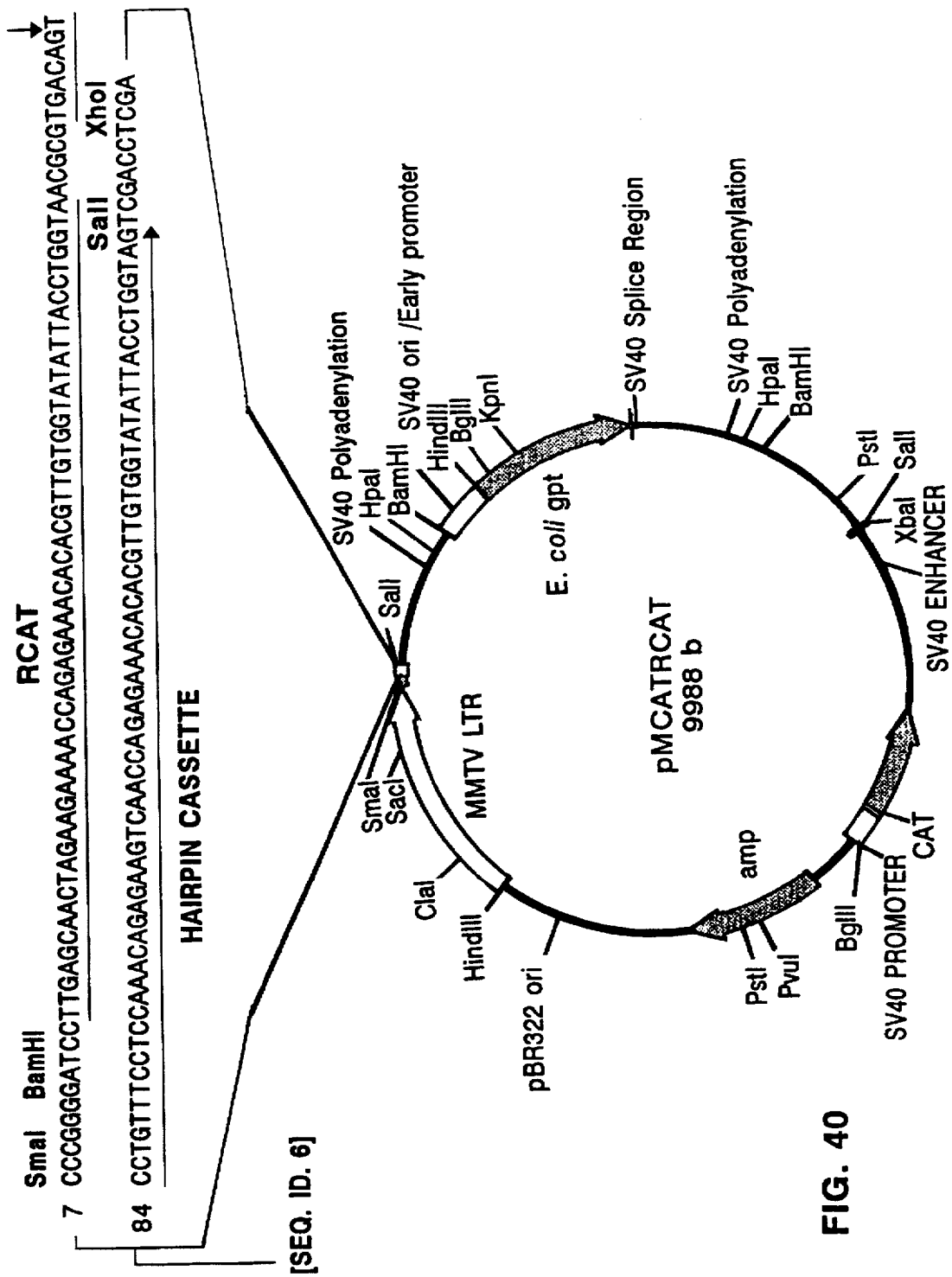
FIG. 40: Map of the plasmid pMCATRCAT and partial sequence (SEQ ID NO 87).

FIG. 40: Map of the plasmid pMCATRCAT. This plasmid contains DNA encoding a "hairpin" RNA catalyst engineered to cleave CAT mRNA operatively linked to the "hairpin" autocatalytic cassette, all driven by the dexamethasone-inducible MMTV promoter. The CAT gene is on the same plasmid and is driven by the SV40 promoter.

Figure 41:
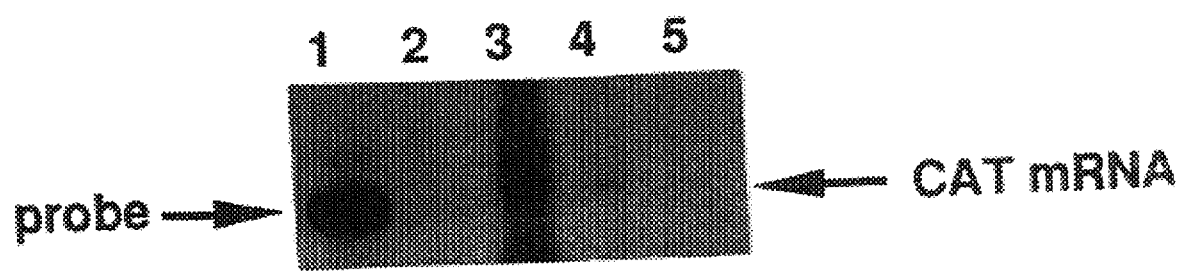
FIG. 41: Results of S1 nuclease assay for reduction of CAT mRNA in CHO cells transfected with pMCATRCAT and pMSG-dhfr.

FIG. 41: Results of S1 nuclease assay for reduction of CAT mRNA in CHO cells transfected with pMCATRCAT and pMSG-dhfr. Lane 1 contains the $P^{32}$-labelled 119 nt probe which hybridizes to CAT mRNA; Lane 2 contains RNA from untransfected CHO cells; Lane 3 contains mRNA transcribed from the CAT gene on vector pHC-CAT in vitro; Lanes 4 and 5 contain S1-nuclease digested RNA isolated from cells transfected with pMCATRCAT and pMSG-dhfr and induced (Lane 5) or not induced (Lane 4) with dexamethasone.

Figure 42A:
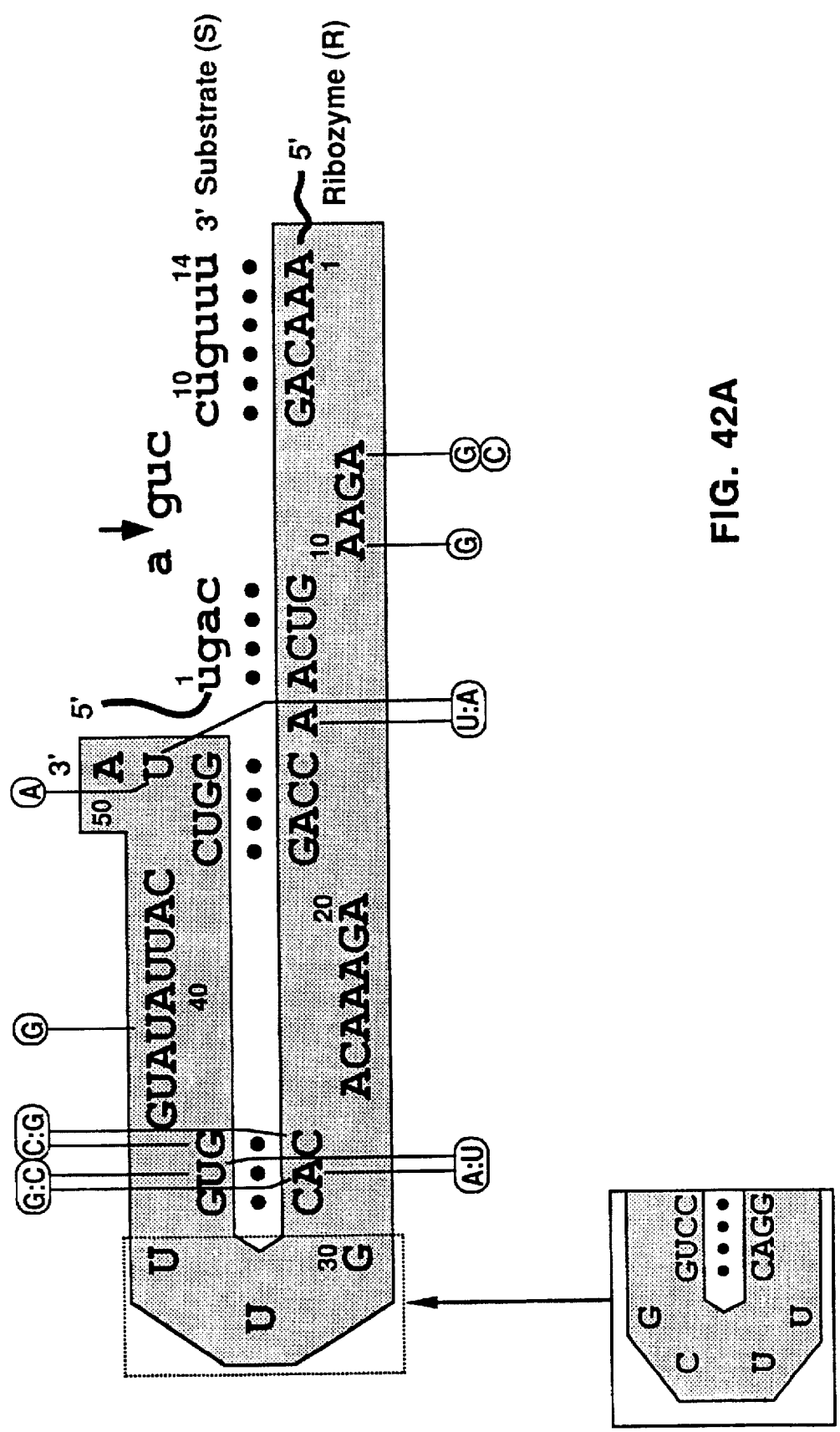
FIGS. 42A–C: Summary of mutagenesis experiments with the (−)sTRSV RNA substrate-catalyst complex (SEQ ID NO 57).
Figure 42B:
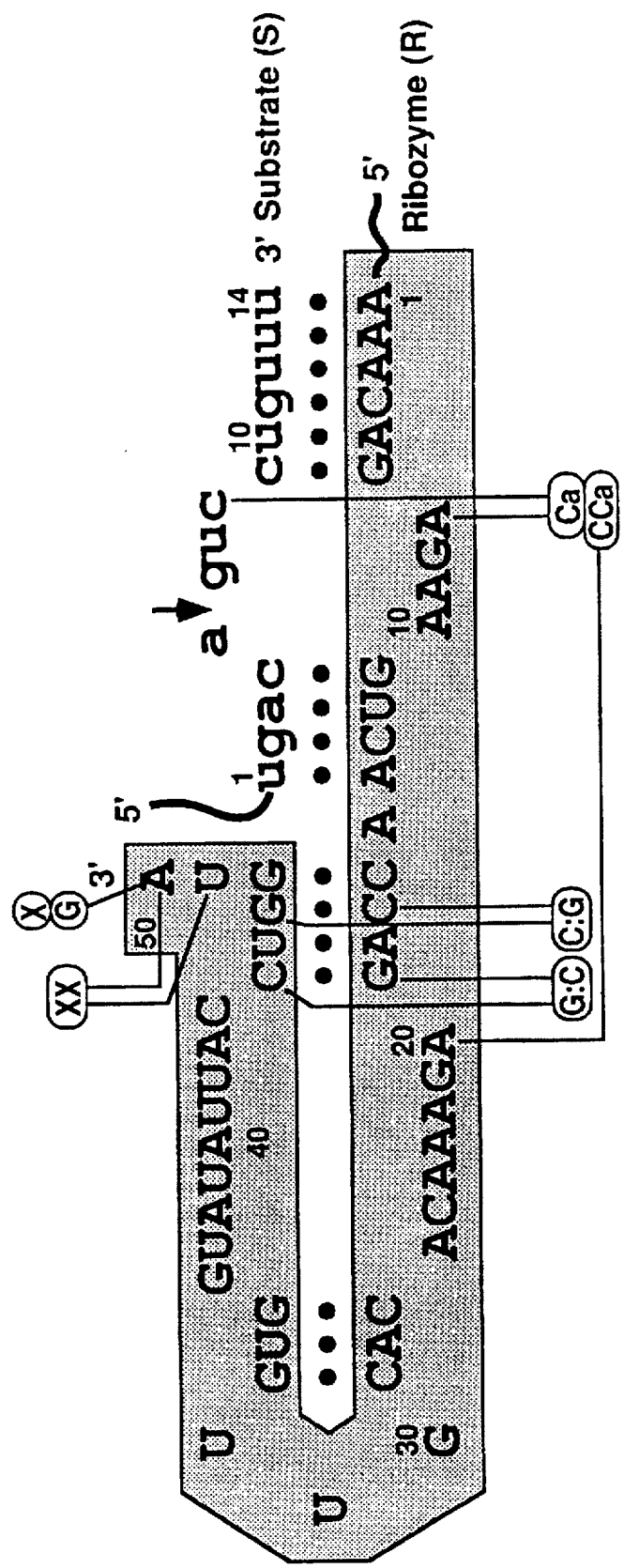
Figure 42C:
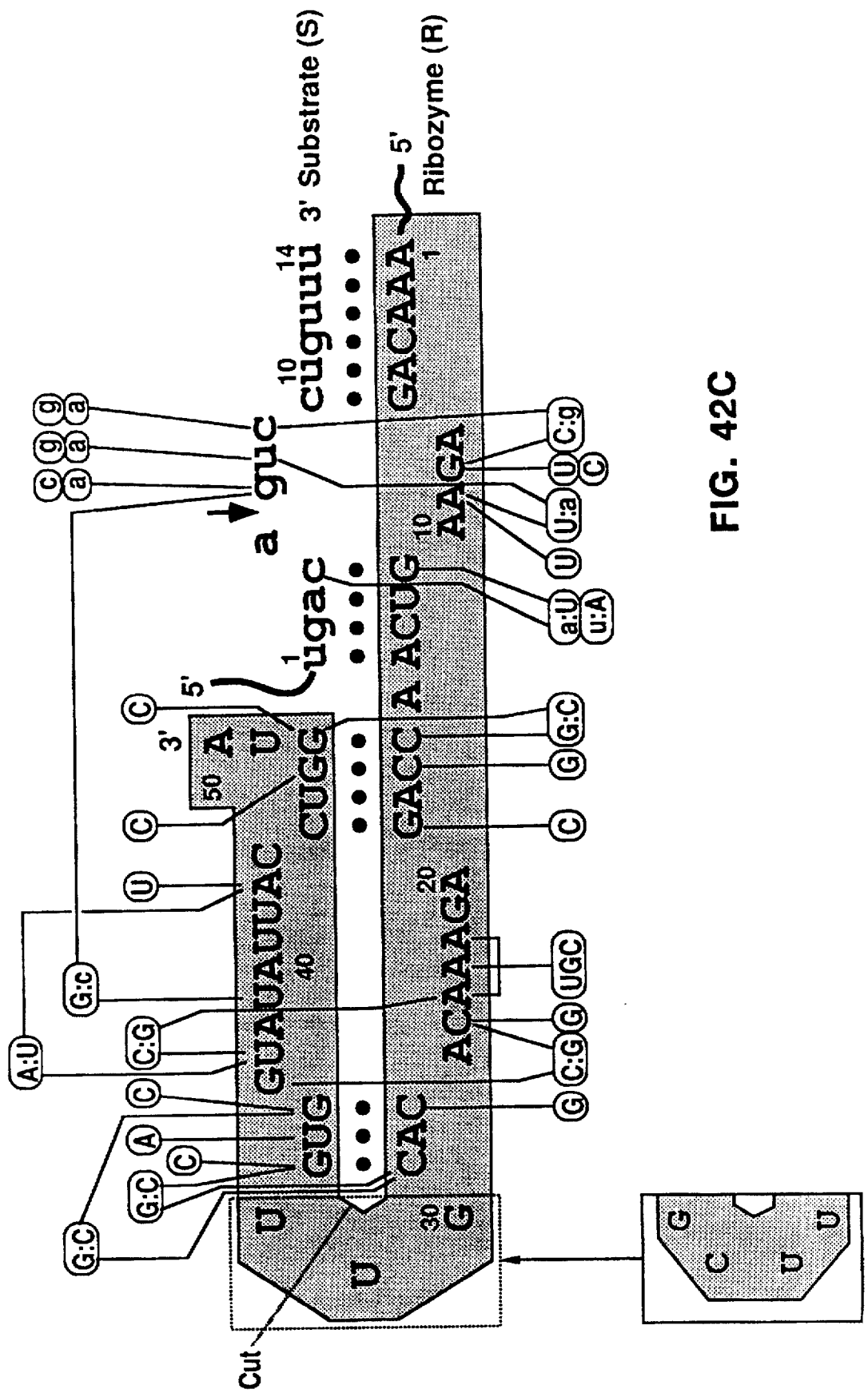

FIGS. 42A–C: Summary of mutagenesis experiments with the (-)sTRSV "hairpin" substrate-catalyst complex. Each base or combination of bases enclosed in a circle represents a separate mutational experiment.

Figure 42D:
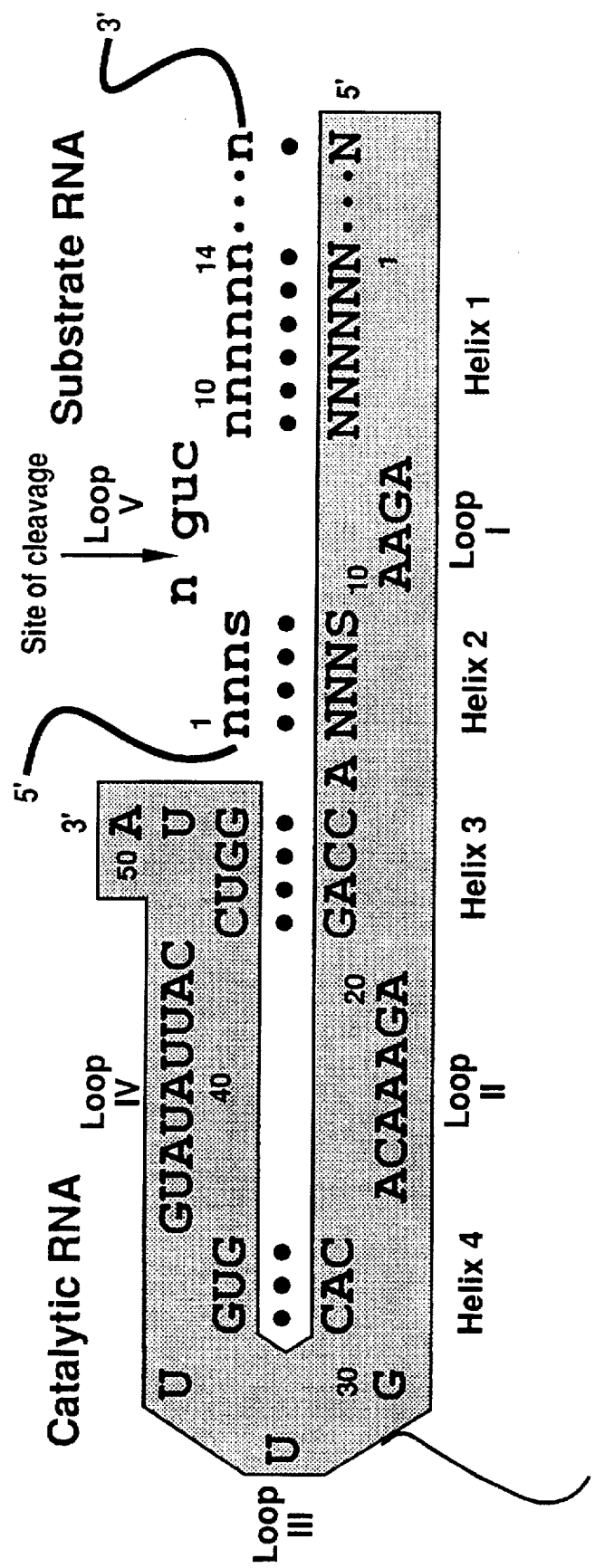
FIG. 42D: A more refined secondary structure model for the (−)sTRSV RNA substrate-catalyst complex.

FIG. 42D: A more refined secondary structure model for the (-)sTRSV "hairpin" substrate-catalyst complex.

Figure 43:
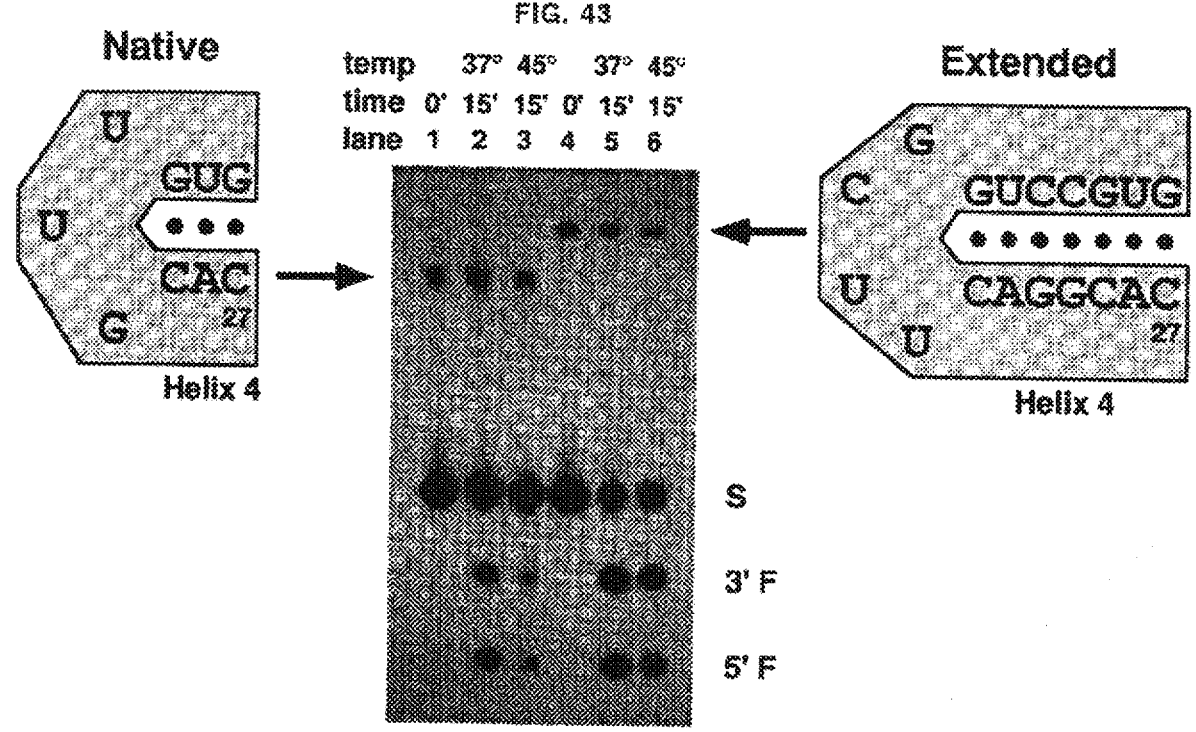
FIG. 43: Separation patterns on an acrylamide gel of the reaction products obtained by reacting substrate with "hairpin" catalytic RNA having the loop that closes the "hairpin" replaced by the sequence GGAC(UUCG)GUCC (SEQ ID NO 88).

FIG. 43: Separation patterns on an acrylamide gel of the reaction products obtained by reacting substrate with a "hairpin" catalytic RNA having the loop that closes the "hairpin" replaced by the hairpin sequence GGAC(UUCG)GUCC (SEQ ID NO 1).

DESCRIPTION OF THE PRESENTLY PREFERRED EMBODIMENTS

An RNA catalyst has been identified comprising an RNA sequence which can be engineered to cut, with great precision, target RNAs having a cleavage sequence. In particular, the invention comprises certain synthetic RNA catalysts capable of cleaving an RNA substrate which contains the target sequence 5'-$F_1$-CS-$F_2$-3'.

"Synthetic RNA catalyst," as used herein, means a catalyst which is not a naturally-occurring RNA catalyst, although "synthetic catalysts" may be truncated or altered versions of naturally-occurring catalysts. "Synthetic catalysts" are catalysts designed according to the principles set forth herein based on the "hairpin" model to bind to and cleave a selected target sequence in a selected RNA substrate. "Synthetic catalysts" are also sometimes referred to herein as "engineered catalysts." "Synthetic catalysts" include catalysts synthesized in vitro and catalysts synthesized in vivo. In particular, "synthetic catalysts" include catalysts produced by hosts transformed by a vector comprising a sequence coding for the catalyst.

RNA of any length and type may be used as the substrate as long as it contains the 5'-$F_1$-CS-$F_2$-3' target sequence. In this formula, CS is the cleavage sequence (i.e., a sequence of bases containing the site at which the catalyst cleaves the substrate). CS is a short sequence of bases which does not base pair with the RNA catalyst, and CS preferably has the sequence 5'-NGUC-3', wherein N is any base, and the substrate is cleaved by the catalyst between N and G to produce a fragment having an OH at the 5' end and a fragment having a 2, '3' cyclic phosphate at the 3' end.

CS is flanked by two short base sequences $F_1$, and $F_2$ which do base pair with the RNA catalyst. $F_1$, is preferably at least 3 bases in length, most preferably 4 bases in length. $F_2$ is also preferably at least 3 bases in length, most preferably 6 to 12 bases in length.

Catalysts according to the invention comprise a substrate binding portion and a "hairpin" portion. The substrate binding portion of the catalyst has the sequence:

3'$F_4$-$L_1$-$F_3$-5' wherein, $F_3$ is a sequence of bases selected so that $F_3$ is substantially base paired with $F_2$ when the catalyst is bound to the substrate;

$F_4$ is a sequence of bases selected so that $F_4$ is substantially base paired with $F_1$, when the catalyst is bound to the substrate;

the sequences of $F_3$ and $F_4$ being selected so that each contains an adequate number of bases to achieve sufficient binding of the RNA substrate to the RNA catalyst so that cleavage of the substrate can take place; and $L_1$ is a sequence of bases selected so that $L_1$ does not base pair with CS when the catalyst is bound to the substrate.

As used herein, "substantially base paired" means that greater than 65% of the bases of the two RNA sequences in question are base paired, and preferably greater than 75% of the bases are base paired. "Substantially unpaired" means that greater than 65% of the bases of the two sequences in question are not base paired, and preferably greater than 75% of the bases are not paired.

$F_3$ is preferably at least 3 bases in length, most preferably from 6 to 12 bases in length. $F_4$ is preferably from 3 to 5 bases in length, most preferably 4 bases in length.

$L_1$ is a short sequence of bases which preferably has the sequence 5'- AGAA-3' when CS has the sequence 5'-NGUC-3'. Further, when $L_1$ is 5'-AGAA-3' and CS is 5'-NGUC-3', then the first base pair between $F_1$, and $F_4$ adjacent to CS and $L_1$ is preferably G:C or C:G (see FIG. 42D and Example 32). Accordingly, a preferred target sequence in a selected substrate contains the sequence 5'-SNGUC-3', wherein S is G or C.

The "hairpin" portion is a portion of the catalyst which folds into a hairpin-like configuration when the substrate-catalyst complex is modeled in two dimensions for minimum energy folding. This is shown in FIGS. 1 and 42D for (-)sTRSV RNA. The "hairpin" portion is not an absolute hairpin in the sense that not all bases of the "hairpin" portion are base-paired. Indeed, it is preferable, perhaps necessary, for the "hairpin" portion to have at least one substantially unpaired region so that the catalyst can assume a tertiary structure that allows for better, or optimal, catalytic activity.

The "hairpin" portion of the catalyst preferably has the sequence:

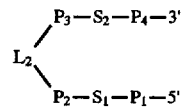

wherein, $P_1$ and $P_4$ each is a sequence of bases, the sequences of $P_1$ and $P_4$ being selected so that $P_1$ and $P_4$ are substantially base paired;

$P_1$ is covalently attached to $F_4$;

$S_1$ and $S_2$ each is a sequence of bases, the sequences of $S_1$ and $S_2$ being selected so that $S_1$ and $S_2$ are substantially unpaired;

$P_2$ and $P_3$ each is a sequence of bases, the sequences of $P_2$ and $P_3$ being selected so that $P_2$ and $P_3$ are substantially base paired; and $L_2$ is a sequence of unpaired bases.

"Substantially base paired" and "substantially unpaired" have the same meanings as discussed above.

$P_1$ and $P_4$ each is preferably from 3 to 6 bases in length, and most preferably $P_1$ has the sequence 5'-ACCAG-3' and $P_4$ has the sequence 5'- CUGGUA-3'. It has been found that the A at the 5' end of 5'-ACCAG-3' (underlined) is not base paired to the U at the 3' end of 5'-CUGGUA-3' (underlined), and the unpaired A may act as a "hinge" (see Example 32). It is not known yet, but the presence of such a "hinge" may be necessary for catalytic activity.

$S_1$ and $S_2$ each preferably is from 4 to 9 bases in length, and most preferably $S_1$ has the sequence 5'-AGAAACA-3' and $S_2$ has the sequence 5'-GUAUAUUAC-3'.

$P_2$ and $P_3$ each is preferably from 3 to 9 bases in length, and more preferably $P_2$ has the sequence 5'-CAC-3' and $P_3$ has the sequence 5'-GUG-3'.

Finally, $L_2$ is preferably at least 3 bases in length and preferably has the sequence 5'-GUU-3'. Further, 5'-$S_1$-$P_2$-$L_2$-3' preferably has the sequence 5'-AGAAACACACGUU-3' (SEQ ID NO 4).

The specific preferred sequences set forth above for $P_1$, $P_2$, $S_1$, etc., are from the catalytic sequence of (−)sTRSV RNA.

A preferred catalyst according to the invention contains the sequence:

5'-$F_3$-$L_1$-$F_4$-ACCAGAGAAACACACGUUG-UGGUAUAUUACCUGGUA-3' (SEQ ID NO 5), and active variants thereof, wherein $F_3$, $F_4$ and $L_1$ are as defined above. As used herein "active variants" means catalysts which, although having substitutions, deletions and/or additions of bases as compared to the original sequence, are still capable of cleaving an RNA substrate.

The most preferred sequence for 5'-$P_2$-$L_2$-$P_3$-3' is 5'-CACGGACUUCGGUCCGUG-3' (SEQ ID NO 6) [SEQ ID 46] (see Example 32). Accordingly, the most preferred catalyst has the sequence:

5'-$F_3$-$L_1$-$F_4$-ACCAGAGAAACA<u>CACGGACUUCGGUCCGUG</u>GUAUAUUACCUG-GUA-3'[SEQ ID 47]

wherein $F_3$, $F_4$ and $L_1$ are as defined above and the underlined portion is the preferred sequence for $P_2$-$L_2$-$P_3$.

Another preferred catalyst according to the invention is an autocatalytic catalyst containing the sequence:

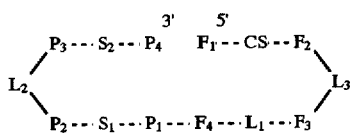

wherein, $F_1$, $F_2$, $F_3$, $F_4$, $L_1$, $L_2$, $S_1$, $S_2$, $P_1$, $P_2$, $P_3$ and $P_4$ are as defined above. $L_3$ is a sequence of unpaired bases, and $L_3$ preferably has the sequence 3'-CCUCC-5'. Thus, the molecule contains a substrate portion (5'-$F_1$-CS-$F_2$-3') and a catalytic portion (5'-$F_3$-$L_1$-$F_4$-$P_1$-$S_1$-$P_2$-$L_2$-$P_3$-$S_2$-$P_4$-3') covalently linked together by $L_3$ so as to produce a synthetic autocatalytic RNA catalyst.

After being transcribed, this catalyst will spontaneously undergo an intramolecular autocatalytic cleavage at CS. The effect of this intramolecular cleavage is to autocatalytically terminate any RNA transcript in which the sequence is inserted. For instance, an engineered DNA molecule may be prepared which comprises a gene of interest and a DNA sequence coding for the catalyst linked so that, when transcribed, the catalyst will terminate transcription of the messenger RNA coding for the gene product at a desired location.

The invention further provides an engineered DNA molecule and a vector comprising a DNA sequence coding for an RNA catalyst of the invention. Also provided are host cells which have been transformed with the vectors and which are capable of expressing the RNA catalyst. Finally, the invention provides a method of cleaving an RNA substrate which contains the sequence 5'-$F_1$-CS-$F_2$-3', the method comprising contacting the substrate with a synthetic RNA catalyst according to the invention.

The invention is further described below with particular reference to the catalytic properties of (−)sTRSV RNA and the structure of its catalytic complex, but the invention is not limited to synthetic catalysts based on (−)sTRSV RNA. In addition to the particular catalytic sequences shown and described below, other RNA molecules having catalytic activity to cleave an RNA substrate can be readily found by applying the principles set forth in this specification.

For example, RNA sequences having the required structural features for cleaving an RNA substrate can be identified by applying the Wisconsin RNA Folding Program discussed above to (1) known sequences of molecules having catalytic or autocatalytic activity (especially molecules in which the actual location of the catalytic site is unknown), (2) randomly generated sequences having the proper pairing regions and lengths, and (3) randomly modified known catalytic sequences, while looking for known features of a catalytic molecule, such as the "hairpin" configuration of the catalytic complex when modeled in two dimensions. As a specific example, information regarding known autocatalytic cleavage sites can be used to find substrate binding sequences having the properties described above, such as having a substrate binding sequence adjacent a "hairpin" portion. Secondary features, such as the two substantially paired regions in the "hairpin" portion, with an intermediate substantially unpaired region and an appropriate base loop can then be looked for, either by manual examination or with automated computer programs. In order of decreasing preference, the following features are considered important in selecting a catalytic sequence: (1) regions that can base pair (form helices) with the regions of the substrate RNA molecule flanking the cleavage sequence; (2) an unpaired (loop) region opposite the cleavage sequence of the substrate RNA; (3) two substantially base paired regions in a "hairpin" structure near the cleavage sequence; (4) a substantially unpaired region between these two substantially paired regions in the "hairpin" structure; and (5) a loop connecting the two strands of a substantially base paired region to complete the "hairpin" structure. Standard techniques of in vitro RNA synthesis can then be used to prepare actual molecules having the sequence that gives the predicted two-dimensional computer-generated structure for verification of activity and routine testing of variation to determine optimum sequence.

The catalysts of the present invention were developed using a "hairpin" model or motif of RNA catalysis. According to this model, the catalytic complex, when modeled in two dimensions for minimum energy folding, assumes a "hairpin" configuration. This is shown in FIGS. 1 and 42D for (−)sTRSV RNA. The catalytic complex is a complex of the minimum, or substantially the minimum, sequence of the catalyst necessary for activity and the minimum, or substantially the minimum, target sequence of the substrate. The "hairpin" configuration is not an absolute hairpin in the sense that not all the bases that make up this "hairpin" configuration are base-paired. Indeed, there are preferably regions of unpaired bases and of substantially unpaired bases as discussed in detail elsewhere in the present application.

The "hairpin" model has proved very useful in designing new catalysts, but it is still only a computer model of the likely secondary structure of catalytic complexes involving catalysts according to the present invention. Also, it is ultimately the tertiary structure of RNA catalysts that determines their activity. For these reasons, all catalysts having the properties described herein are considered to come within the scope of the present invention, even if they do not form a "hairpin" configuration when complexed with the substrate and even if they do not contain a "hairpin" portion. For instance, it may be possible to engineer a catalyst having the properties described herein which does not have a loop $L_2$. Such a catalyst would be considered to be fully equivalent to the catalysts described and claimed herein.

As described in Example 1, a catalytic complex was identified within the (−) strand of tobacco ringspot virus satellite RNA (sTRSV) when the molecule was folded using computer models to determine the minimum energy folding in two-dimensional space. The (−) strand is a 359 base long RNA of defined sequence and is known to have autocatalytic properties (Gerlach, W. L., Buzayan, J. W., Schneider, I. R. and Bruening, G. B. (1986) *Virology*, 151: 172–185; Buzayan, J. M., Gerlach, W. and Bruening, G. (1986) *Nature*, 323: 349–352). The (−) strand cleaves at a defined site (ApG) into a cleavage product having an OH at the 5' end and a 2', 3' cyclic phosphate at the 3' end. Up until the present time, however, little work had been done with the (−) strand to find the catalytic complex and to determine the minimum cleavage sequences because it does not fit the consensus "hammerhead" model.

In view of the above and the fact that the catalytic center would contain both the catalytic RNA sequence and the substrate (target) RNA sequence and by studying the results of Example 1, a 50 nucleotide sequence between bases 175 and 224 was picked and a 14 nucleotide sequence between bases 40 and 53 was picked. Using methodologies found in published procedures, a catalytic RNA having a satellite RNA base sequence identical to the base sequence in naturally-occurring (−)sTRSV between bases 175 and 224 was transcribed from chemically synthesized DNA templates using T7 RNA polymerase as described in Example 2. An RNA substrate having a satellite RNA base sequence identical to the base sequence in naturally occurring (−)sTRSV RNA between bases 40 and 53 was also prepared in the same manner. When the newly synthesized RNAs were mixed together under appropriate conditions as described in Example 3, the catalytic RNA cleaved the substrate RNA. As described in Example 4, the first RNA catalyst fitting the "hairpin" motif was discovered when the complex of the 50-base catalytic RNA and the 14-base substrate RNA was modeled in two-dimensional space using computer modeling.

The reaction of catalysts fitting the "hairpin" motif with an appropriate substrate proved to be an excellent catalytic reaction under physiological conditions. The reaction of the catalyst and substrate containing the sequences of (−)sTRSV shown in FIG. 1 gave a Km of 0.03 uM (see Example 5), which is 20 times smaller than that of the Km for a catalyst fitting the "hammerhead" model (Uhlenbeck, O. C. (1987) Nature 328: 596–600) and accounts for its ability to remove target RNA molecules to much lower levels (20 times lower) than that of catalysts fitting the "hammerhead" model. In addition, the kcat for the reaction is 2.1/min at 37° C., which is at least 6 times greater than that of a catalyst having the "hammerhead" configuration at the same temperature (see Example 5). These reaction parameters for a catalyst that fits the "hairpin" model can be optimized by adjusting the amount of base pairing between the substrate and catalyst (see Examples 18, 21 and 32).

Catalytic cleavage of the substrate RNA occurs over a broad pH range, preferably 5.5 to 8.0, and in the presence of divalent ions such as Mg++, e.g. from $MgCl_2$. As would be expected for a base catalyzed reaction, the rate of reaction increased with increasing pH. The reaction rate also increased with increasing concentration of divalent cations as shown in Example 8.

The reaction takes place at physiological temperatures, preferably 16° C. to 45° C., with a temperature optimum at 37° C. as described in Example 6. Temperatures above about 45° C. inactivate the reaction. However, the temperature optimum of the reaction is affected by the degree of base pairing between the substrate and catalyst (see Example 18). In particular, the length of the region of the catalyst that base pairs with the 3' region of the substrate flanking the cleavage sequence can be varied so that an engineered catalyst reacting at a desired temperature can be obtained (see Example 18). Further, a "hairpin" catalyst which is more thermal stable than the native (−)sTRSV catalyst can be prepared by deleting the loop that closes the "hairpin" (Loop III in FIG. 42D) and inserting therefor the stable hairpin sequence 5-GGAC(UUCG)GUCC-3' [SEQ ID 1] (see Example 32).

The 50 base catalytic RNA configured in the "hairpin" model in FIGS. 1 and 42D is the minimal sequence, or substantially the minimal sequence, of (−)sTRSV RNA necessary to achieve catalysis. When the 3' terminal A (base 175) or AU (bases 175 and 176) of this sequence was removed, catalytic activity was substantially decreased as shown in Example 10. The 5' end of the molecule cannot be substantially changed either without affecting catalytic activity because it is needed to provide base pairing with the substrate. It can be shortened by at most about 3 bases (see Example 9). Experiments which removed bases 195–203 in the center of the catalytic RNA and ligated base 194 to base 204 produced an inactive catalytic RNA as described in Example 11. This shows that all or part of the region between bases 195–203 is essential for catalytic activity. An additional mutagenesis experiment to test the base requirement of the three A bases at positions 203, 202 and 201 was done. When these bases were changed to CGU, respectively, as described in Example 12, the resulting catalytic RNA was inactive.

Base changes can be made in the two base paired regions (Helices 3 and 4 in FIG. 42D) of the "hairpin" portion of the (−)sTRSV catalytic RNA, as long as substantial base pairing is maintained. This is shown in Examples 22 and 32 where base changes that destroyed base pairing in these two regions resulted in inactive catalysts. When a second base change was made which restored base pairing, the catalytic activity was also restored (see FIGS. 19 and 42A–C). The one exception appears to be the first C:G base pair at the end of Helix 3 nearest the substrate binding portion (base pair C16:G48 in FIG. 42D). Currently available evidence indicates that the identity of these two bases must be maintained (see Example 32).

An active ribozyme is produced when Helix 4 is extended and the sequence of the loop that closes the "hairpin" (Loop III in FIG. 42D) is changed. As shown in FIG. 42A, Loop III was replaced with the common and very stable RNA hairpin sequence 5'-GGAC(UUCG)GUCC-3' (SEQ ID NO 1). As a result of this substitution, Helix 4 was extended by four base pairs and the GUU sequence of Loop III was replaced with the sequence UUCG (see FIG. 42A). The resulting RNA catalyst was more active and, as noted above, more thermally stable than the unmutated form (see Example 32). It was concluded from this experiment that Loop III does not have a conserved or unique base sequence and that Helix 4 can be extended by at least four base pairs without loss of activity.

However, the simple replacement of the GUU sequence of Loop III with the sequence UUCG gives an inactive ribozyme (see Example 32). It is believed that this shows that the sequence of Loop III has an influence on the stability of Helix 4.

When Loop III is cut between U31 and U32, activity is lost (see FIG. 42C). A likely explanation for this is that when Loop III is cut, Helix 4 opens up and catalytic activity is, consequently, lost.

Base changes can also be made in the two regions of the catalytic RNA that base pair with the substrate, as long as substantial base pairing with the substrate in the regions flanking the cleavage sequence is maintained and base pairing with the cleavage sequence is avoided as shown in Examples 9, 16–21 and 32. Indeed, every base pair in Helices 1 and 2 (see FIG. 42D) can be changed to any other base pair, except the base pair in Helix 2 adjacent to the NGUC cleavage sequence (see Example 32). This base pair must be G:C or C:G and cannot be A:U or U:A, except it is believed that this base pair is needed for stability and that A:U or U:A base pairs can be used if other measures are taken to stabilize the substrate-catalyst interaction. Indeed, it has been found that A:U and U:A base pairs can be used at these positions in the synthetic autocatalytic catalyst of the invention.

It is the ability to change the base pairs in Helices 1 and 2 that allows the RNA catalyst to be engineered to cut a specific target RNA substrate having a cleavage sequence such as NGUC. This is illustrated in Example 16 where the catalytic RNA was engineered by changing base 214 from a G to a C resulting in a catalytic RNA which failed to react with the substrate RNA developed from natural (−)sTRSV RNA. Activity was restored, however, when the substrate RNA was changed so that it could base pair with the subject engineered catalytic RNA. Also see Examples 9, 17–21 and 32.

A type of "hinge" region, consisting of a single base, seems to be present between Helices 2 and 3 of the (−)sTRSV catalytic RNA (see FIG. 42D and Example 32). The A at position 15 is not paired to the U at position 49, and the unpaired A may act as a "hinge."

Further mutation studies have showed that the substantially unpaired regions between Helices 3 and 4 (Loops II and IV in FIG. 42D) are larger than originally predicted by computer modeling and energy minimization (compare FIGS. 1 and 42D). Further, some of the bases in these loops appear to be required for activity (see Example 32). In particular, changing bases C25 and A43 results in a loss of activity (see FIG. 42C and Example 32; also see Example 12).

The (−)sTRSV catalytic RNA sequence has an 5'-AGAA-3' sequence opposite the AGUC cleavage sequence of the substrate. As shown in Examples 24 and 32, at least part of this AGAA sequence is invariant. In particular, when the A's at the 3' and 5' ends of the sequence (AGAA) were changed, the resulting catalysts were active (see FIG. 42A). However, when G or A (AGAA) in the center of the sequence was changed, the resulting catalysts were inactive (see FIGS. 21 and 42C).

The target RNA substrate of the "hairpin" catalytic complex shown in FIG. 1 has an AGUC cleavage loop which does not base pair to the catalytic RNA in two-dimensional space. As shown in Examples 13–15, "A" in the AGUC cleavage sequence can be changed to any other base without effecting the ability of the RNA catalyst to cleave the substrate. Example 25 shows that the GUC sequence is conserved. Thus, the only sequence requirement for the cleavage sequence of the substrate RNA is GUC.

Although there is no base pairing between the NGUC cleavage sequence and the AAGA sequence in the catalyst opposite from the cleavage sequence, the C in NGUC apparently interacts with the A in AAGA opposite to it. In particular, it has been found that the single mutation of C→A in the cleavage sequence NGUC (position 9 in the substrate sequence—see FIG. 42B) destroyed the ability of the RNA catalyst to cleave the substrate. When a second mutation was made in the ribozyme, changing the A at position 7 to a C, partial activity was restored (see Example 32), indicating some sort of interaction between C at position 9 in the substrate and the A at position 7 in the catalyst (see FIG. 42B).

The cleavage sequence has four flanking bases at its 5' end and six at its 3' end which base pair with the catalytic RNA. As described above, the bases in the flanking regions can be changed (with the possible exception of the G:C base pair in Helix 2 adjacent to NGUC) without affecting the ability of the catalytic RNA to cleave the substrate, as long as sufficient base pairing with the catalyst is maintained in the flanking regions. This would be expected to work on RNA substrate sequences of any length as long as these criteria are met. Indeed, lengthening the 3' region of the substrate that base pairs with the catalyst has been found to provide a more efficient catalytic reaction. See Examples 18, 21 and 32. However, a smaller 10 base substrate having three flanking bases at its 5' end and three flanking bases at its 3' end did not work as well as the 14-base substrate, as described in Example 9.

Using the "hairpin" model as a guide, RNA catalysts can be engineered that base pair with an RNA substrate and mediate a cleavage in the cleavage sequence. In particular, catalytic RNA can be engineered that will cleave any RNA substrate having a cleavage sequence, such as NGUC, and flanking regions with which the catalyst base pairs, so that the catalytic RNA and RNA substrate form a catalytic complex in a "hairpin" motif. To do this, the bases flanking the cleavage sequence must be identified and the catalytic RNA engineered so that it does not pair in two-dimensional space with the cleavage sequence but does pair with adequate numbers of flanking bases upstream and downstream of the cleavage sequence. When designing a synthetic catalyst based on the (−)sTRSV catalyst, the other principles set forth herein regarding conserved or preferred sequences should also be taken into account in designing the synthetic catalyst.

As shown in Examples 17–20 and 29, catalytic RNAs according to the invention can cleave specific viral and messenger RNA sequences. In Example 15, tobacco mosaic virus (TMV) RNA containing the 5' coding region of the replicase gene was targeted for specific cleavage by an appropriately engineered catalytic RNA. The target sequence contained changes in 8 of the 14 bases of the substrate RNA having a base sequence found within the catalytic complex of (−)sTRSV RNA and was cleaved by the engineered RNA catalyst under conditions near physiological. Catalytic RNAs were also designed and synthesized using the "hairpin" model as a guide which could cleave sequences from messenger RNA coding for chloramphenicol acetyl transferase (Example 18) and from HIV-1 viral RNA (Examples 19, 20 and 29). In particular, a conserved sequence in HIV-1 viral messenger RNAs has been identified, and a "hairpin" catalytic RNA designed which cleaves this sequence (see Example 29).

These examples demonstrate that the system can be used to specifically cleave an RNA sequence for which an appropriately engineered catalytic RNA base pairs at the designated flanking regions. Suitable target RNA substrates include viral, messenger, transfer, ribosomal, nuclear, organellar, other cellular RNA, or any other natural RNA having a cleavage sequence, as well as RNAs which have been engineered to contain an appropriate cleavage sequence.

Catalysts that fit the "hairpin" catalytic RNA model are useful in vivo in prokaryotes or eukaryptes of plant or animal origin for controlling viral infections or for regulating the expression of specific genes. In this case, a cleavage sequence such as NGUC in the virus or complementary to NGUC in the gene would need to be identified along with the flanking sequences immediately upstream and downstream of the cleavage sequence. Normally three to four bases on the 5' side of the cleavage sequence and enough bases in the order of 6 to 12 on the 3' side to provide adequate binding of the catalytic RNA and to provide reasonable certainty that the target RNA sequence is unique in the organism are required.

A catalytic RNA is then engineered which does not base pair with the cleavage sequence and which does base pair to the flanking regions on the 5' and 3' side of the cleavage sequence. A DNA template corresponding to this catalytic RNA is then synthesized using procedures that are well-known in the art. Such procedures include the phosphoramidite method (see, e.g., Beaucage and Caruthers, *Tetrahedron Letters*, 22, 1859 (1981); Matteucci and Caruthers, *Tetrahedron Letters*, 21, 719 (1980); and Matteucci and Caruthers, *J. Amer. Chem. Soc.*, 103, 3185 (1981)) and the phosphotriester approach (see, e.g., Ito et al., *Nucleic Acids Res.*, 10, 1755–69 (1982)).

The invention also includes an engineered DNA molecule and a vector comprising a DNA sequence coding for the desired synthetic RNA catalyst. The vector will have the DNA sequence coding for the desired catalytic RNA operatively linked to appropriate expression control sequences. Methods of effecting this operative linking, either before or after the DNA coding for the catalyst is inserted into the vector, are well known. Expression control sequences include promoters, activators, enhancers, operators, stop signals, cap signals, polyadenylation signals, and other signals involved with the control of transcription.

The vector must contain a promoter and a transcription termination signal, both operatively linked to the synthetic DNA sequence, i.e., the promoter is upstream of the synthetic DNA sequence and the termination signal is downstream from it. The promoter may be any DNA sequence that shows transcriptional activity in the host cell and may be derived from genes encoding homologous or heterologous proteins and either extracellular or intracellular proteins, such as amylase, glycoamylases, proteases, lipases, cellulases, and glycolytic enzymes. Also, a promoter recognized by T7 RNA polymerase may be used if the host is also engineered to contain the gene coding for T7 RNA polymerase.

The promoter may contain upstream or downstream activator and enhancer sequences. An operator sequence may also be included downstream of the promoter, if desired.

Expression control sequences suitable for use in the invention are well known. They include those of the *E. coli* lac system, the *E. coli* trp system, the TAC system and the TRC system; the major operator and promoter regions of bacteriophage lambda; the control region of filamentous single-stranded DNA phages; the expression control sequences of other bacteria; promoters derived from genes coding for *Saccharomyces cerevisiae* TPI, ADH, PGK and alpha-factor; promoters derived from genes coding for the *Aspergillus oryzae* TAKA amylase and *A. niger* glycoamylase, neutral alpha-amylase and acid stable alpha-amylase; promoters derived from genes coding for *Rhizomucor miehei* aspartic proteinase and lipase; mouse mammary tumor promoter; SV40 promoter; the actin promoter; and other sequences known to control the expression of genes of prokaryotic cells, eukaryotic cells, their viruses, or combinations thereof.

The vector must also contain one or more replication systems which allow it to replicate in the host cells. In particular, when the host is a yeast, the vector should contain the yeast 2 u replication genes REP1–3 and origin of replication.

The vector should further include one or more restriction enzyme sites for inserting the DNA template sequences into the vector, and preferably contains a DNA sequence coding for a selectable or identifiable phenotypic trait which is manifested when the vector is present in the host cell ("a selection marker").

Suitable vectors for use in the invention are well known. They include retroviral vectors, vaccinia vectors, pUC (such as pUC8 and pUC4K), pBR (such as pBR322 and pBR328), pTZ (such as pTZ18R), pUR (such as pUR288), phage lambda, YEp (such as YEp24) plasmids, and derivatives of these vectors.

The resulting vector having the engineered DNA sequence that codes for the RNA catalyst is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity to it of the catalytic RNA encoded for by the engineered DNA sequence, rate of transformation, expression characteristics, bio-safety and costs. A balance of these factors must be struck with the understanding that not all hosts may be equally effective for the expression of a particular catalytic RNA.

Within these general guidelines, useful hosts include bacteria (such as *E. coli* sp.), yeast (such as Saccharomyces sp.) and other fungi, insects, plants, animals (including human), or other hosts known in the art.

As an example of the general genetic engineering techniques that are possible, mammalian vectors can be used to deliver DNA coding for the catalytic RNAs of the invention to animal cells. These vectors should have a suitable DNA replication signal, such as from SV40, a promoter which may or may not be inducible, such as the mouse mammary tumor promoter (which is induced by dexamethasone) or the noninducible SV40 promoter. A multiple cloning site is located after the promoter, and the DNA coding for the engineered catalytic RNA is inserted into this multiple cloning site using standard techniques. If necessary a suitable terminator is inserted. The resulting vector is then put into cells using standard techniques such as direct injection into the nucleus, electroporation, or other well-known transformation techniques. Once the vector is in the cell, the catalytic RNA is expressed directly when noninducible promoters are used, or after addition of the inducer when inducible promoters are used.

Similarly, plant vectors, such as the Ti plasmid or micro-Ti plasmids, can be used to deliver DNA coding for a desired catalytic RNA to plant cells. The Ti plasmids and micro-Ti plasmids may be used as such to transform plant protoplasts using known techniques or may be inserted into *Agrobacterium tumefaciens* which is then used to transform plant tissue. Once the plasmid is in the cell, the catalytic RNA will be expressed.

Once transformed, a host cell can express (transcribe) the synthetic RNA catalyst. When the DNA coding for the catalyst is transcribed, it produces catalytic RNA which will attack and cleave the target RNA sequence or sequences for which it has been designed, inactivating the RNA. If the RNA is necessary for the life cycle of a virus, the virus will be eliminated and if the RNA is the product of a specific gene, the expression of that gene will thus be regulated. The catalytic RNA can be designed to work in prokaryotes and within the nucleus (without poly(A) tail) or in the cytoplasm of a eukaryotic cell (with polyadenylation signals in place) for plants and animals.

Another potential method of using the catalytic RNAs of the invention is to prepare stable synthetic derivatives of RNA catalysts designed to bind and cleave a specific target RNA and to deliver the modified catalysts directly to the cell or organism of choice. For example, standard methods are available for making phoshporothioate derivatives of DNA which have been shown to be very stable in vivo and to be able to bind to a specific DNA or RNA target in vivo (antisense method). A modification of these procedures can be used to prepare a catalytically active derivative of RNA catalysts prepared according to the invention. This would entail determining which ribonucleotide regions can be altered and then altering them with deoxy, phophorothio, or other modifications which confer stability but do not destroy catalytic activity. This chemically modified catalytic RNA (which may or may not have any remaining RNA bonds) can then be injected or otherwise delivered to an organism to control viruses or gene expression. For instance, one of the catalytic RNAs whose preparation is described in Examples 19–20 having specificity for sequences found within the RNA of the HIV-1 virus that causes AIDS could be chemically modified as described, encapsulated in a liposome coated with monoclonal antibody directed to the CD4 receptors found on cells susceptible to HIV-1, and injected into a host animal.

The "hairpin" catalytic RNA model of the present invention may also be of possible interest to molecular biologists in exploring the genetic blueprints of plants and animals. This would be done by sending randomly constructed DNA reverse transcripts of catalytic RNA into the DNA of the organism and waiting to see which gene or genes were inactivated. Other techniques could be applied to determine where those genes resided on the organism's chromosomes, thereby greatly accelerating gene mapping.

Finally, a synthetic autocatalytic RNA catalyst has been developed. The synthesis of one such catalyst based on the (−)sTRSV RNA catalytic and substrate sequences is described in Example 23. When the DNA coding for this catalyst was transcribed in vitro, auto-catalytic cleavage was observed. Further, in Example 26, DNA coding for this catalyst was linked to the gene coding for chloramphenicol acetyl transferase (CAT) in vector pHC-CAT. This vector was then used to transform *Escherichia coli*. Northern blot analysis of the RNA produced by the *E. coli* hosts indicated that auto-catalytic cleavage occurred in vivo under standard *E. coli* growth conditions. Similar results were obtained when mamalian and plant cells were transformed with a vector coding for this autocatalytic RNA linked to either the gene coding for CAT (mammalian cells) or to DNA coding for cauliflower mosaic virus (plants) (see Examples 27 and 28). The autocatalytic RNA catalyst has also been used to properly terminate other engineered RNA catalysts after they were transcribed. In this manner, the engineered RNA catalysts were liberated from the RNA transcript and acted in trans in vivo (see Example 31).

EXAMPLES

The following examples further illustrate the invention.

Example 1

The (−) sense sequence of satellite RNA from the budblight strain of tobacco ringspot virus as shown in FIG. 2 was folded using the Wisconsin RNA folding program to identify the location of a possible catalytic complex accounting for its ability to self cleave (University of Wisconsin Genetics Computer Group, Program FOLD 5/6/86) (Zucker, M. and Stiegler, P. (1981) *Nucleic Acids Res.*, 9: 133–148; Devereux, J., Haeberli, P. and Smithies, O. (1984) *Nucleic Acids Res.*, 12: 387–395). Base numbers correspond to (+)sTRSV RNA (Buzayan, J. M., Gerlach, W. L., Bruening, G. B., Keese, P. and Gould, A. R. (1986) *Virology*, 151: 186–199). With this numbering scheme the 5'–3' direction of the molecule is with decreasing base number.

The minimum catalytic complex, or active site of the molecule, is identified in FIG. 2. The folding identified regions of expected base pairing which are in classical double-helical or stem regions. The folding also identified expected non-base pairing loops at or near the site of cleavage. This model does not preclude higher order interactions occurring between non-adjacent portions of the catalytic center.

Example 2

A 50 nucleotide sequence between bases 175 and 224 was picked and a 14 nucleotide sequence between bases 40 and 53 was picked from the catalytic complex identified in Example 1. A catalytic RNA (R51) with the 50 base sequence shown in FIG. 1 plus one additional vector base (G at the 5' end) and a substrate RNA (S17) with the 14 base sequence shown in FIG. 1 plus three vector bases (GCG at the 5' end) were transcribed using T7 RNA polymerase from synthetic DNA templates double stranded at the promoter site (Milligan, J. F., Groebe, D. R., Witherell, G. W. and Uhlenbeck, O. C. (1987) *Nuc. Acids Res.*, 15: 8783–8798). The synthetic DNA templates were made using phosphoramidite chemistry on an Applied Biosystems 381A DNA synthesizer. The template DNAs were: catalytic RNA R51: 3'-ATTATGCTGAGTGATATCTTTGTCTCTTCAGTTG-GTCTCTTTGTGTGCAACACCATATAATGGACCAT-5' (SEQ ID NO 8) and substrate RNA S17: 3'-ATTAT-GCTGAGTGATATCGCACTGTCAGGACAAA-5' (SEQ ID NO 9).

Before transcription, a 18 mer or 16 mer DNA complement to the promoter for T7 RNA polymerase on the noncoding strand was hybridized by heating an equimolar amount of template DNA with promoter complement to 65° C. for 3 min. then placing in ice. A typical transcription reaction used 8 ng/ul DNA template, 0.5 mM each NTP, 2 mM spermidine, 40 mM Tris pH 7.5, 4% polyethylene glycol 6,000, 6 mM MgCl$_2$, 4 mM NaCl, 10 mM dithiothreitol, 0.01% Triton X-100, 2.4 units/ul RNasin, 1.8 uCi/ul P$^{32}$ CTP and 3 units/ul T7 RNA polymerase (US Biochemical) and was run at 37° C. for 90 min.

All in vitro transcribed RNAs were isolated on 7M urea, 15–20% acrylamide gels, bands cut out and isolated. All RNAs were sequenced using standard methods (Donis-Keller, H., Maxam, A. M. and Gilbert, W. (1980) *Nucleic Acids Res.*, 4: 2527–2538); a method which also gave the 5' terminal base. Terminal bases at the 3' end were determined by ligation of the RNA to 5' P$^{32}$ pCp using T4 RNA ligase (BRL methods manual), nuclease T2 digestion, and separation of labelled bases by PEI thin layer chromatography in 0.3M LiCl with appropriate standards. All RNA sequences corresponded to that expected from the DNA template.

Example 3

The catalytic RNA R51 was added to the substrate RNA S17 at a ratio of 1:30 and the time course of substrate RNA cleavage was studied. The reaction was carried out at 37° C. in 12 mM $MgCl_2$, 40 mM Tris pH 7.5 and 2 mM spermidine over a time period of 150 min and is summarized as follows:

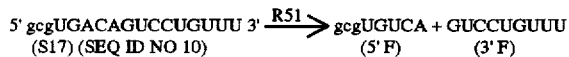

5' gcgUGACAGUCCUGUUU 3' →R51→ gcgUGUCA + GUCCUGUUU
(S17) (SEQ ID NO 10)      (5'F)    (3'F)

The reaction products were separated on polyacrylamide/urea gels by electrophoresis and bands cut out and counted in a liquid scintillation counter. The results are shown in FIGS. 3A–3B. The time periods analyzed were: lane 1, 30 sec; lane 2, 5 min; lane 3, 15 min; lane 4, 30 min; lane 5, 60 min; lane 6, 90 min and lane 7, 150 min. Beginning concentrations were as follows: R51=0.0032 uM and S17=0.09 uM.

As shown in FIGS. 3A–3B, the cleavage proceeds to virtual completion during the course of the reaction with only 2% of the substrate remaining after 150 minutes. This shows that, since there was originally 30 times as much substrate RNA as catalytic RNA, the RNA catalyst R51 of necessity interacts with multiple substrate molecules during the course of the reaction. In addition, the amount of catalyst remained the same and was unaltered, indicating that R51 is truly a catalytic entity.

Example 4

After the RNA catalyst had been shown to be effective in cleaving the RNA substrate as described in Example 3, minimum energy folding of the 50 base sequence shown in FIG. 1, complexed with the 14 base sequence was done using the computer methods described in Example 1. The folded complex forms a "hairpin" model or motif as shown in FIG. 1 with the substrate RNA sequence and the catalytic RNA sequence identified. The arrow is at the site of cleavage.

Example 5

Various concentrations of substrate S17 were used at constant concentration of catalyst R51 and initial velocities of each reaction determined. The reaction was carried out at 37° C. in 12 mM $MgCl_2$, 40 mM Tris pH 7.5 and 2 mM spermidine. Concentrations were as follows: R51=0.0004 uM and S17=0.125 uM (lane 1), 0.0624 uM (lane 2), 0.0417 uM (lane 3), 0.031 uM (lane 4), 0.021 uM (lane 5), 0.0156 uM (lane 6), 0.0078 uM (lane 7) and 0.0039 uM (lane 8). Each reaction was analyzed on polyacrylamide gels as described in Example 3 with the results shown in FIGS. 4A–4B. An Eadie Hofstee plot of catalytic RNA R51 cleavage of substrate RNA S17 is shown in FIGS. 4A–4B. The reaction proceeded according to the predictions of the Michaelis-Menten equation indicating that it was a truly enzymatic reaction in that as the concentration of the substrate goes down, the velocity of the reaction goes down. From the velocity of the reaction plotted as a function of substrate concentration, the Km calculated from the graph was 0.03 uM and the kcat (turnover number) was 2.1/min. This Km is 20 times smaller than the "hammerhead" catalysts (see Uhlenbeck, O. C. (1987) Nature, 328: 596600) indicating that lower concentrations of substrate can be removed. The kcat is 6 times larger than that of catalysts fitting the "hammerhead" model at 37° C. (see Uhlenbeck, O. C. (1987) Nature, 328: 596–600), meaning that the reaction is 6 times faster.

Example 6

The temperature dependence of the rate of cleavage of substrate RNA S17 by catalytic RNA R51 was tested over a temperature range and the reaction products analyzed on polyacrylamide gels as described in Example 3 with the results shown in FIGS. 5A–5B. The reaction was carried out in 12 mM $MgCl_2$, 40 mM Tris pH 7.5 and 2 mM spermidine at 45° C. (lane 6), 41° C. (lane 5), 37° C. (lane 4), 33° C. (lane 3), 27° C. (lane 2) and 20° C. (lane 1). The concentrations used were: R51=0.0016 uM and S17=0.04 uM. R51 was unlabeled. The velocities shown in the graph in FIGS. 5A–5B were calculated by the use of time points of 8 and 16 minutes. The separation patterns on the gel shown in FIGS. 5A–5B are for the 16-minute time point.

The reaction showed a temperature dependence similar to that which would be expected of a reaction involving base paired RNA molecules. The Arrhenius plot of the data shown in FIGS. 5A–5B give a temperature optimum of 37° C. for the reaction. Higher temperatures reduce the reaction rate with a very rapid rate reduction above 41° C. consistent with a melting out of the catalytic RNA structure. At 50° C. no reaction was detectable. The reaction rate at temperatures below 37° C. showed a linear reciprocal temperature dependence consistent with a classical lowering of the energy of activation for the reaction. The slope of the line in the Arrhenius plot gave an energy of activation of 19 Kcal/mole which is close to that found for catalysts fitting the "hammerhead" cleavage mechanism (13.1 Kcal/mole) (Uhlenbeck, O. C. (1987) Nature, 328: 596–600).

Example 7

The rate of cleavage of a constant concentration of substrate RNA S17 at varying concentrations of catalytic RNA R51 was tested and the reaction products analyzed on polyacrylamide gels as described in Example 3 with the results shown in FIGS. 6A–6B. The reaction was carried out at 37° C. in 12 mM $MgCl_2$, 40 mM Tris pH 7.5 and 2 mM spermidine for 40 min (lane 1 and 2), 20 min (lane 3), 10 min (lane 4) and 5 min (lane 5). The concentration of substrate was 0.175 uM. The results are plotted in FIGS. 6A–6B and show that at saturating concentrations of substrate the reaction rate is linear with increasing RNA catalyst concentrations as one would expect for a true catalytic reaction.

Example 8

The effect of $Mg^{++}$ concentration and pH on the rate of cleavage of RNA substrate S17 by RNA catalyst R51 was determined as shown in the following table:

| $MgCl_2$ (mM) | $t_{1/2}$ (min) |
| --- | --- |
| 0 | no detectable product |
| 4 | 136 |
| 6 | 111 |
| 8 | 115 |
| 10 | 88 |
| 12 | 81 |
| 15 | 74 |
| 20 | 62 |

-continued

| pH | $t_{1/2}$ (min) |
|---|---|
| 5.5 | 330 |
| 6.0 | 120 |
| 6.5 | 67 |
| 7.0 | 48 |
| 7.5 | 42 |
| 8.0 | 38 |

In the $Mg^{++}$ studies, the substrate S17 concentration was 0.14 uM and RNA catalyst R51 concentration was 0.0015 uM. The reactions were at 37° C. in 40 mM Tris pH 7.5. In the pH studies, the substrate S17 concentration was 0.062 uM and RNA catalyst R51 concentration was 0.0014 uM. The reactions were at 37° C. in 40 mM Tris for pH 7.0, 7.5, 8.0 and in 40 mM Pipes for pH 5.5, 6.0 and 6.5.

The dependence of the reaction rate on $Mg^{++}$ and pH are virtually identical with those of catalysts fitting the "hammerhead" model. The reaction rate increases with increasing pH as one would expect for a base catalyzed reaction but the effect is masked by the catalytic activity of the RNA. Hence a 100 fold increase in [OH] between pH 6.0 and 8.0 resulted in only a 3 fold increase in the reaction rate.

Example 9

A 10 base substrate (S10) was prepared by the methodology of Example 2. When the substrate was mixed with catalytic RNA R51, the reaction is summarized as follows:

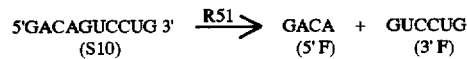

The results of rate studies with substrate S10 comparable to those described with S17 in Example 5 showed a Km=0.06 uM and a kcat=0.8/min. These results are shown in FIG. 7 and indicate that smaller substrates can be used, but not as efficiently.

Example 10

The 3' terminal base of the catalyst shown in the "hairpin" model of the (−)sTRSV catalytic complex in FIG. 1 is at position 175. Two catalytic RNAs were prepared with exactly the same sequence as R51, except that one of them did not contain the 3' terminal "A" base (position 175) and the other one did not contain the 3' terminal "UA" sequence (positions 176 and 175). Synthesis of these catalytic RNAs, designated R50 and R49, respectively, was carried out as described in Example 2. R50 or R49 catalytic RNA was mixed with substrate RNA S17 under standard conditions of reaction and the products analyzed as described in Example 3. The results are given in FIGS. 8A–8B and show a 75% reduction in activity with either R50 or R49 as compared to the activity of catalytic RNA R51 having the 3' terminal "A" at position 175 and the 3' terminal "AU" at positions 175 and 176.

Example 11

An RNA with the same sequence as catalytic RNA R51 was prepared, except that bases 195–203 were omitted such that base 194 was in effect ligated to base 204. This RNA molecule was prepared as described in Example 2 from an appropriate DNA template containing the complementary sequence. When this RNA was mixed with substrate RNA S17 as described in Example 3, no reaction occurred. These results show that major elements of the "hairpin" structure are required for RNA catalysis to occur and that removal of 9 bases (see FIG. 9) in the middle inactivates the catalytic RNA.

Example 12

An RNA with the same sequence as R51, except that the bases AAA at positions 203, 202 and 201 were changed to CGU, respectively, was prepared as described in Example 2 using an appropriate DNA primer. When this potential RNA catalyst was mixed with substrate RNA S17 as described in Example 3, no reaction occurred. This shows that the integrity of one or all of these bases (see FIG. 10) is required for catalytic activity.

Example 13

A substrate RNA with the base at position 49 in FIG. 1 changed from an "A" to a "G" was prepared as described in Example 2. When this substrate was reacted with the RNA catalyst R51, no difference in rate of reaction was seen between this substrate and the substrate containing the "A" at position 49 (see FIGS. 11A–11B). This shows that alterations can occur in the "A" base in the substrate RNA AGUC loop without affecting the ability of the catalytic RNA to cleave the substrate.

Example 14

Another substrate RNA identical to S17 but having "A" replaced by "U" in the AGUC loop was prepared as described in Example 2 (designated "S17(A→U)"). This substrate RNA, at a concentration of 0.12 uM, was reacted with the catalytic RNA R51, at a concentration of 0.0065 uM, under standard conditions as described in Example 3 for 60 minutes. The results are shown in FIGS. 11C–11D where Lane 1 contains the products of the reaction of substrate RNA S17(A→U) with R51 catalytic RNA. No difference in the rate of reaction was seen between S17(A→U) substrate RNA and substrate S17 containing the "A" base at position 49.

Example 15

Another substrate RNA identical to S17 but having "A" replaced by "C" in the AGUC loop was prepared as described in Example 2 (designated "S17(A→C)"). This substrate RNA, at a concentration of 0.08 uM, was reacted with the catalytic RNA R51, at a concentration of 0.0065 uM, under standard conditions as described in Example 3 for 60 minutes. The results are shown in FIGS. 11E–11F where Lane 1 contains the products of the reaction of S17(A→C) substrate RNA with R51 catalytic RNA. Again, no difference was seen in the rate of reaction using S17(A→C) as compared to S17 containing the "A" base at position 49. The combined results of Examples 13–15 show that the base at position 49 in the cleavage sequence of the substrate may be any base.

Example 16

Base changes in the stem regions at the site of binding of the substrate RNA to the catalytic RNA in the "hairpin" configuration can be made as long as the base pairing is maintained. The "C" base at position 50 of the substrate was changed to a "G" using the methods in Example 2. When this substrate RNA was reacted with the catalytic RNA R51, no cleavage of this substrate occurred. However, when a new catalytic RNA, containing a "C" at position 214, rather than the "G" found in R51, was synthesized according to the methods in Example 2 and added to this substrate, full cleavage was seen. The effect of the base change from "C" to "G" in the substrate was to eliminate the base pairing at this position predicted by the "hairpin" model since now a "G" would be across from a "G". However, when a "G" to "C" base change was made in the catalytic RNA, the base pairing was restored, but in a reverse manner, and the integrity of the helices in the stem regions where the substrate RNA binds to the catalytic RNA was thus conserved restoring catalytic activity (see FIGS. 12A–12B).

Example 17

An RNA sequence found within the sequence of tobacco mosaic virus was synthesized using the methods described in Example 2. This synthesized target RNA had the sequence 5' gAAACAGUCCCCAAC 3' (SEQ ID NO 11). A catalytic RNA was synthesized with the sequence 5'-GUUGG-GAGAAGUUUACCAGAGAAACACACGUUGUGGUA-UAUUACCUGGUA-3' (SEQ ID NO 12) selected so that base pairing between the substrate and the catalytic RNA is maintained in the "hairpin" configuration (see FIGS. 13A–13B). When these two RNAs were mixed under standard catalytic conditions as described in Example 3, the target was cleaved demonstrating that a sequence found within a native viral RNA can be cleaved.

Example 18

Three RNA sequences found within the sequence of the messenger PNA for the enzyme chloramphenicol acetyl transferase (CAT) were synthesized using the methods described in Example 2. The synthesized substrate RNAs had the sequences (A) gUUUCAGUCAGUUGC; (B) gUUUCAGUCAGUUGCUC; and (C) gggUUUCAGU-CAGUUGCUCAA (SEQ ID NO) (see FIGS. 14A–14F).

Note that the latter two sequences are extensions of the first sequence and that additional bases have been added to the 3' end in the region that the "hairpin" model predicts will base pair with the catalytic RNA to form Helix 1 (see FIG. 18). Also, substrate (C) had two additional G vector bases as compared to substrates (A) and (B). The site of cleavage after the A in the AGUC cleavage sequence (see the arrow in FIGS. 14A–14F) of the substrates corresponds to position 320 of the CAT gene using the number system found in the Tn9 sequence (Alton and Vapnak, Nature, 282, 864 (1979)). In FIGS. 14A–14F, the open boxed bases are those which are different from those in the native (−)sTRSV substrate RNA sequence shown in FIG. 1.

Catalytic RNAs corresponding to substrate RNAs (A), (B) and (C) were synthesized according to the methods described in Example 2. Their sequences were designed so that they would base pair with the substrate RNAs in both the 3' and 5' regions flanking the AGUC cleavage sequence. In addition, the catalytic RNAs designed to react with substrate RNAs (A) and (B) each contained the vector sequence GA at their 5' terminus, and the catalytic RNA designed to react with substrate RNA (C) contained the vector sequence GGG at its 5' terminus. Otherwise, the catalytic RNAs had the same sequence as the (−)sTRSV catalytic RNA sequence shown in FIG. 1.

The various substrate and catalytic RNAs were reacted and the reaction products analyzed as described in Example 3. All reaction conditions were as described in Example 3, except for the following. For substrates (A) and (B), reaction conditions were: substrate RNA concentration =0.05 uM; catalytic RNA concentration =0.005 uM; reaction run at 16° C.; and reaction time of 20 minutes. For substrate (C), the reaction conditions were the same as for (A) and (B), except that the reaction time was 40 minutes and temperatures were 20° C., 25° C., 30° C. and 37° C.

Cleavage of all of the substrate RNAs occurred when they were mixed with the corresponding catalytic RNAs as is shown in FIGS. 14A–14F, demonstrating that catalytic RNAs according to the invention can be synthesized which cleave specific RNA sequences found within a messenger RNA. In addition, this example demonstrates that cleavage of substrate RNA can be obtained even though the length of the region at the 3' end of the substrate which base pairs with the catalyst (i.e., the portion that forms Helix 1 with the substrate according to the "hairpin" model) is varied. Indeed, when the length of this region was extended to 10 bases in substrate (C), the reaction could then proceed at 37° C., whereas for substrates (A) and (B) having shorter sequences in this region, the reaction would proceed only at 16° C.

Example 19

An RNA substrate corresponding to part of the sequence of HIV-1, the virus which causes AIDS, was synthesized as described in Example 2. The sequence of this substrate RNA is shown in FIG. 15A. The arrow in FIG. 15A shows the cleavage site which corresponds to position 804 in the sequence of HIV-1 strain SF2CG (Sanchez-Pescador et al., Science, 227, 484 (1985). The sequence shown is found in the region of the viral RNA which specifies the gag protein. The RNA substrate also had a GCG 5' vector sequence. The open boxed bases in FIG. 15A are those which are different than those of the native (−)sTRSV substrate sequence shown in FIG. 1.

A catalytic RNA was synthesized according to the methods of Example 2. Its sequence was designed so that it would base pair with the substrate RNA in both the 3' and 5' regions flanking the CGUC cleavage sequence. In addition, the catalytic RNA contained the vector sequence GGG at its 5' terminus. Otherwise, the catalytic RNA had the same sequence as the (−)sTRSV catalytic RNA sequence shown in FIG. 1.

The catalytic RNA and the substrate RNA were reacted and the reaction products were analyzed as described in Example 3. The reaction conditions were as set forth in Example 3, except that the following temperatures were used: 20° C., 25° C., 30° C. and 37° C. Also, the reaction was run for 60 minutes, except for 37° C. which was run for 15 minutes, and the substrate RNA concentration was 50 nM, and the catalytic RNA concentration was 5 nM.

The catalytic RNA cleaved the substrate at the expected position between the "C" and "G" in the CGUC cleavage sequence found in the loop between the two flanking stem regions. Thus, a specific sequence found in the HIV-1 viral RNA that codes for the gag protein can be cleaved with a catalytic RNA according to the invention. The reaction occurred with an RNA substrate having a 16-base target sequence which was longer than S17 in the region at the 3' end which base pairs with the catalyst (i.e., the portion that forms Helix 1 with the catalytic RNA according to the "hairpin" model). Also, the reaction occurred at physiological temperature of 37° C.

Example 20

A substrate RNA having a sequence found in the beginning of the coding region for the regulatory protein tat of HIV-1 virus was synthesized as described in Example 2. The substrate sequence is shown in FIG. 16A. In addition to the HIV-derived sequence, the substrate RNA had a GCG 5' vector sequence. The open boxes are around bases which are different than those of the native (−)sTRSV substrate sequence shown in FIG. 1.

A catalytic RNA having a sequence so that it would base pair with the substrate RNA in the two regions flanking the UGUC loop (i.e., the regions that forms Helices 1 and 2 with the catalytic RNA according to the "hairpin" model) was also synthesized as described in Example 2. Otherwise, the catalytic RNAs had the same sequence as the (−)sTRSV catalytic RNA sequence shown in FIG. 1, except that it had an additional 5' G vector base.

The substrate RNA and catalytic RNA were reacted and the reaction products were analyzed as described in Example 3. Reaction conditions were: 37° C.; reaction times of zero and 15 minutes; the concentration of substrate RNA was 100 nM; and the concentration of catalytic RNA was 20 nM.

Cleavage occurred as expected between the "U" and the "G" in the UGUC cleavage sequence located between the two stem regions of the substrate. The cleavage site is indicated by the arrow in FIG. 16A. This is position 5366 in the sequence of HIV clone h9c (Muesing et al., *Nature*, 313, 450 (1985)). These results again confirm that a catalytic RNA designed according to the "hairpin" model can cleave a specific target sequence located in a naturally occurring RNA, in this case a key regulatory region (tat) of the HIV-1 virus which causes AIDS.

Example 21

Using the methods described in Example 2, a substrate RNA having four non-native bases (UUUU) added to the 3' end of the sequence of the native (−)sTRSV substrate shown in FIG. 1 and a corresponding catalytic RNA designed to base-pair with the substrate RNA in the 3' and 5' regions of the substrate flanking the cleavage sequence (ie., the portions that form Helices 1 and 2 with the catalyst according to the "hairpin" model) were made. Thus, the substrate RNA contained a total of 18 bases, including a four-base extension of the 3' region that base pairs with the catalyst. The substrate RNA also had an additional GCG vector sequence at the 5' end. The catalyst had the same sequence as the (−)sTRSV catalytic RNA sequence shown in FIG. 1, except that it had four additional AAAA bases at the 5' end designed to base pair with the added UUUU bases of the substrate and had an additional "G" vector base at the 5' terminus beyond the 18 base recognition site.

The substrate and catalytic RNAs were reacted at standard conditions and the reaction products were analyzed as described in Examples 3 and 5. Catalytic RNA concentration was 0.00033 uM, and substrate RNA concentration was 0.1 uM (Lane 1), 0.05 uM (Lane 2), 0.033 uM (Lane 3), 0.025 uM (Lane 4), 0.016 uM (Lane 5), 0.012 uM (Lane 6), 0.006 uM (Lane 7), and 0.003 uM (Lane 8). The results are shown in FIGS. 17A–17B. Cleavage rates at each concentration of substrate were determined by cutting out the bands, counting radioactivity in a liquid scintillation counter and plotting the data using Michaelis-Menton procedures to calculate Km and kcat (see Example 5).

The data show that an extension of the length of the region of base pairing between the substrate and catalyst (i.e., those regions of the catalyst and substrate that form Helix 1 according to the "hairpin" model) can improve the catalytic properties of the reaction. Cleavage of the 18-base RNA substrate occurred at the expected site, but at an increased rate as compared to the cleavage of S17 by R51. The kcat or turnover number of the reaction was 7/minute. This means that each molecule of catalytic RNA cleaved 7 molecules of substrate RNA per minute during the reaction. The kcat for S17 cleavage by R51 was 2.1/minute. The Km of the reaction was the same as for S17 cleavage by R51 (30 nM). This shows that by optimizing the length of the region of the catalyst that base pairs to the substrate in the 3' region flanking the cleavage sequence (i.e., by optimizing the length of Helix 1 predicted by the "hairpin" model), the catalytic properties of the native reaction can be improved.

Example 22

A series of catalytic RNAs were prepared using the methods described in Example 2 having certain base substitutions as compared to the native (−)sTRSV catalytic RNA sequence shown in FIG. 1. The substitutions, which are illustrated in FIG. 19A, were the following: (1) At nucleotide 35, G was replaced by C (G35→C) (count bases from the 5' end of the catalytic RNA sequence shown); (2) A double mutant, having the G at position 35 replaced by C and the C at position 27 replaced by G (G35→C; C27→G); (3) At nucleotide 47, G was replaced by C (G47→C); and (4) A double mutant having the G at position 47 replaced by C and the C at position 17 replaced by G (G47→C; C17→G). All catalytic RNAs had an additional "G" vector base at their 5' end.

The various catalytic RNAs were reacted with substrate S17 and the reaction products were analyzed as described in Example 3. The results are shown in FIG. 19B where Lanes 1, 3, 5, 7, 9 and 11 are at zero time, and Lanes 2, 4, 6, 8, 10 and 12 are 15 minutes incubation under standard cleavage conditions (see Example 3). The concentration of catalytic RNA was 0.0065 uM, and the concentration of substrate RNA was 0.17 uM. The temperature was 37° C. The control, lanes 1, 2, 7 and 8, was cleavage of the native substrate RNA S17 by catalytic RNA R51 which has the native (−)sTRSV sequence (see FIG. 1).

As shown in FIGS. 19A–19B, the catalytic RNA G35→C had no catalytic activity (see Lanes 3 and 4 of FIG. 19B, where this catalytic RNA is designated "mismatch" since the base substitution at position at position 35 results in a loss of base pairing). The double mutant catalytic RNA G35→C; C27→G showed restored catalytic activity (see Lanes 5 and 6 of FIG. 19B where this catalytic RNA is designated "substitute b.p." since the net effect of the two base substitutions is to create a base pair, but a base pair different than the one found in the native (−)sTRSV catalytic RNA). The catalytic RNA G47→C was also inactive (see Lanes 9 and 10 of FIG. 19B), while the double mutant, with the second mutation C17→G, showed restored activity (see Lanes 11 and 12 of FIG. 19B).

The results of these mutagenesis studies provide confirmation for the existence of Helices 3 and 4 (see FIGS. 19A–19B) of the "hairpin" catalytic RNA model proposed herein. The results show that when mutagenesis was carried out which caused a base pair mismatch in the region of proposed base pairing, the catalytic RNA was inactive. However, when a second mutation was carried out so that the base pair was restored, catalytic activity was restored, even though the new base pair was different than the original base pair. Such results are considered evidence for the existence of a helix (Fox and Woese, *Nature*, 256, 505 (1975). These results also show that a variety of catalytic RNAs having sequences different from the native (−)sTRSV sequence are catalytically active if they are designed so that they follow certain rules derived from the "hairpin" model, such as maintenance of substantial base pairing in regions of predicted helices.

Example 23

A synthetic "hairpin" autocatalytic cassette was prepared. The RNA sequence of the cassette is shown in FIG. 20A. Several bases have been added at the 5' end of the catalyst as compared to the native (−)sTRSV sequence shown in FIG. 1. The effect is to close the open end of the "hairpin" and to provide a substrate sequence (i.e., a cleavage sequence and upstream and downstream flanking regions) which can base pair with the substrate binding portion of the catalyst.

The cassette was prepared by making an appropriate synthetic DNA template that would yield an RNA with the sequence shown in FIG. 20A and using the DNA template to transcribe RNA as described in Example 2, with the following differences. After synthesizing the DNA template, it was inserted into the vector pTZ18R (US Biochemical) into which a new multiple cloning site had been inserted. The new multiple cloning site was a construct containing sites, in 5'→3' order, for cleavage by the following enzymes: BamHI, XhoI, ApaI, SacII, NaeI, StuI, KpnI, MluI. The new multiple cloning site was inserted into vector pTZ18R by cleaving the vector with BamHI and SalI and then ligating the multiple cloning site to the vector using T4 ligase. Located 5' to the inserted multiple cloning site is the T7 RNA polymerase promoter. The vector containing the multiple cloning site was digested with MluI and SalI, and the DNA template coding for the autocatalytic cassette was ligated into the vector using T4 ligase. The resultant vector was then linearized with HindIII, and transcription carried out as described in Example 2. All restriction enzymes and the T4 ligase were obtained from IBI and used according to manufacturer's instructions.

After being transcribed, the cassette spontaneously underwent an intramolecular autocatalytic cleavage at the expected site to give the appropriate 3'F and 5'F products (see FIGS. 20A–20B). Note that the effect of this is to autocatalytically terminate a transcript. For example, the 5'F is in itself a transcript which has been terminated at its 3' end by the autocatalytic reaction. Further note that this termination only leaves five essential bases at the 3' end of this 5'F. These are UGACA which are boxed in FIG. 20A. Thus, it is possible to very efficiently terminate transcription with this autocatalytic cassette and leave only a very short 3' end to the transcript (ie., the 5' fragment of the auto-catalytic cleavage).

Example 24

A catalytic RNA was prepared as described in Example 2. Its sequence was identical to that of R51, except that the base at position 217 in the AGAA loop was changed from a G to a C. The AGAA loop of the catalyst is opposite the cleavage sequence of the substrate when the substrate and catalyst are complexed (see FIG. 1)

Another catalytic RNA was prepared as described in Example 2. Its sequence was also identical to R51, except that the base at position 216 was changed from A to U.

These catalysts were reacted with the RNA substrate S17 under standard conditions as described in Example 3 at 37° C. for 0 and 15 minutes. The control was the reaction of substrate S17 with catalyst R51. The concentration of the three catalytic RNAs was 0.007 uM, and the concentration of substrate RNA was 0.7 uM.

The reaction products were analyzed as described in Example 3, and the results are shown in FIGS. 21A–21B, where the first lane in each gel is zero time and the second lane is 15 minutes of reaction. As shown in FIGS. 21A–21B, changes in either one of these two bases (G217→C and A216→U) in the loop opposite the cleavage sequence of the substrate destroyed the activity of the catalyst. These results indicate that these two bases are likely invariant in the native (−)sTRSV catalytic sequence.

A third catalytic RNA was prepared as described in Example 2. Its sequence was identical to R51, except that the base at position 218 was changed from A to C. This catalyst was also reacted with substrate S17 as described above. Cleavage of the substrate with this catalyst was observed, but only at about 47% of the level achieved with R51 (data not shown).

Example 25

Substrate RNAs identical to S17, but with one of the bases at positions 46, 47 or 48 (i.e., bases GUC of the cleavage sequence) changed to a different base, were prepared as described in Example 2. When these substrates were reacted with the RNA catalyst R51 under standard conditions for 60 minutes as described in Example 3, no cleavage of the substrates occurred. This shows conservation of the GUC sequence of the cleavage sequence of (−)sTRSV RNA. The results of these experiments combined with the results of Examples 13–15 show that the cleavage sequence of (−)sTRSV RNA is NGUC, where N is any base.

Example 26

The vector prepared in Example 23 (hereinafter referred to as "pHC") containing the "hairpin" auto-catalytic cassette was tested for activity in vivo as follows. First, the CAT gene was removed from plasmid pMAMNEO-CAT (purchased from Clontech Inc.) with SmaI and XhoI. It was then ligated using T4 ligase into pHC which had been cut with SmaI and XhoI to produce vector pHC-CAT.

The original vector used in these constructions (pTZ18R; see Example 23) contains an inducible promotor (lacZ) and, as a result of the steps described in Example 23 and immediately above in this example, the CAT gene and the "hairpin" autocatalytic cassette were placed in this inducible region (see FIG. 22A). Also, the CAT gene and "hairpin" autocatalytic cassette were linked so that the expected transcript would be as shown in FIG. 22A (the "CAT-cassette RNA") and so that the RNA sequence coded for by the "hairpin" autocatalytic cassette would be expected to serve as a chain terminator for the CAT transcript by cleaving at the indicated cleavage site (see FIG. 22A). The expected 5' fragment of such a cleavage is also shown in FIG. 22A ("Cleaved CAT-cassette RNA").

Next, PHC-CAT was transfected into *Escherichia coli* strain JM109 (widely available from a number of commercial sources and from the American Type Culture Collection) with calcium chloride and heat shock using standard procedures as described in Maniatis et al., *Molecular Cloning* (1983). Transformed cells containing pHC-CAT were selected on the basis of ampicillin resistance by plating on double concentration YT medium containing 100 ug/ml ampicillin. After selection, the transformed cells were grown overnight in LB broth at 37° C. A fresh culture of these cells was then grown for 5 hours in LB broth at 37° C., after which the cells were induced with 1 mM isopropyl-beta-D-thiogalactoside (IPTG) for one hour to allow expression of the lacZ region, including the CAT gene-cassette RNA transcript.

At the end of this time, RNA was isolated by incubating the cells in 50 mM Tris, pH 8.0, 50 mM ethylenediaminetetraacetic acid (EDTA). 1 mg/ml lysozyme at room temperature for 10 minutes to lyse the cells. The lysate was made to 0.5% sodium dodecyl sulfate (SDS), and then centrifuged to remove cell debris. Phenol was added to the supernatant at a ratio of 1:1, and the supernatant was centrifuged to remove the precipitate. This procedure was repeated, and the resulting aqueous phase was treated with an equal volume of isopropanol at $-20°$ C. for 20 minutes to precipitate the RNA. The precipitate was collected by centrifugation, dried, and redissolved in water.

This isolated RNA was electrophoresed on 1.2% agarose gels containing formaldehyde as described in *Current Protocols In Molecular Biology* (Greene 1989). After electrophoresis, Northern blots were carried out using published methods (*GeneScreen Plus*, DuPont, July 1985). Two DNA probes were used for blotting the gels. The CAT probe was prepared by primer extension of the CAT gene using the Klenow fragment of DNA polymerase I and dATP labelled with alpha $P^{32}$. The "hairpin" autocatalytic cassette probe was prepared by kinasing the DNA complement to the entire "hairpin" autocatalytic cassette RNA sequence shown in FIGS. 20A–20B with dATP labelled with gamma $P^{32}$. The expected positions of binding of these probes to the CAT-cassette RNA and expected 5' fragment are shown in FIG. 22A.

The results of the Northern blot test are shown in FIGS. 22B–22C. As shown there, when the CAT probe was used, the full length CAT-cassette RNA transcript and the expected 5' fragment were detected on the gel, indicating that cleavage had taken place in vivo.

When the "hairpin" autocatalytic cassette probe was used, only the full length CAT-cassette RNA transcript was detected (see FIGS. 22B–22C). The fact that the 5' fragment did not hybridize with this probe was to be expected, since most of the "hairpin" autocatalytic cassette transcript would be in the 3' fragment after cleavage. Although it would be expected that the "hairpin" autocatalytic cassette probe would hybridize to the 3' fragment, the fact that the 3' fragment was not detected by Northern blot analysis is not surprising. The 5' terminus of the 3' fragment would contain a 5'—OH and not the 5'-ppp which is ordinarily seen in RNA transcripts. Thus, the 3' fragment would be expected to be very labile in vivo and was likely degraded immediately after the autocatalytic cleavage.

The mobilities of the CAT-cassette RNA and the Cleaved CAT-cassette 5' fragment on the gel corresponded exactly to the predicted length of the transcripts. The standards run on the gel were *E. coli* 16S and 23S RNA.

An important control was to determine whether cleavage of the target RNA occurred during isolation of the RNA. Intact, uncleaved "hairpin" autocatalytic RNA prepared and separated on an acrylamide gel as described in Example 23 was isolated from the gel using conditions similar to those described above (i.e., no divalent cation, but in the presence of EDTA and SDS). Only intact, uncleaved RNA was obtained when the catalyst was re-electrophoresed on an acrylamide gel.

Example 27

Mammalian expression vector pMHC-CAT containing the "hairpin" autocatalytic cassette linked to the CAT gene was constructed as follows. First, the "hairpin" autocatalytic cassette was removed from the vector pHC (prepared as described in Example 23) by digesting pHC with SmaI/SalI and ligating the resulting fragment to the mammalian vector pMSG (purchased from Pharmacia) at the SmaI/XhoI sites to give pMHC. This operation removed the XhoI site used to clone the "hairpin" autocatalytic cassette insert, but introduced another XhoI site near the 5' end of the insert.

Next, the CAT gene was removed from pMAM-NEO-CAT (Clontech, Palo Alto, Calif.) with SmaI/XhoI and cloned into pMHC at the SmaI/XhoI sites to give the final vector pMHC-CAT which is shown in FIG. 23. Note that the CAT gene and the "hairpin" autocatalytic cassette are both driven by the MMTV LTR promoter which is dexamethasone inducible.

The vector pMHC-CAT was co-transfected into Chinese hamster ovary cells (CHO) by the calcium phosphate method along with the vector pMSG-dhfr (a gift from Dr. Ed Prochownick of the University of Michigan, Ann Arbor, Mich.) which contained a mutant dhfr gene. The isolation of this mutant dhfr gene is described in Simonson and Levinson, *Proc. Nat'l Acad. Sci.* 80, 2495–99 (1983), and pMSG is available from Pharmacia (see above).

Transfectants were selected using gpt medium (*Molec. & Cell. Biol.* 3, 1421–29 (1983)) which kills non-transfected cells. They were next amplified with methotrexate (which amplifies the mutant dhfr gene and associated DNA) to give CHO cells which contained the "hairpin" autocatalytic cassette linked to the CAT gene stably integrated into the genome. Dexamethasone (1 uM) was added to induce expression of the CAT gene and "hairpin" autocatalytic cassette, and RNA was isolated from the individual cells by the guanidinium isothiocyanate procedure (*Current Protocols in Molecular Biology*).

Next, a nuclease protection assay was performed to identify the nature of the transcripts and cleavage products, if any, produced by transcription of the "hairpin" autocatalytic cassette-CAT gene fusion. The probe used in the S1 nuclease assay was prepared from the vector pHC19R. This vector was prepared by removing the "hairpin" autocatalytic cassette from pHC with BamHI/SalI and ligating this fragment into the BamHI/SalI sites of the vector pTZ19R (purchased from US Biochemical) as shown in FIG. 24. Vector pHC19R was linearized with BamHI, transcribed with T7 RNA polymerase using $P^{32}$-CTP as described in Example 2, and the transcript was isolated from 7M urea gels, also as described in Example 2. This RNA probe is 148 nt long and is the complement to the "hairpin" autocatalytic cassette RNA.

The probe was then hybridized in buffer (40 mM Pipes, pH6, 100 mM NaCl, 20% formamide, 1 mM $ZnSO_4$) to RNA (5 ug) isolated from CHO cells that had been transfected with vector pMHC-CAT, and the hybridized RNA was digested with S1 nuclease (100 units, 1 hr., 37° C.). S1 nuclease will digest all single-stranded RNA, but not double-stranded RNA. A negative control was RNA from transfected CHO cells which had not been induced. A positive control was RNA isolated from the pHC plasmid which had been transcribed in vitro with T7 RNA polymerase as described in Example 2.

The S1 digests were electrophoresed on 10% acrylamide-7M urea gels. The results are shown in FIG. 25 where: Lane 1 contains the RNA probe alone; Lane 2 contains the probe digested with S1 nuclease; Lane 3 contains in vitro transcribed "hairpin" autocatalytic cassette RNA, 5'F and 3'F that have been hybridized to probe and digested with S1 nuclease (positive control); Lane 4 contains RNA isolated from CHO cells that had been transfected with pMHC-CAT but were not induced by dexamethasone, hybridized to the probe and digested with S1 nuclease; and Lane 5 contains RNA from CHO cells that had been transfected with pMHC- CAT and induced with dexamethasone, hybridized to the probe and digested with S1 nuclease. All mobilities were as expected, and, as can been seen in Lane 5, RNA transcribed from the "hairpin" autocatalytic cassette-CAT gene fusion was cleaved in vivo into the expected products.

Another control was uncleaved "hairpin" autocatalytic cassette RNA hybridized to the probe, S1 nuclease digested and electrophoresed under the same conditions. No cleavage products were seen (data not shown). This control shows that cleavage of the "hairpin" autocatalytic cassette RNA did not occur as a result of the analysis conditions and, therefore, that the cleavage products seen in Lane 5 must have been produced as a result of in vivo cleavage of the hybrid CAT-"hairpin" autocatalytic RNA.

Example 28

The following example illustrates in vivo activity of the "hairpin" catalytic RNA in plants. The "hairpin" autocatalytic cassette (see Example 23) was ligated to cauliflower mosaic virus (CMV) in a viral vector. Plants were then transformed with the resulting vector and, during replication of the virus, the "hairpin" autocatalytic cassette RNA cleaved the viral RNA intramolecularly. The viral RNA serves as a template for viral replication and for attenuation of the virus. Since cleavage levels of the "hairpin" autocatalytic cassette were about 50–60% in vitro, attenuated viral infection in these plants would be expected if the "hairpin" autocatalytic cassette RNA linked to the CMV RNA did cleave in vivo in the plants, and this was what was observed.

The constructions tested had the "hairpin" autocatalytic cassette in the sense and antisense orientation. They are shown in FIG. 26.

These constructions were made by removing the "hairpin" autocatalytic cassette from vector pHC (prepared as described in Example 23) with XhoI/SalI and ligating this fragment into the unique XhoI site of CMV plasmid pCS101 (a gift from Dr. Art Hunt, University of Kentucky). Plasmid pCS101 contains the entire CMV sequence. The XhoI site is located in gene II of CMV and was chosen because DNA can be cloned into this site without subsequently interfering with plant infection. Another plasmid identical to pCS101, except having a pBR322 bacterial replicon, is available from American Type Culture Collection, and can be used in its place as a source of CMV. The "hairpin" autocatalytic cassette could be inserted in either of two orientations (sense or antisense) since XhoI and SalI ends are compatible.

The resulting constructions were grown in XL-1 blue *E. coli* (Stratagene), and clones of the "hairpin" autocatalytic cassette insert were isolated and identified by cleaving with KpnI and by electrophoresing the insert on 1% agarose gels. The isolated clones were pCS101HC7 and pCS101HC9 which had the "hairpin" autocatalytic cassette in the sense and antisense orientation, respectively. These constructions are shown in FIG. 26. Construction pCS101HC7 was designed so that CMV 35S RNA containing the "hairpin" autocatalytic cassette would be transcribed from it and cleaved if the "hairpin" autocatalytic cassette was active in vivo.

After being grown in *E. coli*, the constructions were cut with SalI, and were rubbed onto 10 turnip (*Brassica campestis*) plants (0.5 ug DNA/plant) which were three weeks old. Four groups of plants were treated as follows:

A. Control-mock inoculated (no virus)

B. Virus control - no "hairpin" autocatalytic cassette insert - pCS101

C. Virus with the sense "hairpin" autocatalytic cassette - pCS101HC7

D. Virus with the antisense "hairpin" autocatalytic cassette - pCS101HC9

The plants were checked weekly for viral symptoms. Within six weeks, plants treated with wild-type virus were observed to have viral symptoms, including vein clearing, leaf wrinkling and a yellow mosaic pattern on the leaf. In turnips treated with pCS101HC7, the onset of symptoms was delayed 7–10 days as compared to turnips infected with wild-type virus, and the severity of the symptoms never reached the levels attained with the wild-type virus. The following was observed when the plants were nine weeks old:

| Treatment | Symptoms |
|---|---|
| A | No symptoms |
| B | Viral symptoms, worst case, most yellowing (chlorosis) and most lesions. |
| C | Viral symptoms, distinct chlorosis and lesions, but much less than in the virus control. |
| D | Viral symptoms, less than viral control, but not as much yellowing as the virus with the sense "hairpin" autocatalytic cassette. Some plants looked uninfected. |

These results indicate that a "hairpin" catalytic RNA according to the invention can cleave viral RNA in which it is inserted so that the viral infection is attenuated (Treatment C). Surprisingly, viral attenuation was also obtained with the "hairpin" autocatalytic cassette linked to the viral DNA in the antisense direction (Treatment D). This is believed to be due to the deletion or disabling of the viral construct containing the antisense catalyst, so that viral replication is diminished compared to virus control (Treatment B).

Next, RNA was isolated from the leaves of the nine-week old plants, a probe was prepared and hybridized to the isolated RNA, S1 nuclease digestion was carried out, and the S1 digests separated on 10% acrylamide-7M urea gels and analyzed by autoradiography, all as described in Example 27. The probe used was $P^{32}$-labelled autocatalytic cassette RNA. The results are shown in FIG. 27A, where the 3'F and 5'F resulting from in vivo RNA cleavage were found only in plants infected with pCS101HC7 having the "hairpin" autocatalytic cassette inserted in the sense direction (see Lane 5). None of the other control plants, including those infected with the antisense construct pCS101HC9, showed these cleavage products, (see Lanes 3, 4 and 6).

RNA isolated from the leaves of the nine-week old plants was also subjected to Northern blot analysis. Total RNA was prepared by the guanidium thiocyanate method (Chirgwin et al., *Biochemistry*, 18, 5294–99 (1979)) followed by pelleting through a 5.7M CsCl step gradient. Then, 2.5 ug of total RNA was denatured at 65° C. for 5 min. with formaldehyde and formamide. The denatured RNA was then electrophoresed on a 1% agarose/ formaldehyde gel, and the RNA was transferred to a Duralon-UV nylon filter (Stratagene) in 10× standard sodium citrate (SSC) (0.15M). After UV crosslinking, the filter was prehybridized in 6× SSC and 0.05× BLOTTO (Sambrook, Fritsch and Maniatis, *Molecular Cloning* § 1.102 (2nd ed. 1989)) for 3 hrs at 68° C. The "hairpin" autocatalytic cassette fragment was labeled with $P^{32}$ using the oligolabeling procedure of Feinberg and Vogelstein, *Anal. Biochem.*, 132, 6–9 (1983). Then it was heated to 100° C. for 5 min. and cooled on ice. This probe was added to the prehybridization mix, and incubation was continued at 68° C. overnight. The nylon filter was washed once in 2× SSC, 0.1% SDS for 20 min. at room temperature, followed by washing with 1× SSC, 0.1% SDS for 60 min. at 68° C. and 0.1× SSC, 0.1% SDS for 60 min. at 68° C. The filter was then exposed overnight to Kodak X-OMAT film using two lightning plus screens. The results are shown in FIG. 27B. Of interest is the detection of viral RNA transcripts of about the size expected before cleavage (8 Kb) and after cleavage (6 Kb and 2 Kb) following infection with pCS101HC7 (Lane 3).

Some reproducible size heterogenity was observed in the S1 fragments and in the Northern blots. This may be due to the rapid degradation by plant nucleases of these RNA fragments which contain either a 2'-3' cyclic phosphate or a 5' hydroxyl after ribozyme cleavage. The 5' hydroxyl could mimic naturally occurring RNA degradation signals. After infecting turnips with pCS101HC7, RNAs of the sizes expected before and after RNA cleavage were detected, but the amount of the 6 Kb fragment detected was somewhat less than the 2 Kb fragment. This could be due to enhanced stability of 2 Kb transcript which contained a cyclic phosphate over the 6 Kb transcript which contained the 5' hydroxyl.

To determine if the DNA encoding the "hairpin" autocatalytic ribozyme was stable in vivo, total DNA was isolated from the leaves of mock-inoculated turnips, turnips inoculated with wild-type CMV (pCS101) and turnips inoculated with pCS101HC7. DNA was isolated from plants essentially as described in Murray and Thompson, *Nucleic Acids Research*, 8, 4321–25 (1980). Oligonucleotide primers homologous to domains 5' and 3' to the XhoI site of the parental CMV clone pCS101 were used as primers to amplify DNA sequences between these domains by polymerase chain reaction (PCR). Primer 1, which includes an EcoRI site, hybridizes 63 bases upstream from the XhoI site and has the following sequence:

5'-GGAATTCACC CGTCAGTTTT TAATACTGC-3' [SEQ ID 16]

Primer 2 includes a BamHI site and hybridizes 54 bases downstream from the XhoI site and has the following sequence:

5'- TGGATCCATT CTAGTATTTTG AGCTTCT-3' [SEQ ID 17]

The primers were synthesized on an Applied Biosystem 391 PCR-MATE using phosphoramidite chemistry. PCR was performed as described by the vendor of TaQ polymerase (Perkin-Elmer). Briefly, PCR conditions were 94° C. for 1 min., 55° C. for 2 min. and 72° C. for 3 min. for 35 cycles. After PCR amplification, the amplified DNA was size fractionated on a 2% agarose gel and stained with ethidium bromide.

The results are shown in FIG. 27C. When total plant DNA from mock-infected turnips was fractionated, no bands were observed (FIG. 27C, lane 1). Total DNA isolated from plants infected with wildtype CMV gave an expected band of about 123 bp (FIG. 27C, lane 2). DNA isolated from plants infected with pCS101HC7 gave an expected band of 225 bp (FIG. 27C, lane 3). In the latter two cases, the amplified DNA was the same size as those bands amplified using the intact plasmids pCS101 and pCS101HC7 (FIG. 27C, lanes 4 and 5). These results indicate that at least the majority of the DNA coding for the "hairpin" autocatalytic ribozyme was retained intact in the viral genome after infection.

Finally, protein extracts were prepared from plants that were mock-inoculated, inoculated with wild-type CMV and inoculated with pCS101HC7, and the levels of CMV coat protein in the extracts determined by Western immunoblot. The extracts were prepared by homogenizing turnip leaf tissue in an equal volume of phosphate buffered saline using a mortar and pestle. Samples were boiled for 10 min. and then spun down in a microfuge for 10 min. at 4° C. Protein concentrations of the supernatants were determined by the method of Bradford, *Anal. Biochem.*, 72, 248–54 (1976), and the extracts were diluted with an equal volume of 4× Laemmli sample buffer and denatured at 100° C. for 5 min. (Laemmli, *Nature*, 227, 680–85 (1970)). The samples were next electrophoresed on 10% SDS-polyacrylamide gels with 5% stacking gel (id.), followed by electrotransfer of the proteins to nitrocellulose at 45 volts, 1.25 hours, in transfer buffer as described in Towbin et al., *Proc. Natl. Acad. Sci. USA*, 76, 4350–54 (1979). Prestained molecular weight markers (BRL) were used to confirm protein transfer. Nonspecific antibody binding was avoided by using blocking solution (Johnson et al., *Gene Anal. Techn.*, 1, 3–8 (1984)). All antibody incubations were done at 22° C. with gentle agitation. The primary antibody was rabbit antiserum to CMV coat protein (1:1000 dilution in blocking solution) provided by Dr. R. Shepherd, University of Kentucky. An anti-rabbit IgG alkaline phosphatase conjugate (Sigma, St. Louis) was used as the secondary antibody (1:1000 dilution in blocking solution). Visual detection of proteins was accomplished using BCIP/NBT (Sambrook et al., *Molecular Cloning: A Laboratory Manual* (2nd ed. Cold Spring Harbor Laboratory 1989)).

The results are presented in FIGS. 27D and 27E. No coat protein was observed in extracts from mockinoculated plant tissues one or two months after infection (FIGS. 27D and 27E, lane 1). In extracts from plants inoculated with wild-type virus, coat protein was found in significant quantities at one month and two months post infection (FIGS. 27D and FIG. 27E, lane 2). One month after infection with the ribozyme construct pCS101HC7, very little coat protein was detected (FIG. 27D, lane 3). Two months after infection with pCS101HC7, increased levels of coat protein approaching those found after wild-type CMV infection were detected (FIG. 27E, lane 3).

The combined results of the pathological observations and the S1 nuclease, Northern blot, PCR amplification and Western immunoblot assays provide conclusive evidence that the "hairpin" catalytic RNA cleaved viral RNA in vivo in plants.

Example 29

A highly conserved sequence in HIV-1 viral RNA has been discovered which has favorable properties as a potential target site for a suitably engineered "hairpin" catalytic RNA. The 16-base sequence is shown in FIG. 28. Cleavage occurs between the two bases found at positions 111/112 as counted from the 5' cap site (all HIV-1 sequences are from the HIV Sequence Data Base, prepared and distributed by Gerald Myers et al., Los Alamos National Laboratory, Los Alamos, N.Mex., telephone (505) 665-0480).

When various HIV-1 isolates were compared, only two isolates showed variations in the sequence, and the variations were, in each case, only a single base change (see FIG. 29) (sequences shown in FIG. 29 are from the HIV Sequence Data Base). The conserved target site sequence is found in the 5' leader region of all nine HIV-1 mRNAs (see FIG. 28). Thus, a catalytic RNA engineered to cleave the conserved target sequence should cleave all of these mRNAs and, thereby, prevent or reduce the spread of the virus.

A "hairpin" catalytic RNA was designed according to the principles set forth herein to cleave the conserved target sequence. The catalytic RNA sequence, designated herein as "RHIV", is shown in FIG. 30. RHIV was designed so that it would base pair with the target sequence in the two regions flanking the CGUC cleavage sequence (see FIG. 30). The "hairpin" portion of RHIV has the same sequence as the "hairpin" portion of the (−)sTRSV catalytic RNA sequence shown in FIG. 1. Bases 3'-CUGAGGG-5' at the 5' end of RHIV are vector bases and are not necessary for activity of the catalyst. RHIV was synthesized as described in Example 2.

A substrate RNA containing the conserved 16-base target site sequence shown in FIG. 28 plus additional GCG vector bases at its 5' end was also synthesized as described in Example 2. This substrate RNA is designated herein as "SHIV". The sequence of SHIV is shown in FIG. 30.

The substrate RNA SHIV and catalytic RNA RHIV were then reacted under standard conditions as described in Example 3 over a period of time from 0 to 280 minutes. The concentration of substrate SHIV was 0.025 uM, and the concentration of RHIV was 0.005 uM. Cleavage of substrate SHIV (which contains the conserved HIV-1 sequence) by the engineered "hairpin" catalytic RNA RHIV was obtained (see FIGS. 31A–31B).

The kinetics of the reaction between SHIV and RHIV were investigated using the methods described in Example 5. The results are shown in FIGS. 32A–32B. The time of incubation was 5 minutes, and the concentration of RHIV was 0.005 uM. The concentration of SHIV was: Lane 1—0.10 uM; Lane 2—0.05 uM; Lane 3—0.025 uM; Lane 4—0.012 uM; Lane 5—0.006 uM; and Lane 6—0.025 uM (this is the control lane at zero time).

The rate of cleavage (turnover number, kcat) was determined to be 1.6/minute (see FIGS. 32A–32B). This is a very rapid rate when compared to any other catalytic RNA under the mild conditions of temperature, pH and salt concentration used. The Km was determined to be 100 nM (see FIGS. 32A–32B), which is also very small for an RNA catalyst under these conditions. The low Km indicates that the reaction proceeds very well at extremely low concentrations of substrate.

Next, the ability of the catalytic RNA RHIV to cleave a long HIV-1 transcript was tested. The RNA used as a target sequence was a 183 nt-long transcript containing 107 nt of HIV-1 sequence. The target transcript was made by T7 RNA polymerase transcription (as described in Example 2) of the HaeII-linearized plasmid pROS. This plasmid was obtained from Dr. John Rossi of the City of Hope Medical Center, Duarte, Calif. Plasmid pROS has the 5'- HindIII fragment of the HIVHXB2 isolate cloned into plasmid pBluescript II (Stratagene, LaJolla, Calif.). The 5'- HindIII fragment of HIVHXB2 contains the sequence (+) 77 to (+) 635 from the 5' cap site (sequence obtained from the HIV Sequence Data Base). The 183 nt transcript contains 76 nt of vector sequence at the 5' end, followed by 107 nt of HIV-1 sequence (the sequence from (+) 77 to (+) 183 from the 5' cap site).

This 183 nt transcript (5 nM) was incubated with catalytic RNA RHIV (25 nM) under standard conditions for 60 minutes as described in Example 3. When the products were analyzed on 6% acrylamide-7M urea gels, cleavage was seen to have occurred (see FIGS. 33A–33B). All mobilities in FIGS. 33A–33B were as expected. This result shows that RHIV, a "hairpin" catalytic RNA according to the invention, can cleave a long HIV-1 RNA transcript in vitro under conditions near physiological for mammalian cells.

Example 30

As a prerequisite for in vivo experiments, it was necessary to develop a system for the proper termination of the "hairpin" catalytic RNA RHIV when it was transcribed in vivo. Such a system was developed by cloning DNA coding for RHIV into the BamHI/MluI sites of the vector pHC (prepared as described in Example 23) to give plasmid pHR (see FIGS. 34A–34B). In plasmid pHR, DNA coding for RHIV is 5' to DNA coding for the autocatalytic cassette RNA (see FIGS. 20A–20B).

Plasmid pHR was transcribed with T7 RNA polymerase and the resulting 101 nt RNA (see FIGS. 34A–34B) isolated, all as described in Example 2. The catalytic activity of this 101 nt RNA transcript (designated herein as "PRHIV") was assayed against the substrate SHIV (see FIG. 30) as described in Example 3. The concentration of catalytic RNA (RHIV or PRHIV) was 0.025 uM, and the concentration of SHIV was 0.10 uM. The 101 nt PRHIV had the same catalytic activity as the shorter RHIV (see FIG. 35 where R designates RHIV and PR designates PRHIV), indicating that the extra sequence at the 3' and 5' ends (see FIGS. 34A–34B) did not interfere with cleavage of the substrate.

Next, a mammalian expression vector was prepared by removing DNA coding for RHIV and the autocatalytic cassette RNA from pHR with SmaI/SalI (see FIGS. 34A–34B). The resulting fragment was cloned into the mammalian vector pMSG (see Example 27) cut with SmaI/SalI to give pMSGRHIV (see FIG. 36). In pMSGRHIV, the catalytic RNA is driven by the MMTV promoter which is dexamethasone inducible.

Vector pMSGRHIV has been used to transfect human cells which were then infected with HIV-1. Preliminary results show that the amount of tat and gag mRNAs produced in transfected cells was lower than the amount produced in control cells.

Example 31

In this example, evidence is presented showing the in vivo down regulation of two genes in mammalian cells by using "hairpin" RNA catalysts in trans. The two genes studied were hypoxanthine guanosine phosphoribosyl transferase (HGPRT) and chloramphenicol acetyl transferase (CAT).

A. In Vivo Inhibition of HGPRT

A 15 nt target sequence in the HGPRT gene of the hamster was identified. The sequence is:

AUUCC*GUCAUGGCGA [SEQ ID 18]

A "hairpin" catalytic RNA was designed according to the principles set forth herein to cleave this target sequence. The catalytic RNA sequence, designated "RHGPT," is shown in FIG. 37. RHGPT base pairs with the target sequence in the two regions flanking the CGUC cleavage sequence, and the "hairpin" portion of RHGPT has the same sequence as the "hairpin" portion of the (−)sTRSV catalytic RNA sequence shown in FIG. 1. Additional vector bases coding for restriction sites are present at the 3' and 5' ends of RHGPT.

RHGPT and the target sequence were synthesized as described in Example 2 and tested in vitro as described in Example 3. The results of the test showed that the target sequence was cleaved in vitro by the engineered "hairpin" ribozyme RHGPT at the * in the sequence given above (which is after nt87 in the sequence of the HGPRT gene).

Next, DNA coding for ribozyme RHGPT was cloned into the BamHI/MluI sites of the mammalian expression vector pHC (prepared as described in Example 23). The DNA coding for RHGPT and HC was excised from the resulting plasmid with SmaI/SalI and cloned into SmaI/SalI digested pMSG (Example 27) to give plasmid pMRHPT, a map of which is shown in FIG. 37. The DNA coding for RHGPT is located downstream of the dexamethasone-inducible MMTV promoter on pMRHPT and upstream of the "hairpin" auto-catalytic cassette (HC) which is included so that RHGPT will be properly terminated at the 3' end after the RNA is transcribed.

Another plasmid, pMR2HPT, was also prepared. This plasmid is identical to pMRHPT, except that a G35→C mutation in RHGPT was made (numbering according to FIG. 42D). Accordingly, the resulting ribozyme produced by this plasmid would be inactive (see Example 22).

Chinese hamster ovary cells (CHO) were co-transfected with one of these plasmids and plasmid pMSG-dhfr. The method of transfection and plasmid pMSG-dhfr are described in Example 27. Transfectants were selected and amplified with methotrexate, also as described in Example 27. A schematic drawing of the selection scheme is presented in FIG. 38.

The poison 8-azaguanine, which is allowed into cells by the HGPRT enzyme, was then added to the cells (80 µg/ml) both in the presence and absence of dexamethasone (1 µM) which induces the HGPRT ribozyme. In the absence of dexamethasone, cells with or without DNA coding for RHGPT died as expected. In the presence of dexamethasone, control cells died, but colonies of survivors were seen for cells transfected with pMRHPT. All cells transformed with pMR2HPT (coding for the inactive ribozyme) died.

To quantitate the rate of survival, CHO cells were grown in gpt medium (see Example 27), except untransfected, uninduced CHO cells which were grown in MEM. The concentration of 8-azaguanine used was 80 µg/ml, and the concentration of dexamethasone used was 1 µM. One hundred cells were plated per dish. Colonies of cells were stained with crystal violet. The results are presented below:

| Cells | Percent Survival |
|---|---|
| Untransfected, uninduced | 100%* |
| Transfected with pMRHPT and induced | 33% |
| Transfected with pMRHPT but uninduced | 0% |
| Transfected with pMR2HPT and induced | 0% |

*Results were normalized with untransfected, uninduced cells set at 100%. Actual survival rate for these cells was 80%.

The results are consistent with reduced levels of HGPRT due to the cleavage of HGPRT mRNA by the engineered "hairpin" ribozyme RHGPT after induction with dexamethasone. The in vivo activity of the ribozyme is not likely due to antisense effects, since the disabled ribozyme coded for by pMR2HPT was ineffective in increasing resistance to 8-azaguanine. Note that the mutation in pMR2HPT is not in the area of the ribozyme that base pairs to the substrate, so binding to the substrate should occur.

Next, an S1 nuclease assay was performed to observe the in vivo levels of mRNA coding for HGPRT. The S1 nuclease assay was performed as described in Example 27. The 148 nt probe which was used hybridizes to HGPRT mRNA and was prepared by transcribing plasmid pHPTPr as described in Example 27 using $P^{32}$-labelled CTP. Plasmid pHPTPr contains the antisense HGPRT sequence from nt 20–160 (Konecki et al., *Nucleic Acids Res.*, 10, 6763–75 (1982)) bridging the cleavage sequence at nt 87 cloned into pTZ18R (US Biochemical) between the EcoRI and HindIII sites.

The results are shown in FIG. 39. In FIG. 39, lane 3 contains RNA from cells transfected with pMRHPT and pMSG-dhfr but not induced, and lane 4 contains RNA from cells transfected with pMRHPT and pMSG-dhfr which were induced with dexamethasone. A 30% reduction in the level of mRNA was observed when the "hairpin" ribozyme was induced (compare lanes 3 and 4). This shows that the engineered "hairpin" ribozyme RHGPT reduces HGPRT activity by lowering the amount of mRNA, and the likely mechanism is cleavage of the HGPRT mRNA.

B. In Vivo Lowering of CAT mRNA Levels.

From a series of in vitro experiments using the techniques described in Examples 2 and 3, the optimum target sequence in the CAT gene was determined to be:

5'- UUUCA*GUCAGUUGCUCAA-3'   [SEQ ID 5]

with cleavage at (*), which is nt 320 of the CAT gene. The "hairpin" catalytic RNA designed to cleave this target sequence, designated "RCAT," is shown in FIG. 40. RCAT was designed according to the principles set forth herein. It base pairs with the target sequence in the two regions flanking the AGUC cleavage sequence, and the "hairpin" portion of RCAT has the same sequence as the "hairpin" portion of the (−)sTRSV catalytic RNA sequence shown in FIG. 1. Additional vector bases coding for restriction sites are present at the 3' and 5' ends of RCAT.

DNA coding for RCAT was ligated to pHC (Example 23) which had been cut with BamHI/MluI. The resulting plasmid was cut with SmaI/SalI to remove the fragment coding for RCAT and HC. This fragment was ligated to pMSG (Example 27) which had been cut with SmaI/SalI to give pMSGRCAT. Next pCAT (Promega) was cut with PvuI/PstI, and the fragment containing the CAT gene under the control of the SV40 promoter and enhancer was isolated on a 1% low-melting agarose gel (Nusieve). Then the fragment was blunt ended with Klenow fragment and ligated into the EcoRI-cut, blunt-ended pMSGRCAT to give the final plasmid pMCATRCAT (see FIG. 40). This plasmid contains DNA coding for RCAT under control of the dexamethasone-inducible MMTV promoter and the CAT gene under control of the SV40 promoter. Further, DNA coding for the auto-catalytic "hairpin" ribozyme is located downstream of DNA coding for RCAT so that RCAT will be properly terminated at the 3' end upon transcription of the RNA.

Plasmid pMCATRCAT was cut with NdeI and then used to transfect CHO cells along with XhoI-cut pMSG-dhfr as described in Example 27. Transfectants were selected and amplified and an S1 nuclease assay performed, all as described in Example 27. The probe used for the S1 nuclease assay was RNA transcribed from the plasmid pCAT. This plasmid contains the sequence of the CAT gene from nt 260–372 (GenBank sequence) bridging the cleavage sequence at nt 320 cloned into the EcoRI/HindIII site of pTZ18R (US Biochemical) in the antisense direction. The probe was prepared as described in Example 27 using $^{32}$p-CTP and was a total of 119 nt long.

The results of the S1 nuclease assay are presented in FIG. 41. A reduction in CAT mRNA was observed in cells transfected with pMCATRCAT and pMSG-dhfr and induced with dexamethasone as compared to uninduced cells. Thus, the engineered "hairpin" catalyst RCAT did reduce the level of CAT mRNA. However, further attempts to locate the mRNA cleavage products have so far failed, and no lowering of CAT enzymatic activity was seen.

Example 32

Additional mutagenesis experiments were performed changing bases in (−)sTRSV RNA and its substrate. All substrate RNAs and catalytic RNAs were prepared as described in Example 2. Mutagenesis was carried out simply by making the required base change in the synthetic DNA template. All catalytic RNAs had additional vector bases GGG at the 5' end, and all substrate RNAs had additional vector bases GCG at the 5' end. These bases are required for efficient transcription (Milligan et al., *Nucleic Acids Res.*, 15, 8783–98 (1987)), and the C near the 5' end of all substrates ensured at least one $P^{32}$- labelled C in the 5' cleavage fragment. The reference sequences were the unmutated catalytic and substrate sequences (see FIG. 1).

Substrate and catalytic RNAs were assayed for catalytic activity as described in Example 3. Generally, the final concentrations of substrate RNA was 0.1 uM, and the final concentration of catalytic RNA was 0.01 uM. Assays were done at 37° C. for times ranging from 15–30 minutes, and a zero-time control was always included. Reaction products were analyzed on 15% acrylamide/7M urea gels, autoradiography performed, and the bands cut from the gels and counted. The control (unmutated ribozyme/ substrate) was assayed at the same time as all mutant catalytic RNAs and substrates.

Nucleotide changes made in the native, unmutated sequence of both the catalytic RNA and the substrate showed a range of catalytic effects. The nucleotide changes shown in FIG. 42A had very little effect on the catalytic activity of the ribozyme (75–100% of the activity of the unmutated sequence), while other nucleotide changes (FIG. 42B) had an intermediate effect on catalytic activity (5–75% of the activity of the unmutated sequence). Those mutational changes resulting in very low or no catalytic activity (less than 5% of the activity of the unmutated sequence) are shown in FIG. 42C. The results further define the two-dimensional structure of the (–)sTRSV catalytic complex. A revised "hairpin" structure for the catalytic complex is shown in FIG. 42D. In FIGS. 42A–D, the ribozyme is numbered consecutively 1–50 nt and the substrate 1–16 nt (see FIG. 42D). Also, in FIGS. 42A–D, upper case letters are used for the ribozyme nucleotides and lower case letters are used for the substrate nucleotides.

In summary, the results show that Helices 2 and 3 (see FIG. 42D) are not continuous but have an unpaired base between them. Helix 4 was found to be shorter and Loops II and IV were found to be larger than previously predicted by computer modeling. Also, certain bases in Loops II and IV were found to be invariant. Helix 4 can be extended towards the closed end (Loop III) of the "hairpin" to give increased stability to the ribozyme, and the sequence of Loop III can be mutated with retention of catalytic activity. While conventional base pairing interactions between Loop I on the ribozyme and Loop V of the substrate were not observed, an A→C mutation in ribozyme Loop I partly restored activity to a previously inactive c→a mutation in substrate Loop V, indicating that some type of interaction between these two bases may be occurring. Finally, the data show that the first base pair upstream of the N*GUC cleavage sequence cannot be an A:U or U:A, it must be G:C or C:G. It is believed that the G:C or C:G base pair is necessary for stability of the catalyst-substrate complex and that A:U or U:A base pairs can be used if sufficient stability is provided by other means such as possibly lengthening Helix 1. Indeed, it has been found that A:U and U:A base pairs can be used at these positions in the synthetic autocatalytic catalyst of the invention. Accordingly, in engineering a "hairpin" catalyst based on (–)sTRSV, the substrate RNA preferably contains the target sequence 5'- SN*GUC-3', where S is G or C and cleavage occurs at the *.

The results will now be discussed in detail. First, Table I lists all substrate sequences successfully cleaved by a catalytic RNA designed according to the "hairpin" model so that the bases flanking the N*GUC cleavage sequence in the substrate were base paired to the catalyst. Cleavage occurred at the *. The lower case letters in Table I designate additional vector sequence.

TABLE 1

|    | | Helix2 | LoopV Helix1 | |
|----|-----|------|----------------|----------|
| 1  | gcg | UGAC | A*GUC CUGUUU   | [SEQ ID 10] |
| 2  | gcg | UGAC | A*GUC CUGUUUUUUU | [SEQ ID 20] |
| 3  | gcg | UGAC | A*GUC CUGUUUUUUCGC | [SEQ ID 21] |
| 4  | gcg | UGUC | A*GUC CUGUUU   | [SEQ ID 22] |
| 5  | gcg | UGAG | A*GUC CUGUUU   | [SEQ ID 23] |
| 6  | g   | AAAC | A*GUC CCCAAC   | [SEQ ID 24] |
| 7  | g   | UUUC | A*GUC AGUUGC   | [SEQ ID 25] |
| 8  | gcg | UUUC | A*GUC AGUUGCUCAA | [SEQ ID 26] |
| 9  | gcg | CCCC | U*GUC CCCGAG   | [SEQ ID 27] |
| 10 | gcg | UGGG | U*GUC GACAUAgc | [SEQ ID 28] |
| 11 | gcg | UGAC | A*GUC GUGUUU   | [SEQ ID 29] |
| 12 | gcg | UGAC | A*GUC AUGUUU   | [SEQ ID 30] |
| 13 | gcg | AGAG | C*GUC GGUAUUAA | [SEQ ID 31] |
| 14 | gcg | AGAG | C*GUC GGUAUUAAGCGG | [SEQ ID 32] |
| 15 | gcg | AGAG | C*GUC GGUAUUAAGC | [SEQ ID 33] |
| 16 | gcg | UUUC | U*GUC GUUUAACU | [SEQ ID 34] |
| 17 | gcg | UGAC | U*GUC CUGUUU   | [SEQ ID 35] |
| 18 | gcg | UGAC | C*GUC CUGUUUL  | [SEQ ID 36] |
| 19 | gcg | UGAC | G*GUC CUGUUU   | [SEQ ID 37] |
| 20 | gcg | UGCC | C*GUC UGUUGUGUGA | [SEQ ID 38] |
| 21 | gcg | UGCC | C*GUC UGUUGUGU | [SEQ ID 39] |
| 22 | gcg | CCAC | U*GUC GAUCGA   | [SEQ ID 40] |
| 23 | gcg | CCAC | U*GUC GAUCGAG  | [SEQ ID 41] |
| 24 | gcg | AUUC | C*GUC AUGGCGA  | [SEQ ID 42] |
| 25 | gcg | AUUC | C*GUC AUGGC    | [SEQ ID 43] |
| 26 | gcg | AUGC | G*GUC ACUCAUUA | [SEQ ID 44] |
| 27 | gcg | AUGC | G*GUC ACUCAU   | [SEQ ID 45] |
| 28 | gcg | AUCC | U*GUC CAUUCAA  | [SEQ ID 46] |
| 29 | gcg | AUCC | U*GUC CAUUCAAG | [SEQ ID 47] |
| 30 | gcg | UUGG | U*GUC GACCUGAA | [SEQ ID 48] |
| 31 | gcg | ACAG | C*GUC UGCUCC   | [SEQ ID 49] |
| 32 | gcg | UUGC | G*GUC GCUACG   | [SEQ ID 50] |
| 33 | gcg | UUGC | G*GUC GCUACGUC | [SEQ ID 51] |
| 34 | gcg | UCUC | A*GUC ACUAUG   | [SEQ ID 52] |
| 35 | gcg | CACC | U*GUC ACAUAA   | [SEQ ID 53] |
| 36 | gcg | CACC | U*GUC ACAUAAUU | [SEQ ID 54] |
| 37 | gc  | GUGG | U*GUC UGUGGA   | [SEQ ID 55] |

As shown in Table I, every base pair in Helices 1 and 2 can be changed to any other base pair, and the substrate will be cleaved by the ribozyme, except the base pair in Helix 2 adjacent to the N*GUC cleavage sequence (designated by S in FIG. 42D). When base G11 in the ribozyme was changed to C, catalytic activity was lost (see FIG. 42C). When a second mutation (c4→g) was made in the substrate so that base pairing was restored, catalytic activity was also restored. However, when catalysts and substrates having A:U base pairs at these positions were tested, no catalytic activity was observed. A:U base pairs in this position were checked for catalytic activity with a variety of substrates and corresponding ribozymes, and all of them were found to be inactive. Accordingly, this base pair must be G:C or C:G and cannot be A:U or U:A unless, as discussed above, other measures are taken to stabilize the substrate-catlyst complex.

As already demonstrated in Examples 18 and 21, it is possible to adjust the length of Helix 1 to optimize the rate of cleavage. In particular, when the native sequence was extended four base pairs by adding four A:U base pairs to the open end of Helix 1, an increased rate of activity was seen (Example 21). However, when three additional G:C base pairs were added in the present experiments, a large loss of activity occurred. This phenomenon was observed for numerous substrates and ribozymes. Accordingly, Helix 1 has an optimal length for each substrate used.

A type of "hinge" region, consisting of a single A base at position 15, is present between Helices 2 and 3 of the catalytic RNA (see FIG. 42D). When the A15:U49 potential base pair was changed to the compensatory base pair U15:A49 by a double mutation, activity remained at nearly 100% (FIG. 42A). The single U49→A49 mutation, which would lead to an A:A mismatch, also had no effect on activity (FIG. 42A), showing that no base pair was needed at this position. Accordingly, the results show that a base pair does not exist between bases A15 and U49 of the ribozyme.

Proof of the base pair C17:G47 was obtained previously (see Example 22), but the presumptive base pair next to it, C16:G48, could not be shown to exist. Both the catalyst containing the C:C mismatch and the catalyst containing the reverse G:C base pair were inactive (FIG. 42C). Since this G and C are opposite each other in this position and are adjacent a base pair, it is highly likely they are actually base paired as well. However, the fact both the mismatch and reverse base pair were inactive suggests that the identity of the bases must be maintained in this position. Thus, it is likely that this base pair exists and must be C16:G48 as shown.

At the end of Helix 3 is the predicted base pair G19:C45. The catalyst containing the C:C mismatch was inactive (FIG. 42C), and the catalyst containing the reverse base pair C19:G45 was partially active (FIG. 42B), indicating that a base pair likely exists in this position.

Base pairing between A18:U46 is shown in FIG. 42D even though mutagenesis was not done. The existence of a base pair at this position is likely since it would be located between two proven G:C base pairs.

Helix 4 is a shorter helix than predicted by straightforward computer modeling and two-dimensional energy minimization (compare FIGS. 1 and 19 with FIG. 42D). This helix was previously shown to exist by showing that the base pair C27:G35 actually existed (see Example 22). The next base pair downstream, A28:U34, also exists. Catalysts containing the single mismatch mutations, U34→A or C, were inactive (FIG. 42C), and catalysts containing the compensatory double mutations to form either U28:A34 or G28:C34 base pairs restored activity (FIG. 42A).

The following results show that an active ribozyme is produced when Helix 4 is extended and the sequence of Loop III is changed. As shown in FIG. 42A, Loop III was replaced with the common and very stable RNA hairpin sequence 5'-GGAC(UUCG)GUCC-3' [SEQ ID 1] characterized by Tinoco and colleagues (Cheong et al., Nature, 346, 680–82 (1990)); Varani et al., Biochem., 30, 3280–89 (1991). As a result of this substitution, Helix 4 was extended by four base pairs and the GUU sequence of Loop III was replaced with the sequence UUCG (see FIG. 42A). The resulting RNA catalyst was active. In fact, the activity of this ribozyme was greater than that of the unmutated form. Further, the mutant ribozyme was more thermal stable. It remained active at 45° C., while the unmutated RNA catalyst loses most of its activity at this temperature (see FIG. 43).

It was concluded from this experiment that Loop III does not have a conserved or invariant base sequence and that Helix 4 can be extended towards loop III by at least four base pairs without loss of activity. The four additional base pairs in Helix 4 should provide helix stabilization of this region. The secondary folding energy of Helix 4 and Loop III in the native structure is +0.6 Kcal/mole, while that of the catalyst having the extended Helix 4 and the Loop III of the sequence UUCG was determined to be −11.1 Kcal/mole (methods described in Example 6). Thus, the presence of the Tinoco et al. hairpin sequence increases the folding energy by 11.7 Kcal/mole.

However, the simple replacement of Loop III with the sequence UUCG (see FIG. 42C) gives an inactive ribozyme. This is believed to occur because the bases of Loop III help stabilize Helix 4.

When Loop III of the native ribozyme is cut between U31 and U32, activity is lost (see FIG. 42C). A likely explanation for this is that when the loop is cut, Helix 4 opens up and catalytic activity is, consequently, lost. The "cut" ribozyme was prepared by synthesizing the ribozyme in two parts and allowing the parts to anneal.

With the extension of Helix 4 by the Tinoco et al. hairpin sequence, the potential base pair C29:G33 is between the two proven bases of Helix 4 and the four base pairs of the Tinoco sequence. Accordingly, it seemed likely that this base pair existed. However, both the single mutation G33→C and the double mutation C29:G33→G29:C33 were inactive (see FIG. 42C). Either a base pair does not exist at this position or the identity of the bases must be maintained. This second possibility seems the most likely since the ribozyme likely needs to be involved in specific three-dimensional folding to carry out catalysis, and specific functional groups on the bases may be involved in the folding and/or the catalysis itself.

The existence of other base pairs in Helix 4 could not be shown. The next potential base pair up-stream in Helix 4 was C25:G36. The single mutation C25→G was inactive (FIG. 42C). The double mutation, G25:C36, was also inactive (FIG. 42C), indicating that a base pair does not actually exist. Although the base pair could exist with the identity of the bases being required, this appears unlikely since the G and C are not directly opposite each other since there is A between the C and the next proven base pair. By the same sort of analysis, the next potential base pair upstream, A24:U37, was shown not to exist. When the mutation A24:U37→G24:C37 was made, no activity was seen (FIG. 42C), indicating that a base pair does not exist at this position.

Further mutation studies showed that Loops II and IV are larger than originally predicted by computer modeling and energy minimization (compare FIGS. 1 and 42D). Also, some of the bases in these loops are required for activity.

As already shown in Example 12, when bases A22, A23 and A24 in Loop II were mutated to GUC, a totally inactive ribozyme was obtained, indicating that one or all of these bases are essential. The single mutation in Loop II of C25→G was inactive (see FIG. 42C). The double mutation C25→G +G36→C was also inactive (see FIG. 42C).

In Loop IV, the single mutation U39→G was active (see FIG. 42A), indicating that this base was not essential for catalytic activity and was not involved in a base pair. The single mutation A43→U was inactive, as was the double mutation A43→U and U37→A. This result was significant because the possibility existed for a stem to occur in Loop IV:

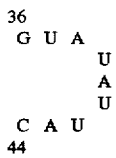

If this stem existed, the A43:U37 alternate base pair of U43:A37 should have been active. Since it was not, it was concluded that a stem in Loop IV does not exist.

In Loop V, the loop formed by the cleavage sequence in the substrate molecule, the bases guc are invariant and are not base paired to the catalyst (see Example 25 and FIG. 42C).

All of the bases of Loop I in the ribozyme, the loop opposite Loop V, have been mutated. When base A7 was changed to a G or C and when base A10 was changed to a G, the resulting catalysts were active (FIG. 42A). However, when base G8 was changed to a U or C or when base A9 was changed to U, inactive ribozymes were produced (see FIG. 42C).

Potential base pairs between Loop V in the substrate and the Loop I in the ribozyme were tested. In particular, experiments to determine whether G8 and A9 of Loop I were base paired with the corresponding bases in substrate Loop V were performed. Mutations tested were G8→C:c8→g and A9→U:u7→a. These mutations were inactive (see FIG. 42C), showing that, for the bases checked, no base pairs existed.

While the c9→a mutation in substrate Loop V was inactive (FIG. 42C) and the A7→C mutation of ribozyme Loop I was fully active (FIG. 42A), the double mutation of c9→a and A7→C showed partial activity (see FIG. 42B). This suggests that some type of interaction may be occurring between base c9 of the substrate and base A7 of the ribozyme which are opposite each other in the loops.

A triple mutation comprising this same double mutation plus changing base A20→C in the ribozyme showed the same level of activity as the double mutation (FIG. 42B). The triple mutation represents base changes in the ArMV sequence proposed to be catalytic (Gerlach and Haseloff, *Gene*, 82, 43–52 (1989)) and would suggest that a triple base interaction might occur between the three bases. However, the catalyst containing the triple mutation gave catalytic activity at the same level as the double mutation, arguing against a triple base interaction. The results obtained with the catalyst containing the double mutation, however, indicate that an interaction of some type takes place between substrate C9 and ribozyme A7.

As various changes could be made in the above-described products and methods without departing from the scope of the invention, it is intended that all matter contained in the above description or shown in accompanying drawings shall be interpreted as illustrative and shall not be interpreted in a limiting sense.

We claim:

1. A compound having an autocatalytic portion comprising the structure:

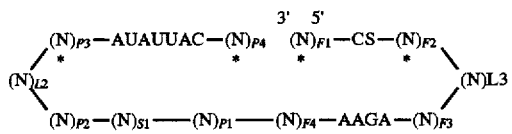

wherein each N represents a ribonucleotide which may be the same or different;

wherein each of $(N)_{F1}$, $(N)_{F2}$, $(N)_{F3}$ and $(N)_{F4}$ represents an oligonucleotide having a predetermined sequence which is capable of hybridizing with an RNA target sequence to be cleaved;

wherein F2 represents an integer which defines the number of nucleotides in the oligonucleotide with the proviso that F3 is greater than or equal to 3;

wherein F1 represents an integer which defines the number of nucleotides in the oligonucleotide with the proviso that F4 is from 3 to 5;

wherein F3 represents an integer which defines the number of nucleotides in the oligonucleotide with the proviso that F3 is greater than or equal to 3;

wherein F4 represents an integer which defines the number of nucleotides in the oligonucleotide with the proviso that F4 is from 3 to 5;

wherein each of $(N)_{P1}$ and $(N)_{P4}$ represents an oligonucleotide having a predetermined sequence such that $(N)_{P4}$ base-pairs with 3-6 bases of $(N)_{P1}$;

wherein P1 represents an integer which defines the number of nucleotides in the oligonucleotide with the proviso that P1 is from 3 to 6;

wherein $(N)_{S1}$ represents an oligonucleotide having a predetermined sequence of 3-7 base-pairs such that $(N)_{S1}$ is substantially unpaired;

wherein each of $(N)_{P2}$ and $(N)_{P3}$ represents an oligonucleotide having a predetermined sequence such that $(N)_{P2}$ base-pairs with at least 3 bases of $(N)_{P3}$;

wherein each * represents base pairing between the nucleotides located on either side thereof;

wherein each solid line represents a chemical linkage providing covalent bonds between the nucleotides located on either side thereof;

wherein each of the dashed lines independently represents either a chemical linkage providing covalent bonds between the nucleotides located on either side thereof or the absence of any such chemical linkage; and wherein $(N)_{L2}$ represents an oligonucleotide with the proviso that L2 represents an integer which is greater than or equal to 3;

wherein $(N)_{L3}$ represents an oligonucleotide;

provided that $(N)_{F4}$—AAGA—$(N)_{F3}$-5' does not comprise ACUGAAGAGACAAA.

2. The compound of claim 1 wherein the compound comprises the structure:

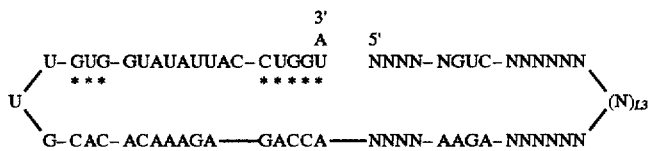

3. The compound of claim 1 wherein 5'-$(N)_{P2}$---$(N)_{L2}$---$(N)_{P3}$ comprises the sequence 5'-GGAC(UUCG)GUCC-3'.

4. A composition which comprises the compound of claim 1, in association with a acceptable carrier.

5. An engineered DNA molecule coding for the compound of claim 1.

6. A vector operatively linked to expression control sequences containing a nucleotide sequence which on transcription gives rise to the compound of claim 1.

7. The vector of claim 6, wherein the vector is capable of self-replication in a host.

8. A composition which comprises the vector of claim 6 in association with a pharmaceutically acceptable carrier.

9. A host cell transformed with a vector of claim 6.

10. The host cell of claim 9 wherein the host cell is a prokaryotic cell, an eukaryotic cell, a plant cell, an animal cell or a human cell.

11. A method of terminating an RNA transcript comprising transforming a host cell with a vector comprising DNA coding for an RNA transcript according to claim 1, culturing the host cell so that RNA is transcribed and the autocatalytic portion cleaves the RNA transcript to terminate the transcript.

12. A method of using a vector operatively linked to expression control sequences containing a nucleotide sequence which on transcription gives rise to the compound of claim 1.

* * * * *